US008722641B2

(12) United States Patent
Kastan et al.

(10) Patent No.: US 8,722,641 B2
(45) Date of Patent: May 13, 2014

(54) OLIGONUCLEOTIDES WHICH INHIBIT P53 INDUCTION IN RESPONSE TO CELLULAR STRESS

(75) Inventors: Michael B. Kastan, Chapel Hill, NC (US); Jing Chen, Morrisville, NC (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 13/575,492

(22) PCT Filed: Jan. 28, 2011

(86) PCT No.: PCT/US2011/022930
§ 371 (c)(1),
(2), (4) Date: Jul. 26, 2012

(87) PCT Pub. No.: WO2011/094546
PCT Pub. Date: Aug. 4, 2011

(65) Prior Publication Data
US 2012/0302628 A1    Nov. 29, 2012

Related U.S. Application Data

(60) Provisional application No. 61/299,630, filed on Jan. 29, 2010.

(51) Int. Cl.
*C07H 21/04* (2006.01)
(52) U.S. Cl.
USPC .............................. 514/44; 536/24.5; 435/375
(58) Field of Classification Search
None
See application file for complete search history.

(56) References Cited

U.S. PATENT DOCUMENTS

| 2002/0151515 A1 | 10/2002 | Roberts |
| 2003/0175771 A1 | 9/2003 | Velculescu et al. |
| 2003/0175862 A1 | 9/2003 | Brachmann |
| 2003/0215803 A1 | 11/2003 | Garcia et al. |
| 2004/0048256 A1 | 3/2004 | Agee et al. |
| 2004/0259247 A1 | 12/2004 | Tuschl et al. |
| 2006/0199778 A1 | 9/2006 | Ellis et al. |
| 2007/0003936 A1 | 1/2007 | Gite et al. |
| 2009/0149377 A1 | 6/2009 | Takagi et al. |

FOREIGN PATENT DOCUMENTS

| WO | WO03050236 A2 | 6/2003 |
| WO | WO2007041213 A3 | 4/2009 |

OTHER PUBLICATIONS

Bae, Byoung-Il, et al., "p53 Mediates Cellular Dysfunction and Behavioral Abnormalities in Huntington's Disease," Neuron, (2005) vol. 47, p. 29-41.
Bates, Paula J., et al., "Antiproliferative Activity of G-rich Oligonucleotides Correlates with Protein Binding," The Journal of Biological Chemistry, (1999) vol. 274, No. 37, p. 26369-26377.
Botchkarev, Vladimir, et al., "p53 Is Essential for Chemotherapy-induced Hair Loss," Cancer Research, (2000) vol. 60, p. 5002-5006.
Bunz, Fred, et al., "Disruption of p53 in Human Cancer Cells Alters the Responses to Therapeutic Agents," The Journal of Clinical Investigation, (1999) vol. 104, No. 3, p. 263-269.
Chen, Zhenbang, et al., "Crucial Role of p53-Dependent Cellular Senescence in Suppression of pten-deficient Tumorigenesis," Nature, (2005) vol. 436, p. 725-730.
Chen et al., "5'-3'-UTR interactions regulate p53 mRNA translation and provide a target for modulating p53 induction after DNA damage", Genes Dev., (2010) vol. 24(19), p. 2146-56.
Chu, E., et al., "Thymidylate Synthase Protein and p53 mRNA form an In Vivo Ribonucleoprotein Complex," Molecular and Cellular Biology, (1999) vol. 19, No. 2, p. 1582-1594.
Dai, Mu-Shui, et al., "Inhibition of MDM2-Mediated p53 Ubiquitination and Degradation by Ribosomal Protein L5," Journal of Biological Chemistry, (2004) vol. 279, No. 43, p. 44475-44482.
Dai, Mu-Shui, et al., "Ribosomal Protein L23 Activates p53 by Inhibiting MDM2 Function in Response to Ribosomal Perturbation but Not to Translation Inhibition," Molecular and Cellular Biology, (2004) vol. 24, No. 17, p. 7654-7668.
Daniely et al. "Stress-Dependent Nucleolin Mobilization Mediated by p53-Nucleolin Complex Formation" Molecular and Cellular Biology, (2002) vol. 22, No. 16, p. 6014-6022.
Dapic, Virna, et al., "Biophysical and Biological Properties of Quadruplex Oligodeoxyribonucleotides," Nucleic Acids Research, (2003) vol. 31, No. 8, p. 2097-2107.
Erratum to Takagi, Masatoshi, et al., Cell, (2005) vol. 123, No. 3, p. 536-7.
Ferber, Dan, "The New Way to Combat Therapy Side Effects," Science, (1999) vol. 285, p. 1651-1653.
Fu, Loning, et al., "Translational Regulation of Human p53 Gene Expression," The EMBO Journal, (1996) vol. 15, No. 16, p. 4392-4401.
Fu, Loning., et al., "Participation of the Human p53 3' UTR in Translational Repression and Activation Following Gamma-Irradiation," The EMBO Journal, (1997) vol. 16, No. 13, p. 4117-4125.
Fu, Loning, et al., "A Translation Repressor Element Resides in the 3' Untranslated Region of Human p53 mRNA," Oncogene, (1999) vol. 18, p. 6419-6424.
Gudkov, Andrei V., et al., "The Role of p53 in Determining Sensitivity to Radiotherapy," Nature Reviews/Cancer, (2003) vol. 3, p. 117-129.
Gudkov, "Cancer Drug Discovery: the Wisdom of Imprecision," Nature Medicine,(2004) vol. 10, No. 12, p. 1298-1299.
Haass, Christian, "New Hope for Alzheimer Disease Vaccine," Nature Medicine, (2002) vol. 8, No. 11, p. 1195-1199.

(Continued)

*Primary Examiner* — Kimberly Chong
(74) *Attorney, Agent, or Firm* — Troutman Sanders LLP

(57) ABSTRACT

The present invention relates to novel oligonucleotides which comprise p53 5'-UTR sequence TCCCTGG (SEQ ID NO: 1) or the complementary p53 3'-UTR sequence CCAGGGA (SEQ ID NO: 2) and their use for such therapeutic applications as protection of normal tissues from the toxicities of chemical or radiation exposure; reducing tissue damage in hypoxia-reperfusion injury, neurodegenerative disorders, oxidative stress, injuries, hyperthermia; preventing aging; preservation of tissues and organs prior to transplanting, etc.

21 Claims, 13 Drawing Sheets

(56) References Cited

OTHER PUBLICATIONS

Horton et al. "p53 Activation Results in Rapid Dephospohorlyation of the eIF4E-Binding Protein 4E-BP1, Inhibition of Ribosomal Protein S6 Kinase and Inhibition of Translation Initiation." Oncogene, (2002) vol. 21, No. 34, p. 5325-5334.

International Search Report and Written Opinion of the International Searching Authority, mailed Aug. 4, 2011, which issued in International Application Serial No. PCT/US2011/022930.

Jin, Aiwen, et al., "Inhibition of HDM2 and Activation of p53 by Ribosomal Protein L23," Molecular & Cellular Biology, (2004) vol. 24, No. 17, p. 7669-7680.

Ju, J., et al., "Regulation of p53 Expression by Thymidylate Synthase," Proceedings of the National Academy of Science U.S.A, (1999) vol. 96, No. 7, p. 3769-3774.

Kastan, MB, et al., "A Mammalian Cell Cycle Checkpoint Pathway Utilizing p53 and GADD45 is Defective in Ataxia-Telangiectasia," Cell, (1992) vol. 71, p. 587-597.

Kastan, MB, et al., "Participation of p53 Protein in the Cellular Response to DNA Damage," Cancer Research, (1991) vol. 51, p. 6304-6311.

Komarov, P.G., et al. "A chemical inhibitor of p53 that protects mice from the side effects of cancer therapy", Science (1999) vol. 285, p. 1733-1737.

Komarova, Elena A., "Chemoprotection from p53-dependent Apoptosis: Potential Clinical Applications of the p53 Inhibitors," Biochemical Pharmacology, (2001) vol. 62, p. 657-667.

Lohrum, Marion E., et al., "Regulation of HDM2 Activity by the Ribosomal Protein L11," Cancer Cell, (2003) vol. 3, No. 6, p. 577-587.

Mazan-Mamczarz, K., et al., "RNA-Binding Protein HuR Enhances p53 Translation in Response to Ultraviolet Light Irradiation," Proceedings of the National Academy of Science U.S.A., (2003) vol. 100, No. 14, p. 8354-8359.

Mokdad-Gagouri, et al. "Translational Control of Human p53 Expression in Yeast Mediated by 5'-UTR-ORF Structural Interactions." Nucleic Acids Research, (2001) vol. 29, No. 5, p. 1222-1227.

Mosner, J., et al., "Negative Feedback Regulation of Wild-Type p53 Biosynthesis," The EMBO Journal, (1995) vol. 14, No. 18, p. 4442-4449.

Ofir-Rosenfeld, Y., et al. "Mdm2 Regulates p53 mRNA Translation through Inhibitory Interactions with Ribosomal Protein L26," Molecular Cell (2008) vol. 32, p. 180-189.

Schumacher, B., et al. "Translational repression of *C. elegans* p53 by GLD-1 regulates DNA damage-induced apoptosis," Cell (2005) vol. 120, p. 357-368.

Takagi, Masatoshi, et al., "Regulation of p53 Translation and Induction after DNA Damage by Ribosomal Protein L26 and Nucleolin," Cell, (2005) vol. 123, p. 49-63.

Xu, Xiaohua, et al., "Inhibition of DNA Replication and Induction of S Phase Cell Cycle Arrest by G-rich Oligonucleotides," The Journal of Biological Chemistry, (2001) vol. 276, No. 46, p. 43221-43230.

Yang, Chonglin, et al., "Identification of Nucleolin and Nucleophosmin as Genotoxic Stress-Responsive RNA-Binding Proteins," Nucleic Acids Research, (2002) vol. 30, No. 10, p. 2251-2260.

Yang et al., "The identification of an internal ribosomal entry site in the 5'-untranslated region of p53 mRNA provides a novel mechanism for the regulation of its translation following DNA damage" Oncogene (2006) vol. 25, p. 4613-4619.

Zhang, et al. "Identification and Analysis of Over 2000 Ribosomal Protein Pseudogenes in the Human Genome" Genome Research, (2002) vol. 12, No. 10, p. 1466-1482.

Zhang, Yanping, et al., "Ribosomal Protein L11 Negatively Regulates Oncoprotein MDM2 and Mediated a p53-Dependent Ribosomal-Stress Checkpoint Pathway," Molecular & Cellular Biology, (2003) vol. 23, No. 23, p. 8902-8912.

International Search Report and Written Opinion of the International Searching Authority, mailed May 5, 2008, which issued in International Application Serial No. PCT/US2006/037848.

Human                                    Chimp

SEQUENCE LISTING

```
<160> NUMBER OF SEQ ID NOS: 54

<210> SEQ ID NO 1
<211> LENGTH: 7
<212> TYPE: DNA
<213> ORGANISM: Artificial Sequence
<220> FEATURE:
<223> OTHER INFORMATION: oligonucleotide

<400> SEQUENCE: 1 tccctgg                                                                  7

<210> SEQ ID NO 2
<211> LENGTH: 7
<212> TYPE: DNA
<213> ORGANISM: Artificial Sequence
<220> FEATURE:
<223> OTHER INFORMATION: oligonucleotide

<400> SEQUENCE: 2 ccaggga                                                                  7

<210> SEQ ID NO 3
<211> LENGTH: 8
<212> TYPE: DNA
<213> ORGANISM: Artificial Sequence
<220> FEATURE:
<223> OTHER INFORMATION: oligonucleotide

<400> SEQUENCE: 3 ttccctgg                                                                 8

<210> SEQ ID NO 4
<211> LENGTH: 8
<212> TYPE: DNA
```

```
<213> ORGANISM: Artificial Sequence
<220> FEATURE:
<223> OTHER INFORMATION: oligonucleotide

<400> SEQUENCE: 4 ccagggaa                                                                    8

<210> SEQ ID NO 5
<211> LENGTH: 9
<212> TYPE: DNA
<213> ORGANISM: Artificial Sequence
<220> FEATURE:
<223> OTHER INFORMATION: oligonucleotide

<400> SEQUENCE: 5 cttccctgg                                                                   9

<210> SEQ ID NO 6
<211> LENGTH: 9
<212> TYPE: DNA
<213> ORGANISM: Artificial Sequence
<220> FEATURE:
<223> OTHER INFORMATION: oligonucleotide

<400> SEQUENCE: 6 ccagggaag                                                                   9

<210> SEQ ID NO 7
<211> LENGTH: 12
<212> TYPE: DNA
<213> ORGANISM: Artificial Sequence
<220> FEATURE:
<223> OTHER INFORMATION: oligonucleotide

<400> SEQUENCE: 7
acgcttccct gg                                                              12

<210> SEQ ID NO 8
<211> LENGTH: 12
<212> TYPE: DNA
<213> ORGANISM: Artificial Sequence
<220> FEATURE:
<223> OTHER INFORMATION: oligonucleotide

<400> SEQUENCE: 8
ccagggaagc gt                                                              12

<210> SEQ ID NO 9
<211> LENGTH: 15
<212> TYPE: DNA
<213> ORGANISM: Artificial Sequence
<220> FEATURE:
<223> OTHER INFORMATION: oligonucleotide

<400> SEQUENCE: 9
gacacgcttc cctgg                                                           15

<210> SEQ ID NO 10
<211> LENGTH: 15
<212> TYPE: DNA
<213> ORGANISM: Artificial Sequence
<220> FEATURE:
<223> OTHER INFORMATION: oligonucleotide

<400> SEQUENCE: 10
ccagggaagc gtgtc                                                           15
```

```
<210> SEQ ID NO 11
<211> LENGTH: 18
<212> TYPE: DNA
<213> ORGANISM: Artificial Sequence
<220> FEATURE:
<223> OTHER INFORMATION: oligonucleotide

<400> SEQUENCE: 11
ggtgacacgc ttccctgg                                                 18

<210> SEQ ID NO 12
<211> LENGTH: 18
<212> TYPE: DNA
<213> ORGANISM: Artificial Sequence
<220> FEATURE:
<223> OTHER INFORMATION: oligonucleotide

<400> SEQUENCE: 12
ccagggaagc gtgtcacc                                                 18

<210> SEQ ID NO 13
<211> LENGTH: 21
<212> TYPE: DNA
<213> ORGANISM: Artificial Sequence
<220> FEATURE:
<223> OTHER INFORMATION: oligonucleotide

<400> SEQUENCE: 13
gacggtgaca cgcttccctg g                                             21

<210> SEQ ID NO 14
<211> LENGTH: 21
<212> TYPE: DNA
<213> ORGANISM: Artificial Sequence
<220> FEATURE:
<223> OTHER INFORMATION: oligonucleotide

<400> SEQUENCE: 14
ccagggaagc gtgtcaccgt c                                             21

<210> SEQ ID NO 15
<211> LENGTH: 15
<212> TYPE: DNA
<213> ORGANISM: Artificial Sequence
<220> FEATURE:
<223> OTHER INFORMATION: oligonucleotide

<400> SEQUENCE: 15
tttacgcttc cctgg                                                    15

<210> SEQ ID NO 16
<211> LENGTH: 15
<212> TYPE: DNA
<213> ORGANISM: Artificial Sequence
<220> FEATURE:
<223> OTHER INFORMATION: oligonucleotide

<400> SEQUENCE: 16
gacacaacca actgg                                                    15

<210> SEQ ID NO 17
<211> LENGTH: 15
<212> TYPE: DNA
<213> ORGANISM: Artificial Sequence
<220> FEATURE:
<223> OTHER INFORMATION: oligonucleotide
```

-continued

```
<400> SEQUENCE: 17
gacacgcttc ccaaa                                                    15

<210> SEQ ID NO 18
<211> LENGTH: 15
<212> TYPE: DNA
<213> ORGANISM: Artificial Sequence
<220> FEATURE:
<223> OTHER INFORMATION: oligonucleotide

<400> SEQUENCE: 18
ggtgacacgc ttccc                                                    15

<210> SEQ ID NO 19
<211> LENGTH: 15
<212> TYPE: DNA
<213> ORGANISM: Artificial Sequence
<220> FEATURE:
<223> OTHER INFORMATION: oligonucleotide

<400> SEQUENCE: 19
agggcgtatc tcttc                                                    15

<210> SEQ ID NO 20
<211> LENGTH: 18
<212> TYPE: DNA
<213> ORGANISM: Artificial Sequence
<220> FEATURE:
<223> OTHER INFORMATION: oligonucleotide

<400> SEQUENCE: 20
gacggtgaca cgcttccc                                                 18

<210> SEQ ID NO 21
<211> LENGTH: 18
<212> TYPE: DNA
<213> ORGANISM: Artificial Sequence
<220> FEATURE:
<223> OTHER INFORMATION: oligonucleotide

<400> SEQUENCE: 21
agggcgtatc tcttcata                                                 18

<210> SEQ ID NO 22
<211> LENGTH: 21
<212> TYPE: DNA
<213> ORGANISM: Artificial Sequence
<220> FEATURE:
<223> OTHER INFORMATION: oligonucleotide

<400> SEQUENCE: 22
accagggcgt atctcttcat a                                             21

<210> SEQ ID NO 23
<211> LENGTH: 22
<212> TYPE: DNA
<213> ORGANISM: Artificial Sequence
<220> FEATURE:
<223> OTHER INFORMATION: oligonucleotide

<400> SEQUENCE: 23
gctgggagcg tgctttccac ga                                            22

<210> SEQ ID NO 24
<211> LENGTH: 21
<212> TYPE: DNA
```

```
<213> ORGANISM: Artificial Sequence
<220> FEATURE:
<223> OTHER INFORMATION: oligonucleotide

<400> SEQUENCE: 24
ctgccttccg ggtcactgcc a                                        21

<210> SEQ ID NO 25
<211> LENGTH: 22
<212> TYPE: DNA
<213> ORGANISM: Artificial Sequence
<220> FEATURE:
<223> OTHER INFORMATION: oligonucleotide

<400> SEQUENCE: 25
tcgtggaaag cacgctccca gc                                       22

<210> SEQ ID NO 26
<211> LENGTH: 21
<212> TYPE: DNA
<213> ORGANISM: Artificial Sequence
<220> FEATURE:
<223> OTHER INFORMATION: oligonucleotide

<400> SEQUENCE: 26
tggcagtgac ccggaaggca g                                        21

<210> SEQ ID NO 27
<211> LENGTH: 55
<212> TYPE: DNA
<213> ORGANISM: Artificial Sequence
<220> FEATURE:
<223> OTHER INFORMATION: oligonucleotide

<400> SEQUENCE: 27
ggatcctaat acgactcact ataggagcca tcatggtgaa gctcgcgaag gcagg   55

<210> SEQ ID NO 28
<211> LENGTH: 33
<212> TYPE: DNA
<213> ORGANISM: Artificial Sequence
<220> FEATURE:
<223> OTHER INFORMATION: oligonucleotide

<400> SEQUENCE: 28
ctattcaaac ttcgtcttct ttccttgtgg ctt                           33

<210> SEQ ID NO 29
<211> LENGTH: 23
<212> TYPE: DNA
<213> ORGANISM: Artificial Sequence
<220> FEATURE:
<223> OTHER INFORMATION: oligonucleotide

<400> SEQUENCE: 29
gatataggcg ccagcaaccg cac                                      23

<210> SEQ ID NO 30
<211> LENGTH: 30
<212> TYPE: DNA
<213> ORGANISM: Artificial Sequence
<220> FEATURE:
<223> OTHER INFORMATION: oligonucleotide

<400> SEQUENCE: 30
taatacgact cactataggg agacccaagc                               30
```

<210> SEQ ID NO 31
<211> LENGTH: 9
<212> TYPE: DNA
<213> ORGANISM: Artificial Sequence
<220> FEATURE:
<223> OTHER INFORMATION: oligonucleotide

<400> SEQUENCE: 31 ggtgacacg                                                              9

<210> SEQ ID NO 32
<211> LENGTH: 12
<212> TYPE: DNA
<213> ORGANISM: Artificial Sequence
<220> FEATURE:
<223> OTHER INFORMATION: oligonucleotide

<400> SEQUENCE: 32
ggtgacacgc tt                                                         12

<210> SEQ ID NO 33
<211> LENGTH: 32
<212> TYPE: DNA
<213> ORGANISM: Artificial Sequence
<220> FEATURE:
<223> OTHER INFORMATION: oligonucleotide

<400> SEQUENCE: 33
atgcgaattc cttctcaaaa gtctagagcc ac                                   32

<210> SEQ ID NO 34
<211> LENGTH: 34
<212> TYPE: DNA
<213> ORGANISM: Artificial Sequence
<220> FEATURE:
<223> OTHER INFORMATION: oligonucleotide

<400> SEQUENCE: 34
gtgagcatgc atggcagtga cccggaaggc agtc                                 34

<210> SEQ ID NO 35
<211> LENGTH: 2586
<212> TYPE: DNA
<213> ORGANISM: Homo sapiens

<400> SEQUENCE: 35
gattggggtt ttcccctccc atgtgctcaa gactggcgct aaaagttttg agcttctcaa      60
aagtctagag ccaccgtcca gggagcaggt agctgctggg ctccggggac actttgcgtt     120
cgggctggga gcgtgctttc cacgacggtg acacgcttcc tggattggca gccagactg      180 ccttccgggt cactgccatg gaggagccgc agtcagatcc tagcgtcgag ccccctctga     240
gtcaggaaac attttcagac ctatggaaac tacttcctga aaacaacgtt ctgtcccct      300 tgccgtccca gcaatggat gatttgatgc tgtccccgga cgatattgaa caatggttca      360
ctgaagaccc aggtccagat gaagctccca gaatgccaga ggctgctccc ccgtggccc      420 ctgcaccagc agctcctaca ccggcggccc ctgcaccagc ccctcctgg ccctgtcat       480 cttctgtccc ttcccagaaa acctaccagg gcagctacgg tttccgtctg ggcttcttgc     540
attctgggac agccaagtct gtgacttgca cgtactcccc tgccctcaac aagatgtttt     600
gccaactggc caagacctgc cctgtgcagc tgtgggttga ttccacaccc cgcccggca      660 cccgcgtccg cgccatggcc atctacaagc agtcacagca catgacggag gttgtgaggc     720

```
gctgccccca  ccatgagcgc  tgctcagata  gcgatggtct  ggcccctcct  cagcatctta      780
tccgagtgga  aggaaatttg  cgtgtggagt  atttggatga  cagaaacact  tttcgacata      840
gtgtggtggt  gccctatgag  ccgcctgagg  ttggctctga  ctgtaccacc  atccactaca      900
actacatgtg  taacagttcc  tgcatgggcg  gcatgaaccg  gaggcccatc  ctcaccatca      960
tcacactgga  agactccagt  ggtaatctac  tgggacggaa  cagctttgag  gtgcgtgttt     1020
gtgcctgtcc  tgggagagac  cggcgcacag  aggaagagaa  tctccgcaag  aaaggggagc     1080
ctcaccacga  gctgccccca  gggagcacta  agcgagcact  gcccaacaac  accagctcct     1140
ctccccagcc  aaagaagaaa  ccactggatg  agaatatttt  cacccttcag  atccgtgggc     1200
gtgagcgctt  cgagatgttc  cgagagctga  atgaggcctt  ggaactcaag  gatgcccagg     1260
ctgggaagga  gccagggggg  agcagggctc  actccagcca  cctgaagtcc  aaaaagggtc     1320
agtctacctc  ccgccataaa  aaactcatgt  tcaagacaga  agggcctgac  tcagactgac     1380
attctccact  tcttgttccc  cactgacagc  ctcccacccc  catctctccc  tcccctgcca     1440
ttttgggttt  tgggtctttg  aacccttgct  tgcaataggt  gtgcgtcaga  agcacccagg     1500
acttccattt  gctttgtccc  ggggctccac  tgaacaagtt  ggcctgcact  ggtgttttgt     1560
tgtggggagg  aggatgggga  gtaggacata  ccagcttaga  ttttaaggtt  tttactgtga     1620
gggatgtttg  ggagatgtaa  gaatgttct  tgcagttaag  ggttagttta  caatcagcca     1680
cattctaggt  aggggcccac  ttcaccgtac  taaccaggga  agctgtccct  cactgttgaa     1740
ttttctctaa  cttcaaggcc  catatctgtg  aaatgctggc  atttgcacct  acctcacaga     1800
gtgcattgtg  agggttaatg  aaataatgta  catctggcct  tgaaaccacc  ttttattaca     1860
tggggtctag  aacttgaccc  ccttgagggt  gcttgttccc  tctccctgtt  ggtcggtggg     1920
ttggtagttt  ctacagttgg  gcagctgtt  aggtagaggg  agttgtcaag  tctctgctgg     1980
cccagccaaa  ccctgtctga  caacctcttg  gtgaacctta  gtacctaaaa  ggaaatctca     2040
ccccatccca  caccctggag  gatttcatct  cttgtatatg  atgatctgga  tccaccaaga     2100
cttgttttat  gctcagggtc  aatttctttt  ttcttttttt  tttttttttt  tcttttttctt     2160 tgagactggg  tctcgctttg  ttgcccaggc  tggagtggag  tggcgtgatc  ttggcttact     2220
gcagcctttg  cctccccggc  tcgagcagtc  ctgcctcagc  ctccggagta  gctgggacca     2280
caggttcatg  ccaccatggc  cagccaactt  ttgcatgttt  tgtagagatg  gggtctcaca     2340
gtgttgccca  ggctggtctc  aaactcctgg  gctcaggcga  tccacctgtc  tcagcctccc     2400
agagtgctgg  gattacaatt  gtgagccacc  acgtccagct  ggaagggtca  acatctttta     2460
cattctgcaa  gcacatctgc  attttcaccc  cacccttccc  ctccttctcc  cttttatat     2520 cccatttta  tatcgatctc  ttattttaca  ataaaacttt  gctgccacct  gtgtgtctga     2580
ggggtg                                                                     2586

<210> SEQ ID NO 36
<211> LENGTH: 2534
<212> TYPE: DNA
<213> ORGANISM: Homo sapiens

<400> SEQUENCE: 36
cttctcaaaa  gtctagagcc  accgtccagg  gagcaggtag  ctgctgggct  ccggggacac       60
tttgcgttcg  ggctgggagc  gtgctttcca  cgacggtgac  acgcttccct  ggattggcag      120
ccagactgcc  ttccgggtca  ctgccatgga  ggagccgcag  tcagatccta  gcgtcgagcc      180
ccctctgagt  caggaaacat  tttcagacct  atggaaacta  cttcctgaaa  acaacgttct      240
```

| | |
|---|---|
| gtcccccttg ccgtcccaag caatggatga tttgatgctg tccccggacg atattgaaca | 300 |
| atggttcact gaagacccag gtccagatga agctcccaga atgccagagg ctgctccccc | 360 |
| cgtggcccct gcaccagcag ctcctacacc ggcggcccct gcaccagccc cctcctggcc | 420 |
| cctgtcatct tctgtcccctt cccagaaaac ctaccagggc agctacggtt tccgtctggg | 480 |
| cttcttgcat tctgggacag ccaagtctgt gacttgcacg tactcccctg ccctcaacaa | 540 |
| gatgttttgc caactggcca agacctgccc tgtgcagctg tgggttgatt ccacaccccc | 600 |
| gcccggcacc cgcgtccgcg ccatggccat ctacaagcag tcacagcaca tgacggaggt | 660 |
| tgtgaggcgc tgcccccacc atgagcgctg ctcagatagc gatggtctgg ccctcctca | 720 |
| gcatcttatc cgagtggaag gaaatttgcg tgtggagtat ttggatgaca gaaacacttt | 780 |
| tcgacatagt gtggtggtgc cctatgagcc gcctgaggtt ggctctgact gtaccaccat | 840 |
| ccactacaac tacatgtgta acagttcctg catgggcggc atgaaccgga ggcccatcct | 900 |
| caccatcatc acactggaag actccagtgg taatctactg ggacggaaca gctttgaggt | 960 |
| gcgtgtttgt gcctgtcctg ggagagaccg gcgcacagag aagagaatc tccgcaagaa | 1020 |
| agggagcct caccacgagc tgcccccagg gagcactaag cgagcactgc caacaacac | 1080 |
| cagctcctct ccccagccaa agaagaaacc actggatgga gaatatttca cccttcagat | 1140 |
| ccgtgggcgt gagcgcttcg agatgttccg agagctgaat gaggccttgg aactcaagga | 1200 |
| tgcccaggct gggaaggagc caggggggag cagggctcac tccagccacc tgaagtccaa | 1260 |
| aaagggtcag tctacctccc gccataaaaa actcatgttc aagacagaag ggcctgactc | 1320 |
| agactgacat tctccacttc ttgttcccca ctgacagcct cccaccccca tctctccctc | 1380 |
| ccctgccatt tgggttttg ggtctttgaa cccttgcttg caataggtgt gcgtcagaag | 1440 |
| cacccaggac ttccatttgc tttgtcccgg ggctccactg aacaagttgg cctgcactgg | 1500 |
| tgttttgttg tggggaggag gatggggagt aggacatacc agcttagatt ttaaggtttt | 1560 |
| tactgtgagg gatgtttggg agatgtaaga aatgttcttg cagttaaggg ttagtttaca | 1620 |
| atcagccaca ttctaggtag gggcccactt caccgtacta accagggaag ctgtccctca | 1680 |
| ctgttgaatt ttctctaact tcaaggccca tatctgtgaa atgctggcat ttgcacctac | 1740 |
| ctcacagagt gcattgtgag ggttaatgaa ataatgtaca tctggccttg aaaccacctt | 1800 |
| ttattacatg gggtctagaa cttgacccc ttgagggtgc ttgttccctc tccctgttgg | 1860 |
| tcggtgggtt ggtagtttct acagttgggc agctggttag gtagagggag ttgtcaagtc | 1920 |
| tctgctggcc cagccaaacc ctgtctgaca acctcttggt gaaccttagt acctaaaagg | 1980 |
| aaatctcacc ccatcccaca ccctggagga tttcatctct tgtatatgat gatctggatc | 2040 |
| caccaagact tgtttatgc tcagggtcaa tttcttttt ctttttttt ttttttttc | 2100 |
| ttttttcttttg agactgggtc tcgctttgtt gcccaggctg gagtggagtg gcgtgatctt | 2160 |
| ggcttactgc agcctttgcc tccccggctc gagcagtcct gcctcagcct ccggagtagc | 2220 |
| tgggaccaca ggttcatgcc accatggcca gccaacttt gcatgttttg tagagatggg | 2280 |
| gtctcacagt gttgcccagg ctggtctcaa actcctgggc tcaggcgatc cacctgtctc | 2340 |
| agcctcccag agtgctggga ttacaattgt gagccaccac gtccagctgg aagggtcaac | 2400 |
| atcttttaca ttctgcaagc acatctgcat tttcaccca ccttcccct ccttctccct | 2460 |
| ttttatatcc cattttata tcgatctctt attttacaat aaaactttgc tgccacctgt | 2520 |
| gtgtctgagg ggtg | 2534 |

<210> SEQ ID NO 37

```
<211> LENGTH: 602
<212> TYPE: DNA
<213> ORGANISM: Homo sapiens

<400> SEQUENCE: 37
ataggtctcg cgagatcttt ggtaaactta cagaaccgga agcagcgtgt agttctcttc      60
ccttttgcgg ccatcaccga agcgggagcg gccaaaatga agtttaatcc ctttgtgact     120
tccgaccgaa gcaagaatcg caaaaggcat ttcaatgcac cttcccacat tcgaaggaag     180
attatgtctt cccctctttc caaagagctg agacagaagt acaacgtgcg atccatgccc     240
atccgaaagg atgatgaagt tcaggttgta cgtggacact ataaaggtca gcaaattggc     300
aaagtagtcc aggtttacag gaagaaatat gttatctaca ttgaacgggt gcagcgggaa     360
aaggctaatg cacaactgt ccacgtaggc attcaccca gcaaggtggt tatcactagg       420
ctaaaactgg acaaagaccg caaaaagatc ctcgaacgga agccaaatc tcgccaagta      480
ggaaaggaaa aggcaaata caaggaagaa accattgaga agatgcagga ataaagtaat      540
cttatataca agctttgatt aaaacttgaa acaaagagcc tgaaaaaaaa aaaaaaaaa      600
aa                                                                    602

<210> SEQ ID NO 38
<211> LENGTH: 208
<212> TYPE: DNA
<213> ORGANISM: Pan troglodytes
<220> FEATURE:
<221> NAME/KEY: misc_feature
<222> LOCATION: 27, 28, 37, 38, 62, 63, 68, 69, 70, 80, 81, 82
<223> OTHER INFORMATION: n = A,T,C or G

<400> SEQUENCE: 38
atatgttatc tacattgaac gggtgcnncg ggaaaannct aatggcacaa ctgtccacgt      60
anncattnnn cccagcaagn nngttatcac taggctaaaa ctggacaaag accgcaaaaa     120
gatccttgaa cggaaagcca atctcgcca agtaggaaag gaaaagggca aatacaagga      180
agaaaccatt gagaagatgc aggaataa                                        208

<210> SEQ ID NO 39
<211> LENGTH: 507
<212> TYPE: DNA
<213> ORGANISM: Macaca mulatta

<400> SEQUENCE: 39
ggccatcacc gaagtgggag cggccaaaat gaagtttaat ccctttgtga cttccgaccg      60
aagcaagaat cgcaaaaggc atttcaatgc accttcccac attcgcagga agattatgtc     120
ttcccctctt tccaaagagc tgagacagaa gtacaacgtg cgatccatgc ccatccgaaa     180
ggatgatgaa gttcaggttg tacgaggaca ctataaaggt cagcaaattg gcaaagtagt     240
ccaggtttac aggaagaagt atgttatcta cattgaacgg gtgcagcggg aaaaggctaa     300
tggcacaacg gtccacgtag gcattcaccc cagcaaggtg gttatcacta ggctaaaact     360
ggacaaagac cgcaaaaaga tccttgaacg gaaagccaaa tctcgccaag taggaaagga     420
aaagggcaaa tacaaggaag aaacaattga agatgcag gaataaagta atcttatata       480
aaagctttga ttaaaacttg aagcaaa                                         507

<210> SEQ ID NO 40
<211> LENGTH: 629
<212> TYPE: DNA
<213> ORGANISM: Bos taurus
```

<400> SEQUENCE: 40

```
gctcttccct tctgtggcca tcgctgaagc gctagcggcc aaaatgaagt tcaatccctt       60
tgtgacttct gaccgaagca agaatcgaaa aagacatttc aatgcgcctt cccacattcg      120
caggaaaatt atgtcttctc ctctttctaa agagctaaga cagaagtaca acgttcgatc      180
catgcccatc cgaaaggatg atgaagttca ggttgtacga gggcactaca aagggcagca      240
aattggcaaa gtagtccagg tttacaggaa gaaatacgtc atctacattg aacgagtgca      300
gcgggagaag gctaatggca caactgtcca cgtgggcatt caccccagca aggtggttat      360
caccagacta aaactggaca agaccgcaa aaagatcctc gaacgtaaag ccaaatctcg       420
ccaagtagga aggaaaaggg gcaaatataa ggaagaaaca attgagaaga tgcaagaata      480
aagtcatctt gtctacagct ttcattaaaa actgttaaaa tgaaaaaaaa aaaaaaaaa       540
aaaaaaaaaa aaaaaaaaaa aaaaaaaaaa aaaaaaaaaa aaaaaaaaaa aaaaaaaaaa      600
aaaaaaaaaa aagaaaaaaa aaaaaaaaa                                        629
```

<210> SEQ ID NO 41
<211> LENGTH: 1119
<212> TYPE: DNA
<213> ORGANISM: Rattus norvegicus

<400> SEQUENCE: 41

```
gttttcggcg ggttgtcccg ggtaatccgc agccatccgc ggcgaggcaa tgaggctttc       60
tgtcccgaga ccccgagaca gtcttgctgg cccagcatca gccagcgagc cgtactggga      120
tgaactcgtt ccatgtccta gccaggggcc gcggggctgg agagggccaa aatgaagttc      180
aatcccttcg tgacttctga ccgaagcaag aaccgcaaac ggcatttcaa tgcaccatct      240
cacattcgga ggaagatcat gtcttctccg ctttccaaag aactgagaca gaagtataat      300
gttcggtcta tgcccattcg aaaggacgac gaagttcagg ttgttcgagg acactacaaa      360
ggccagcaga ttggcaaagt ggtccaagtg tacaggaaga aatacgtcat ctacattgag      420
cgagtccagc gagagaaggc taacggcaca actgtccatg tgggcatcca ccccagcaag      480
gtggttatca ccaggctaaa gctggacaag gaccgcaaga gatcctgga gaggaaagcc       540
aagtcccggc aagtaggaaa ggagaagggc aaatacaagg aagaaactat cgagaagatg      600
caggagtaga aatgtcatgc ccagttttca ttaaagactg cttaagtagt cctgtcttgt      660
gtggtgtttt ccaagtacct tgtccctgtg ccttactctg cttctgtgtc agtccttggg      720
tctgagagga cagccacact tacgacact gtgacacatt gtgtggaatt aagagggtct       780
ttttttttc tgtttcctaa taattttgtg gaatcggag ctatggtgag ttttggactt       840
aatagttagc cttggcagcc tcagagtctt gcaatgccc ttatcctgag gggttctact       900
gaggtttcta ggatggccag ttgaaaatgg tctgatatct ggaagagcc caagagtcag       960
ttccccacct tgtgagtcct agaggttttc agtcttggag cctgatacca tctcacaggg     1020
cctaaattac ttgaaatgta ttggaaaaac ctgagaaatt cctgcagtgt ctacaaaagc     1080
cagaagaggg caccagatct ccttgaattg tcggcaccc                            1119
```

<210> SEQ ID NO 42
<211> LENGTH: 527
<212> TYPE: DNA
<213> ORGANISM: Xenopus tropicalis

<400> SEQUENCE: 42

```
gctctttttcc ggcggccata gtagactgag cggctggtaa ccatgaagtt cagtccgttt       60
```

| | |
|---|---|
| gtcacctcag accgcagcaa gaaccgcaag aggcacttta atgccccctc ccatgtgcgc | 120 |
| agaaagatca tgtcttctcc cctctctaag gagctaaggc aaaaatacag cgtccgctcc | 180 |
| atgcctatcc gcaaagatga tgaagtgcag gtggttcgtg gacattacaa aggccagcag | 240 |
| attggcaaag tagtacaagt gtacagaaag aaatacgtca tctacattga acgcgtgcag | 300 |
| cgtgaaaagg caaatggcac tactgttcat gtcggaattc accctagcaa ggtggtgatc | 360 |
| acaagactaa aacttgacaa agatcgcaag aagatcttgg agcgcaaggc caagtctcgc | 420 |
| caagttggca agagaaggg caaatacaag gaagaaacca tagaaaagat gcaagagtaa | 480 |
| tatgtcaata aatatactgt ttggtttcta caaaaaaaaa aaaaaaa | 527 |

<210> SEQ ID NO 43
<211> LENGTH: 538
<212> TYPE: DNA
<213> ORGANISM: Danio rerio

<400> SEQUENCE: 43

| | |
|---|---|
| tttttctttt ccggcggcca tcgtgacagg tcggcaggcc atcatgaagc tgaacacgtt | 60 |
| tgtgacgtcc tcccggcgca agaaccgtaa gcgccacttc aacgcgccgt cccacatccg | 120 |
| caggaaaatc atgtcgtctc cactgtccaa agagctgcgg cagaaataca acgtgcgctc | 180 |
| catgcccatc cgcaaggacg acgaggtcca ggtggttcgg ggacactaca aaggccagca | 240 |
| gatcggtaaa gtggtgcagg tctacaggaa gaagtacgtg atctacatcg agcgcgtgca | 300 |
| gcgggagaag gccaacggaa ccacagtcca tgtgggcatc accccagca aggttgtgat | 360 |
| caccaggcta aagctcgaca aggatcgcaa aaagatcctg gagcgcaagg ccaaatccag | 420 |
| acaggacatt aaggagaagg gcaaatacaa ggaggagacc atcgagaaga tgcaggagtg | 480 |
| aaggagctgt ttttgctaac aataaaagac tgtaaagttc aaaaaaaaaa aaaaaaaa | 538 |

<210> SEQ ID NO 44
<211> LENGTH: 2534
<212> TYPE: DNA
<213> ORGANISM: Homo sapiens

<400> SEQUENCE: 44

| | |
|---|---|
| cttctcaaaa gtctagagcc accgtccagg gagcaggtag ctgctgggct ccggggacac | 60 |
| tttgcgttcg ggctgggagc gtgctttcca cgacggtgac acgcttccca aaattggcag | 120 |
| ccagactgcc ttccgggtca ctgccatgga ggagccgcag tcagatccta gcgtcgagcc | 180 |
| ccctctgagt caggaaacat tttcagacct atggaaacta cttcctgaaa acaacgttct | 240 |
| gtccccttg ccgtcccaag caatggatga tttgatgctg tccccggacg atattgaaca | 300 |
| atggttcact gaagacccag gtccagatga agctcccaga atgccagagg ctgctccccc | 360 |
| cgtggcccct gcaccagcag ctcctacacc ggcggcccct gcaccagccc cctcctggcc | 420 |
| cctgtcatct tctgtcccct tcccagaaaac ctaccagggc agctacggtt tccgtctggg | 480 |
| cttcttgcat tctgggacag ccaagtctgt gacttgcacg tactcccctg ccctcaacaa | 540 |
| gatgttttgc caactggcca agacctgccc tgtgcagctg tgggttgatt ccacaccccc | 600 |
| gcccggcacc cgcgtccgcg ccatggccat ctacaagcag tcacagcaca tgacggaggt | 660 |
| tgtgaggcgc tgcccccacc atgagcgctg ctcagatagc gatggtctgg cccctcctca | 720 |
| gcatcttatc cgagtggaag gaaatttgcg tgtggagtat ttggatgaca gaaacacttt | 780 |
| tcgacatagt gtggtggtgc ctatgagcc gcctgaggtt ggctctgact gtaccaccat | 840 |
| ccactacaac tacatgtgta acagttcctg catgggcggc atgaaccgga ggcccatcct | 900 |

| | |
|---|---|
| caccatcatc acactggaag actccagtgg taatctactg ggacggaaca gctttgaggt | 960 |
| gcgtgtttgt gcctgtcctg ggagagaccg gcgcacagag gaagagaatc tccgcaagaa | 1020 |
| aggggagcct caccacgagc tgcccccagg gagcactaag cgagcactgc caacaacac | 1080 |
| cagctcctct ccccagccaa agaagaaacc actggatgga gaatatttca cccttcagat | 1140 |
| ccgtgggcgt gagcgcttcg agatgttccg agagctgaat gaggccttgg aactcaagga | 1200 |
| tgcccaggct gggaaggagc caggggggag cagggctcac tccagccacc tgaagtccaa | 1260 |
| aaagggtcag tctacctccc gccataaaaa actcatgttc aagacagaag ggcctgactc | 1320 |
| agactgacat tctccacttc ttgttcccca ctgacagcct cccaccccca tctctccctc | 1380 |
| ccctgccatt ttgggttttg ggtctttgaa cccttgcttg caataggtgt gcgtcagaag | 1440 |
| cacccaggac ttccatttgc tttgtcccgg ggctccactg aacaagttgg cctgcactgg | 1500 |
| tgttttgttg tggggaggag gatggggagt aggacatacc agcttagatt ttaaggtttt | 1560 |
| tactgtgagg gatgtttggg agatgtaaga aatgttcttg cagttaaggg ttagtttaca | 1620 |
| atcagccaca ttctaggtag gggcccactt caccgtacta auugggaag ctgtccctca | 1680 |
| ctgttgaatt ttctctaact tcaaggccca tatctgtgaa atgctggcat ttgcacctac | 1740 |
| ctcacagagt gcattgtgag ggttaatgaa ataatgtaca tctggccttg aaaccacctt | 1800 |
| ttattacatg gggtctagaa cttgaccccc ttgagggtgc ttgttccctc tccctgttgg | 1860 |
| tcggtgggtt ggtagtttct acagttgggc agctggttag gtagagggag ttgtcaagtc | 1920 |
| tctgctggcc cagccaaacc ctgtctgaca acctcttggt gaaccttagt acctaaaagg | 1980 |
| aaatctcacc ccatcccaca ccctggagga tttcatctct tgtatatgat gatctggatc | 2040 |
| caccaagact tgttttatgc tcaggtcaa tttcttttt ctttttttt ttttttttc | 2100 |
| ttttctttg agactgggtc tcgctttgtt gcccaggctg gagtggagtg gcgtgatctt | 2160 |
| ggcttactgc agcctttgcc tccccggctc gagcagtcct gcctcagcct ccggagtagc | 2220 |
| tgggaccaca ggttcatgcc accatggcca gccaacttt gcatgttttg tagagatggg | 2280 |
| gtctcacagt gttgcccagg ctggtctcaa actcctgggc tcaggcgatc cacctgtctc | 2340 |
| agcctcccag agtgctggga ttacaattgt gagccaccac gtccagctgg aagggtcaac | 2400 |
| atctttaca ttctgcaagc acatctgcat tttcacccca cccttcccct ccttctccct | 2460 |
| ttttatatcc cattttata tcgatctctt attttacaat aaaactttgc tgccacctgt | 2520 |
| gtgtctgagg ggtg | 2534 |

<210> SEQ ID NO 45
<211> LENGTH: 2534
<212> TYPE: DNA
<213> ORGANISM: Homo sapiens

<400> SEQUENCE: 45

| | |
|---|---|
| cttctcaaaa gtctagagcc accgtccagg gagcaggtag ctgctgggct ccggggacac | 60 |
| tttgcgttcg ggctgggagc gtgctttcca cgacggtgac acgcttccct ggattggcag | 120 |
| ccagactgcc ttccgggtca ctgccatgga ggagccgcag tcagatccta gcgtcgagcc | 180 |
| ccctctgagt caggaaacat tttcagacct atggaaacta cttcctgaaa acaacgttct | 240 |
| gtccccttg ccgtcccaag caatggatga tttgatgctg tccccggacg atattgaaca | 300 |
| atggttcact gaagacccag gtccagatga agctcccaga atgccagagg ctgctccccc | 360 |
| cgtggcccct gcaccagcag ctcctacacc ggcggcccct gcaccagccc ctcctggcc | 420 |
| cctgtcatct tctgtccctt cccagaaaac ctaccagggc agctacggtt tccgtctggg | 480 |

| | |
|---|---|
| cttcttgcat tctgggacag ccaagtctgt gacttgcacg tactccctg ccctcaacaa | 540 |
| gatgttttgc caactggcca agacctgccc tgtgcagctg tgggttgatt ccacacccc | 600 |
| gcccggcacc cgcgtccgcg ccatggccat ctacaagcag tcacagcaca tgacggaggt | 660 |
| tgtgaggcgc tgcccccacc atgagcgctg ctcagatagc gatggtctgg ccctcctca | 720 |
| gcatcttatc cgagtggaag gaaatttgcg tgtggagtat ttggatgaca gaaacacttt | 780 |
| tcgacatagt gtggtggtgc cctatgagcc gcctgaggtt ggctctgact gtaccaccat | 840 |
| ccactacaac tacatgtgta acagttcctg catgggcggc atgaaccgga ggcccatcct | 900 |
| caccatcatc acactggaag actccagtgg taatctactg ggacggaaca gctttgaggt | 960 |
| gcgtgtttgt gcctgtcctg ggagagaccg gcgcacagag aagagaatc tccgcaagaa | 1020 |
| aggggagcct caccacgagc tgccccagg gagcactaag cgagcactgc caacaacac | 1080 |
| cagctcctct ccccagccaa agaagaaacc actggatgga gaatatttca cccttcagat | 1140 |
| ccgtgggcgt gagcgcttcg agatgttccg agagctgaat gaggccttgg aactcaagga | 1200 |
| tgcccaggct gggaaggagc caggggggag cagggctcac tccagccacc tgaagtccaa | 1260 |
| aaagggtcag tctacctccc gccataaaaa actcatgttc aagacagaag ggcctgactc | 1320 |
| agactgacat tctccacttc ttgttcccca ctgacagcct cccacccca tctctccctc | 1380 |
| ccctgccatt ttgggttttg ggtctttgaa cccttgcttg caataggtgt gcgtcagaag | 1440 |
| cacccaggac ttccatttgc tttgtcccgg ggctccactg aacaagttgg cctgcactgg | 1500 |
| tgttttgttg tggggaggag gatggggagt aggacatacc agcttagatt ttaaggtttt | 1560 |
| tactgtgagg gatgtttggg agatgtaaga aatgttcttg cagttaaggg ttagtttaca | 1620 |
| atcagccaca ttctaggtag gggcccactt caccgtacta aaaagggaag ctgtccctca | 1680 |
| ctgttgaatt ttctctaact tcaaggccca tatctgtgaa atgctggcat ttgcacctac | 1740 |
| ctcacagagt gcattgtgag ggttaatgaa ataatgtaca tctggccttg aaaccacctt | 1800 |
| ttattacatg gggtctagaa cttgacccc ttgagggtgc ttgttccctc tccctgttgg | 1860 |
| tcggtgggtt ggtagtttct acagttgggc agctggttag gtagagggag ttgtcaagtc | 1920 |
| tctgctggcc cagccaaacc ctgtctgaca acctcttggt gaaccttagt acctaaaagg | 1980 |
| aaatctcacc ccatcccaca ccctggagga tttcatctct tgtatatgat gatctggatc | 2040 |
| caccaagact tgttttatgc tcagggtcaa ttttctttt cttttttttt tttttttc | 2100 |
| ttttttcttg agactgggtc tcgctttgtt gcccaggctg gagtggagtg gcgtgatctt | 2160 |
| ggcttactgc agcctttgcc tccccggctc gagcagtcct gcctcagcct ccggagtagc | 2220 |
| tgggaccaca ggttcatgcc accatggcca gccaactttt gcatgttttg tagagatggg | 2280 |
| gtctcacagt gttgcccagg ctggtctcaa actcctgggc tcaggcgatc cacctgtctc | 2340 |
| agcctcccag agtgctggga ttacaattgt gagccaccac gtccagctgg aagggtcaac | 2400 |
| atcttttaca ttctgcaagc acatctgcat tttcacccca ccttcccct cttctccct | 2460 |
| ttttatatcc catttttata tcgatctctt attttacaat aaaactttgc tgccacctgt | 2520 |
| gtgtctgagg ggtg | 2534 |

<210> SEQ ID NO 46
<211> LENGTH: 2534
<212> TYPE: DNA
<213> ORGANISM: Homo sapiens

<400> SEQUENCE: 46

| | |
|---|---|
| cttctcaaaa gtctagagcc accgtccagg gagcaggtag ctgctgggct ccggggacac | 60 |

-continued

```
tttgcgttcg ggctgggagc gtgctttcca cgacggtgac acgcttccca aaattggcag    120
ccagactgcc ttccgggtca ctgccatgga ggagccgcag tcagatccta gcgtcgagcc    180
ccctctgagt caggaaacat tttcagacct atggaaacta cttcctgaaa caacgttct    240 gtcccccttg ccgtcccaag caatggatga tttgatgctg tccccggacg atattgaaca    300
atggttcact gaagacccag gtccagatga agctcccaga atgccagagg ctgctccccc    360
cgtggcccct gcaccagcag ctcctacacc ggcggcccct gcaccagccc ctcctggcc    420 cctgtcatct tctgtccctt cccagaaaac ctaccagggc agctacggtt ccgtctggg    480 cttcttgcat tctgggacag ccaagtctgt gacttgcacg tactcccctg ccctcaacaa    540
gatgttttgc caactggcca agacctgccc tgtgcagctg tgggttgatt ccacaccccc    600
gcccggcacc cgcgtccgcg ccatggccat ctacaagcag tcacagcaca tgacggaggt    660
tgtgaggcgc tgccccccacc atgagcgctg ctcagatagc gatggtctgg cccctcctca    720
gcatcttatc cgagtggaag gaaatttgcg tgtggagtat ttggatgaca gaaacacttt    780
tcgacatagt gtggtggtgc cctatgagcc gcctgaggtt ggctctgact gtaccaccat    840
ccactacaac tacatgtgta acagttcctg catgggcggc atgaaccgga ggcccatcct    900
caccatcatc acactggaag actccagtgg taatctactg gacggaaaca gctttgaggt    960 gcgtgttttgt gcctgtcctg ggagagaccg gcgcacagag aagagaaatc tccgcaagaa    1020
aggggagcct caccacgagc tgcccccagg gagcactaag cgagcactgc caacaacac    1080 cagctcctct ccccagccaa agaagaaacc actggatgga gaatatttca cccttcagat    1140
ccgtgggcgt gagcgcttcg agatgttccg agagctgaat gaggccttgg aactcaagga    1200
tgcccaggct gggaaggagc cagggggag cagggctcac tccagccacc tgaagtccaa    1260
aaagggtcag tctacctccc gccataaaaa actcatgttc aagacagaag ggcctgactc    1320
agactgacat tctccacttc ttgttcccca ctgacagcct cccacccca tctctccctc    1380 ccctgccatt ttgggttttg ggtctttgaa cccttgcttg caataggtgt gcgtcagaag    1440
cacccaggac ttccatttgc tttgtcccgg ggctccactg aacaagttgg cctgcactgg    1500
tgttttgttg tggggaggag gatggggagt aggacatacc agcttagatt ttaaggtttt    1560
tactgtgagg gatgtttggg agatgtaaga aatgttcttg cagttaaggg ttagtttaca    1620
atcagccaca ttctaggtag gggcccactt caccgtacta accagggaag ctgtccctca    1680
ctgttgaatt ttctctaact tcaaggccca tatctgtgaa atgctggcat ttgcacctac    1740
ctcacagagt gcattgtgag ggttaatgaa ataatgtaca tctggccttg aaaccacctt    1800
ttattacatg gggtctagaa cttgaccccc ttgagggtgc ttgttccctc tccctgttgg    1860
tcggtgggtt ggtagtttct acagttgggc agctggttag gtagagggag ttgtcaagtc    1920
tctgctggcc cagccaaacc ctgtctgaca acctcttggt gaaccttagt acctaaaagg    1980
aaatctcacc ccatcccaca ccctggagga tttcatctct tgtatatgat gatctggatc    2040
caccaagact tgttttatgc tcagggtcaa tttcttttt cttttttttt tttttttttc    2100
tttttctttg agactgggtc tcgctttgtt gcccaggctg gagtggagtg gcgtgatctt    2160
ggcttactgc agcctttgcc tccccggctc gagcagtcct gcctcagcct ccggagtagc    2220
tgggaccaca ggttcatgcc accatggcca gccaacttttt gcatgttttg tagagatggg    2280
gtctcacagt gttgcccagg ctggtctcaa actcctgggc tcaggcgatc cacctgtctc    2340
agcctcccag agtgctggga ttacaattgt gagccaccac gtccagctgg aagggtcaac    2400
atcttttaca ttctgcaagc acatctgcat tttcacccca cccttcccct ccttctccct    2460
```

| | |
|---|---:|
| ttttatatcc cattttttata tcgatctctt attttacaat aaaactttgc tgccacctgt | 2520 |
| gtgtctgagg ggtg | 2534 |

<210> SEQ ID NO 47
<211> LENGTH: 2534
<212> TYPE: DNA
<213> ORGANISM: Homo sapiens

<400> SEQUENCE: 47

| | |
|---|---:|
| cttctcaaaa gtctagagcc accgtccagg gagcaggtag ctgctgggct ccggggacac | 60 |
| tttgcgttcg ggctgggagc gtgctttcca cgacggtgac acgcttccca aaattggcag | 120 |
| ccagactgcc ttccgggtca ctgccatgga ggagccgcag tcagatccta cgtcgagcc | 180 |
| ccctctgagt caggaaacat ttcagacct atggaaacta cttcctgaaa caacgttct | 240 |
| gtcccccttg ccgtcccaag caatggatga tttgatgctg tccccggacg atattgaaca | 300 |
| atggttcact gaagacccag gtccagatga agctcccaga atgccagagg ctgctccccc | 360 |
| cgtggcccct gcaccagcag ctcctacacc ggcggcccct gcaccagccc cctcctggcc | 420 |
| cctgtcatct tctgtccctt cccagaaaac ctaccgggc agctacggtt ccgtctggg | 480 |
| cttcttgcat tctgggacag ccaagtctgt gacttgcacg tactcccctg ccctcaacaa | 540 |
| gatgttttgc caactggcca agacctgccc tgtgcagctg tgggttgatt ccacacccc | 600 |
| gcccggcacc cgcgtccgcg ccatggccat ctacaagcag tcacagcaca tgacggaggt | 660 |
| tgtgaggcgc tgcccccacc atgagcgctg ctcagatagc gatggtctgg cccctcctca | 720 |
| gcatcttatc cgagtggaag gaaattcg tgtggagtat ttggatgaca gaaacacttt | 780 |
| tcgacatagt gtggtggtgc ctatgagcc gcctgaggtt ggctctgact gtaccaccat | 840 |
| ccactacaac tacatgtgta acagttcctg catgggcggc atgaaccgga ggcccatcct | 900 |
| caccatcatc acactggaag actccagtgg taatctactg gacggaaca gctttgaggt | 960 |
| gcgtgtttgt gcctgtcctg ggagagaccg gcgcacagag aagagaatc tccgcaagaa | 1020 |
| aggggagcct caccacgagc tgcccccagg gagcactaag cgagcactgc caacaacac | 1080 |
| cagctcctct ccccagccaa agaagaaacc actggatgga gaatatttca cccttcagat | 1140 |
| ccgtgggcgt gagcgcttcg agatgttccg agagctgaat gaggccttgg aactcaagga | 1200 |
| tgcccaggct gggaaggagc caggggggag cagggctcac tccagccacc tgaagtccaa | 1260 |
| aaagggtcag tctacctccc gccataaaaa actcatgttc aagacagaag ggcctgactc | 1320 |
| agactgacat tctccacttc ttgttcccca ctgacagcct ccaccccca tctctccctc | 1380 |
| ccctgccatt tgggttttg ggtctttgaa cccttgcttg caataggtgt gcgtcagaag | 1440 |
| cacccaggac ttccatttgc tttgtcccgg ggctccactg aacaagttgg cctgcactgg | 1500 |
| tgttttgttg tggggaggag gatggggagt aggacatacc agcttagatt ttaaggtttt | 1560 |
| tactgtgagg gatgtttggg agatgtaaga aatgttcttg cagttaaggg ttagtttaca | 1620 |
| atcagccaca ttctaggtag gggcccactt caccgtacta aaagggaag ctgtccctca | 1680 |
| ctgttgaatt ttctctaact tcaaggccca tatctgtgaa atgctggcat ttgcacctac | 1740 |
| ctcacagagt gcattgtgag ggttaatgaa ataatgtaca tctggccttg aaaccacctt | 1800 |
| ttattacatg gggtctagaa cttgaccccc ttgagggtgc ttgttccctc tccctgttgg | 1860 |
| tcggtgggtt ggtagtttct acagttgggc agctggttag gtagagggag ttgtcaagtc | 1920 |
| tctgctggcc cagccaaacc ctgtctgaca acctcttggt gaaccttagt acctaaaagg | 1980 |
| aaatctcacc ccatcccaca ccctggagga tttcatctct tgtatatgat gatctggatc | 2040 |

```
caccaagact tgttttatgc tcagggtcaa tttcttttt ctttttttt tttttttttc    2100 tttttctttg agactgggtc tcgctttgtt gcccaggctg gagtggagtg gcgtgatctt    2160
ggcttactgc agcctttgcc tccccggctc gagcagtcct gcctcagcct ccggagtagc    2220
tgggaccaca ggttcatgcc accatggcca gccaactttt gcatgttttg tagagatggg    2280
gtctcacagt gttgcccagg ctggtctcaa actcctgggc tcaggcgatc cacctgtctc    2340
agcctcccag agtgctggga ttacaattgt gagccaccac gtccagctgg aagggtcaac    2400
atcttttaca ttctgcaagc acatctgcat tttcacccca cccttcccct ccttctccct    2460
ttttatatcc cattttata tcgatctctt attttacaat aaaactttgc tgccacctgt    2520
gtgtctgagg ggtg                                                     2534

<210> SEQ ID NO 48
<211> LENGTH: 2534
<212> TYPE: DNA
<213> ORGANISM: Homo sapiens

<400> SEQUENCE: 48
cttctcaaaa gtctagagcc accgtccagg gagcaggtag ctgctgggct ccggggacac      60
tttgcgttcg ggctgggagc gaaatttcca cgacggtgac acgcttccct ggattggcag     120
ccagactgcc ttccgggtca ctgccatgga ggagccgcag tcagatccta gcgtcgagcc     180
ccctctgagt caggaaacat tttcagacct atggaaacta cttcctgaaa caacgttct      240 gtccccttg ccgtcccaag caatggatga tttgatgctg tccccggacg atattgaaca     300
atggttcact gaagacccag gtccagatga agctcccaga atgccagagg ctgctccccc    360
cgtggcccct gcaccagcag ctcctacacc ggcggcccct gcaccagccc cctcctggcc    420
cctgtcatct tctgtccctt cccagaaaac ctaccagggc agctacggtt tccgtctggg    480
cttcttgcat tctgggacag ccaagtctgt gacttgcacg tactcccctg ccctcaacaa    540
gatgttttgc caactggcca agacctgccc tgtgcagctg tgggttgatt ccacaccccc    600
gcccggcacc cgcgtccgcg ccatggccat ctacaagcag tcacagcaca tgacggaggt    660
tgtgaggcgc tgcccccacc atgagcgctg ctcagatagc gatggtctgg cccctcctca    720
gcatcttatc cgagtggaag gaaatttgcg tgtggagtat ttggatgaca gaaacacttt    780
tcgacatagt gtggtggtgc ctatgagcc gcctgaggtt ggctctgact gtaccaccat    840
ccactacaac tacatgtgta acagttcctg catgggcggc atgaaccgga ggcccatcct    900
caccatcatc acactggaag actccagtgg taatctactg ggacggaaca gctttgaggt    960 gcgtgttttgt gcctgtcctg ggagagaccg gcgcacagag aagagaatc tccgcaagaa    1020 agggagcct caccacgagc tgcccccagg gagcactaag cgagcactgc caacaacac     1080 cagctcctct ccccagccaa agaagaaacc actggatgga gaatatttca cccttcagat    1140
ccgtgggcgt gagcgcttcg agatgttccg agagctgaat gaggccttgg aactcaagga    1200
tgcccaggct gggaaggagc agggggaag caggggctcac tccagccacc tgaagtccaa    1260
aaagggtcag tctacctccc gccataaaaa actcatgttc aagacagaag ggcctgactc    1320
agactgacat tctccacttc ttgttcccca ctgacagcct cccaccccca tctctccctc    1380
ccctgccatt tgggttttg ggtctttgaa cccttgcttg caataggtgt gcgtcagaag    1440
cacccaggac ttccatttgc tttgtcccgg ggctccactg aacaagttgg cctgcactgg    1500
tgttttgttg tggggaggag gatggggagt aggacatacc agcttagatt ttaaggttt    1560 tactgtgagg gatgtttggg agatgtaaga aatgttcttg cagttaaggg ttagtttaca    1620
```

```
atcagccaca ttctaggtag gggcccactt caccgtacta accagggaag ctgtccctca    1680
ctgttgaatt ttctctaact tcaaggccca tatctgtgaa atgctggcat ttgcacctac    1740
ctcacagagt gcattgtgag ggttaatgaa ataatgtaca tctggccttg aaaccacctt    1800
ttattacatg gggtctagaa cttgaccccc ttgagggtgc ttgttccctc tccctgttgg    1860
tcggtgggtt ggtagtttct acagttgggc agctggttag gtagagggag ttgtcaagtc    1920
tctgctggcc cagccaaacc ctgtctgaca acctcttggt gaaccttagt acctaaaagg    1980
aaatctcacc ccatcccaca ccctggagga tttcatctct tgtatatgat gatctggatc    2040
caccaagact tgttttatgc tcagggtcaa ttttcttttt cttttttttt ttttttttc     2100 ttttctttg agactgggtc tcgctttgtt gcccaggctg gagtggagtg cgtgatctt      2160 ggcttactgc agcctttgcc tccccggctc gagcagtcct gcctcagcct ccggagtagc    2220
tgggaccaca ggttcatgcc accatggcca gccaacttt  gcatgttttg tagagatggg    2280
gtctcacagt gttgcccagg ctggtctcaa actcctgggc tcaggcgatc cacctgtctc    2340
agcctcccag agtgctggga ttacaattgt gagccaccac gtccagctgg aagggtcaac    2400
atcttttaca ttctgcaagc acatctgcat tttcacccca cccttcccct ccttctccct    2460
ttttatatcc cattttttata tcgatctctt attttacaat aaaactttgc tgccacctgt    2520
gtgtctgagg ggtg                                                      2534
```

<210> SEQ ID NO 49
<211> LENGTH: 145
<212> TYPE: PRT
<213> ORGANISM: Homo sapiens

<400> SEQUENCE: 49

```
Met Lys Phe Asn Pro Phe Val Thr Ser Asp Arg Ser Lys Asn Arg Lys
 1               5                  10                  15

Arg His Phe Asn Ala Pro Ser His Ile Arg Arg Lys Ile Met Ser Ser
            20                  25                  30

Pro Leu Ser Lys Glu Leu Arg Gln Lys Tyr Asn Val Arg Ser Met Pro
        35                  40                  45

Ile Arg Lys Asp Asp Glu Val Gln Val Val Arg Gly His Tyr Lys Gly
    50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Thr Ile Glu Lys Met Gln
    130                 135                 140

Glu
145
```

<210> SEQ ID NO 50
<211> LENGTH: 1327
<212> TYPE: DNA
<213> ORGANISM: Homo sapiens

<400> SEQUENCE: 50

```
cttctcaaaa gtctagagcc accgtccagg gagcaggtag ctgctgggct ccggggacac     60
```

```
tttgcgttcg ggctgggagc gtgctttcca cgacggtgac acgcttccct ggattggcag    120
ccagactgcc ttccgggtca ctgccatgga ggagccgcag tcagatccta gcgtcgagcc    180
ccctctgagt caggaaacat tttcagacct atggaaacta cttcctgaaa caacgttct     240
gtcccccttg ccgtcccaag caatggatga tttgatgctg tccccggacg atattgaaca    300
atggttcact gaagacccag gtccagatga agctcccaga tgccagaggc tgctcccccc    360
cgtggcccct gcaccagcag ctcctacacc ggcggcccct gcaccagccc ctcctggcc     420
cctgtcatct tctgtccctt cccagaaaac ctaccagggc agctacggtt ccgtctggg     480
cttcttgcat tctgggacag ccaagtctgt gacttgcacg tactcccctg ccctcaacaa    540
gatgttttgc caactggcca agacctgccc tgtgcagctg tgggttgatt ccacaccccc    600
gcccggcacc cgcgtccgcg ccatggccat ctacaagcag tcacagcaca tgacggaggt    660
tgtgaggcgc tgccccccac catgagcgct gctcagatag cgatggtctg ccccctcctca   720
gcatcttatc cgagtggaag gaaatttgcg tgtggagtat ttggatgaca gaaacacttt    780
tcgacatagt gtggtggtgc cctatgagcc gcctgaggtt ggctctgact gtaccaccat    840
ccactacaac tacatgtgta acagttcctg catgggcggc atgaaccgga ggcccatcct    900
caccatcatc acactggaag actccagtgg taatctactg ggacggaaca gctttgaggt    960
gcgtgttttgt gcctgtcctg ggagagaccg gcgcacagag aagagaatc tccgcaagaa   1020
agggagcct caccacgagc tgcccccagg gagcactaag cgagcactgc caacaacac    1080
cagctcctct ccccagccaa agaagaaacc actggatgga gaatatttca cccttcagat   1140
ccgtgggcgt gagcgcttcg agatgttccg agagctgaat gaggccttgg aactcaagga   1200
tgcccaggct gggaaggagc caggggggag cagggctcac tccagccacc tgaagtccaa   1260
aaagggtcag tctacctccc gccataaaaa actcatgttc aagacagaag ggcctgactc   1320
agactga                                                              1327
```

<210> SEQ ID NO 51
<211> LENGTH: 710
<212> TYPE: PRT
<213> ORGANISM: Homo sapiens

<400> SEQUENCE: 51

```
Met Val Lys Leu Ala Lys Ala Gly Lys Asn Gln Gly Asp Pro Lys Lys
 1               5                   10                  15

Met Ala Pro Pro Lys Glu Val Glu Glu Asp Ser Glu Asp Glu Glu
                20                  25                  30

Met Ser Glu Asp Glu Glu Asp Ser Ser Gly Glu Glu Val Val Ile
            35                  40                  45

Pro Gln Lys Lys Gly Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
    130                 135                 140

Ser Asp Glu Glu Glu Asp Asp Asp Ser Glu Glu Asp Glu Glu Asp Asp
```

```
            145                 150                 155                 160
Glu Asp Glu Asp Glu Asp Glu Asp Glu Ile Glu Pro Ala Ala Met Lys
                    165                 170                 175
Ala Ala Ala Ala Ala Pro Ala Ser Glu Asp Glu Asp Asp Glu Asp Asp
                    180                 185                 190
Glu Asp Asp Glu Asp Asp Asp Asp Glu Glu Asp Asp Ser Glu Glu
                    195                 200                 205
Glu Ala Met Glu Thr Thr Pro Ala Lys Gly Lys Lys Ala Ala Lys Val
                    210                 215                 220
Val Pro Val Lys Ala Lys Asn Val Ala Glu Asp Glu Asp Glu Glu Glu
225                 230                 235                 240
Asp Asp Glu Asp Glu Asp Asp Asp Glu Asp Asp Glu Asp Asp
                    245                 250                 255
Asp Asp Glu Asp Asp Glu Glu Glu Glu Glu Glu Glu Glu Glu Pro
                    260                 265                 270
Val Lys Glu Ala Pro Gly Lys Arg Lys Lys Glu Met Ala Lys Gln Lys
                    275                 280                 285
Ala Ala Pro Glu Ala Lys Lys Gln Lys Val Glu Gly Thr Glu Pro Thr
                    290                 295                 300
Thr Ala Phe Asn Leu Phe Val Gly Asn Leu Asn Phe Asn Lys Ser Ala
305                 310                 315                 320
Pro Glu Leu Lys Thr Gly Ile Ser Asp Val Phe Ala Lys Asn Asp Leu
                    325                 330                 335
Ala Val Val Asp Val Arg Ile Gly Met Thr Arg Lys Phe Gly Tyr Val
                    340                 345                 350
Asp Phe Glu Ser Ala Glu Asp Leu Glu Lys Ala Leu Glu Leu Thr Gly
                    355                 360                 365
Leu Lys Val Phe Gly Asn Glu Ile Lys Leu Glu Lys Pro Lys Gly Lys
                    370                 375                 380
Asp Ser Lys Lys Glu Arg Asp Ala Arg Thr Leu Leu Ala Lys Asn Leu
385                 390                 395                 400
Pro Tyr Lys Val Thr Gln Asp Glu Leu Lys Glu Val Phe Glu Asp Ala
                    405                 410                 415
Ala Glu Ile Arg Leu Val Ser Lys Asp Gly Lys Ser Lys Gly Ile Ala
                    420                 425                 430
Tyr Ile Glu Phe Lys Thr Glu Ala Asp Ala Glu Lys Thr Phe Glu Glu
                    435                 440                 445
Lys Gln Gly Thr Glu Ile Asp Gly Arg Ser Ile Ser Leu Tyr Tyr Thr
                    450                 455                 460
Gly Glu Lys Gly Gln Asn Gln Asp Tyr Arg Gly Gly Lys Asn Ser Thr
465                 470                 475                 480
Trp Ser Gly Glu Ser Lys Thr Leu Val Leu Ser Asn Leu Ser Tyr Ser
                    485                 490                 495
Ala Thr Glu Glu Thr Leu Gln Glu Val Phe Glu Lys Ala Thr Phe Ile
                    500                 505                 510
Lys Val Pro Gln Asn Gln Asn Gly Lys Ser Lys Gly Tyr Ala Phe Ile
                    515                 520                 525
Glu Phe Ala Ser Phe Glu Asp Ala Lys Glu Ala Leu Asn Ser Cys Asn
                    530                 535                 540
Lys Arg Glu Ile Glu Gly Arg Ala Ile Arg Leu Glu Leu Gln Gly Pro
545                 550                 555                 560
Arg Gly Ser Pro Asn Ala Arg Ser Gln Pro Ser Lys Thr Leu Phe Val
                    565                 570                 575
```

```
Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
        595                 600                 605

Ser Lys Gly Phe Gly Phe Val Asp Phe Asn Ser Glu Glu Asp Ala Lys
    610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
                645                 650                 655

Gly Gly Gly Arg Gly Gly Phe Gly Gly Arg Gly Gly Arg Gly Gly
            660                 665                 670

Arg Gly Gly Phe Gly Gly Arg Gly Arg Gly Gly Phe Gly Gly Arg Gly
            675                 680                 685

Gly Phe Arg Gly Gly Arg Gly Gly Gly Gly Asp His Lys Pro Gln Gly
        690                 695                 700

Lys Lys Thr Lys Phe Glu
705                 710

<210> SEQ ID NO 52
<211> LENGTH: 1257
<212> TYPE: DNA
<213> ORGANISM: Homo sapiens

<400> SEQUENCE: 52
ggctgggagc gtgctttcca cgacggtgac acgcttccct ggattggcag ccagactgcc      60
ttccgggtca ctgccatgga ggagccgcag tcagatccta gcgtcgagcc ccctctgagt     120
caggaaacat tttcagacct atggaaacta cttcctgaaa caacgttctg tgtccccttg     180
ccgtcccaag caatggatga tttgatgctg tccccggacg atattgaaca atggttcact     240
gaagacccag gtccagatga agctcccaga atgccagagg ctgctccccc cgtggcccct     300
gcaccagcag ctcctacacc ggcggcccct gcaccagccc cctcctggcc cctgtcatct     360
tctgtccctt cccagaaaac ctaccagggc agctacggtt tccgtctggg cttcttgcat     420
tctgggacag ccaagtctgt gacttgcacg tactcccctg ccctcaacaa gatgttttgc     480
caactggcca agacctgccc tgtgcagctg tgggttgatt ccacacccc gcccggcacc     540 cgcgtccgcg ccatggccat ctacaagcag tcacagcaca tgacggaggt tgtgaggcgc     600
tgcccccacc atgagcgctg ctcagatagc gatggtctgg cccctcctca gcatcttatc     660
cgagtggaag gaaatttgcg tgtggagtat ttggatgaca gaaacacttt tcgacatagt     720
gtggtggtgc cctatgagcc gcctgaggtt ggctctgact gtaccaccat ccactacaac     780
tacatgtgta acagttcctg catgggcggc atgaaccgga ggcccatcct caccatcatc     840
acactggaag actccagtgg taatctactg ggacggaaca gctttgaggt gcgtgttttgt     900 gcctgtcctg ggagagaccg gcgcacagag aagagaatc tccgcaagaa agggggagcct     960 caccacgagc tgcccccagg gagcactaag cgagcactgc caacaacac cagctcctct    1020 ccccagccaa agaagaaacc actggatgga gaatattttca cccttcagat ccgtgggcgt    1080
gagcgcttcg agatgttccg agagctgaat gaggccttgg aactcaagga tgcccaggct    1140
gggaaggagc cagggggggag cagggctcac tccagccacc tgaagtccaa aaagggtcag    1200
tctacctccc gccataaaaa actcatgttc aagacagaag ggcctgactc agactga       1257

<210> SEQ ID NO 53
<211> LENGTH: 1257
```

```
<212> TYPE: DNA
<213> ORGANISM: Homo sapiens

<400> SEQUENCE: 53
ggctgggagc gtgctttcca cgacggtgac acgcttccca aaattggcag ccagactgcc      60
ttccgggtca ctgccatgga ggagccgcag tcagatccta gcgtcgagcc ccctctgagt     120
caggaaacat ttcagacct atggaaacta cttcctgaaa caacgttct gtccccttg        180
ccgtcccaag caatggatga tttgatgctg tccccggacg atattgaaca atggttcact     240
gaagacccag gtccagatga agctcccaga atgccagagg ctgctccccc cgtggcccct     300
gcaccagcag ctcctacacc ggcggccct gcaccagccc cctcctggcc cctgtcatct      360
tctgtcccctt cccagaaaac ctaccagggc agctacggtt ccgtctggg cttcttgcat     420
tctgggacag ccaagtctgt gacttgcacg tactcccctg ccctcaacaa gatgttttgc     480
caactggcca agacctgccc tgtgcagctg tgggttgatt ccacacccc gcccggcacc      540
cgcgtccgcg ccatggccat ctacaagcag tcacagcaca tgacgaggt tgtgaggcgc      600
tgccccacc atgagcgctg ctcagatagc gatggtctgg ccctcctca gcatcttatc       660
cgagtggaag gaaatttgcg tgtggagtat ttggatgaca gaaacacttt tcgacatagt     720
gtggtggtgc cctatgagcc gcctgaggtt ggctctgact gtaccaccat ccactacaac     780
tacatgtgta acgttcctg catgggcggc atgaaccgga ggcccatcct caccatcatc      840
acactggaag actccagtgg taatctactg ggacggaaca gctttgaggt gcgtgtttgt    900
gcctgtcctg ggagagaccg gcgcacagag aagagaatc tccgcaagaa aggggagcct    960
caccacgagc tgcccccagg gagcactaag cgagcactgc caacaacac cagctcctct   1020
ccccagccaa agaagaaacc actggatgga gaatatttca cccttcagat ccgtgggcgt   1080
gagcgcttcg agatgttccg agagctgaat gaggccttgg aactcaagga tgcccaggct   1140
gggaaggagc agggggggag cagggctcac tccagccacc tgaagtccaa aaagggtcag   1200
tctacctccc gccataaaaa actcatgttc aagacagaag ggcctgactc agactga      1257

<210> SEQ ID NO 54
<211> LENGTH: 393
<212> TYPE: PRT
<213> ORGANISM: Homo sapiens

<400> SEQUENCE: 54

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
```

```
                    130             135             140
Leu Trp Val Asp Ser Thr Pro Pro Gly Thr Arg Val Arg Ala Met
145                 150             155             160

Ala Ile Tyr Lys Gln Ser Gln His Met Thr Glu Val Val Arg Arg Cys
                165             170             175

Pro His His Glu Arg Cys Ser Asp Ser Asp Gly Leu Ala Pro Pro Gln
            180             185             190

His Leu Ile Arg Val Glu Gly Asn Leu Arg Val Glu Tyr Leu Asp Asp
        195             200             205

Arg Asn Thr Phe Arg His Ser Val Val Val Pro Tyr Glu Pro Pro Glu
    210             215             220

Val Gly Ser Asp Cys Thr Thr Ile His Tyr Asn Tyr Met Cys Asn Ser
225             230             235             240

Ser Cys Met Gly Gly Met Asn Arg Arg Pro Ile Leu Thr Ile Ile Thr
            245             250             255

Leu Glu Asp Ser Ser Gly Asn Leu Leu Gly Arg Asn Ser Phe Glu Val
            260             265             270

Arg Val Cys Ala Cys Pro Gly Arg Asp Arg Arg Thr Glu Glu Glu Asn
        275             280             285

Leu Arg Lys Lys Gly Glu Pro His His Glu Leu Pro Pro Gly Ser Thr
    290             295             300

Lys Arg Ala Leu Pro Asn Asn Thr Ser Ser Ser Pro Gln Pro Lys Lys
305             310             315             320

Lys Pro Leu Asp Gly Glu Tyr Phe Thr Leu Gln Ile Arg Gly Arg Glu
            325             330             335

Arg Phe Glu Met Phe Arg Glu Leu Asn Glu Ala Leu Glu Leu Lys Asp
            340             345             350

Ala Gln Ala Gly Lys Glu Pro Gly Gly Ser Arg Ala His Ser Ser His
        355             360             365

Leu Lys Ser Lys Lys Gly Gln Ser Thr Ser Arg His Lys Lys Leu Met
    370             375             380

Phe Lys Thr Glu Gly Pro Asp Ser Asp
385             390
```

OLIGONUCLEOTIDES WHICH INHIBIT P53 INDUCTION IN RESPONSE TO CELLULAR STRESS

CROSS REFERENCE TO PRIOR APPLICATIONS

This is a U.S. National Phase application under 35 U.S.C. §371 of International Patent Application No. PCT/US2011/022930, filed Jan. 28, 2011, and claims the benefit of U.S. Provisional Patent Application No. 61/299,630, filed Jan. 29, 2010, both of which are incorporated by reference herein in their entirety. The International Application published in English on Aug. 4, 2011 as WO 2011/094546 under PCT Article 21(2).

STATEMENT REGARDING FEDERALLY SPONSORED RESEARCH OR DEVELOPMENT

The research leading to the present invention was supported, in part, by NIH grants R37ES05777 and P30CA21765. Accordingly, the U.S. government has certain rights in the invention.

FIELD OF THE INVENTION

The present invention relates to modulating the activity of p53 tumor suppressor protein by affecting p53 translational regulation and its use for minimizing the negative effects of cellular stresses. More specifically, the invention relates to novel oligonucleotides which comprise p53 5'-UTR sequence TCCCTGG (SEQ ID NO: 1) or the complementary p53 3'-UTR sequence CCAGGGA (SEQ ID NO: 2) and their use for such therapeutic applications as protection of normal tissues from the toxicities of chemical or radiation exposure; reducing tissue damage in hypoxia-reperfusion injury, neurodegenerative disorders, oxidative stress, injuries, hyperthermia; preventing aging; preservation of tissues and organs prior to transplanting, etc.

BACKGROUND OF THE INVENTION

The p53 gene is one of the most studied and well-known genes. p53 plays a key role in cellular stress response mechanisms by converting a variety of different stimuli, for example, DNA damage, deregulation of transcription or replication, and oncogene transformation, into cell growth arrest or apoptosis (Kastan et al., Cancer Res 1991; 51:6304-6311; Kastan et al., Cell 1992; 71:587-597; Vogelstein et al., Nature 2000; 408:307-310; Vousden et al., Nat Rev Cancer 2002; 2:594-604; Giaccia and Kastan, Genes & Development 1998; 12:2973-2983.

The p53 protein is active as a homo-tetramer and exerts its tumor suppressor function mainly as a transcription factor that affects G1 and G2 cell cycle arrest and/or apoptosis (see, e.g., Donehower and Bradley, Biochim Biophys Acta., 1993, 1155(2):181-205; Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31). The p53-mediated G1 arrest is its best characterized activity and involves transcriptional activation of the downstream gene p21 WAF1/CIP1/SDI1 (Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31). Other downstream effector genes for p53-mediated G1 arrest may exist, since p21−/− mouse embryonic fibroblasts do not show complete abrogation of GI arrest after DNA damage (Brugarolas et al., Nature, 1995, 377(6549): 552-7; Deng et al., Cell, 1995, 82(4):675-84). The G2/M effects of p53 involve, at least in part, induction of 14-3-3σ (Hermeking et al., Mol. Cell, 1997, 1(1):3-11).

The mechanisms for apoptosis induction and their relative importance remain less clear at present. In certain settings p53 clearly induces pro-apoptotic genes. These include BAX and Fas/APO1 (Miyashita and Reed, Cell, 1995, 80(2):293-9; Owen-Schaub et al., Mol. Cell. Biol., 1995, 15(6):3032-40) neither of which, however, is an absolute requirement for p53-induced apoptosis (Fuchs et al., Cancer Res., 1997, 57(13):2550-4). Recently, many more genes have been identified that are induced directly or indirectly during p53-mediated apoptosis (Polyak et al., Nature, 1997, 389(6648):300-5), but the essential genes for p53-induced apoptosis still have to be determined. Transcriptional repression of anti-apoptotic genes, such as bcl-2, may play a role (Haldar et al., Cancer Res., 1994, 54(8):2095-7; Miyashita et al., Oncogene, 1994, 9(6):1799-805) and other non-transcriptional mechanisms may be important as well (Caelles et al., Nature, 1994, 370 (6486):220-3; Haupt et al., Nature 1997; 387:296-299).

Several upstream signals activate p53. These include DNA damage, hypoxia and critically low ribonucleoside triphosphate pools (Kastan et al., Cancer Res. 1991; 51:6304-6311; Graeber et al., Nature, 1996, 379(6560):88-91; Linke et al., Genes Dev., 1996, 10(8):934-47). Once activated, p53 induces either cell cycle arrest or apoptosis, depending on several factors such as the amount of DNA damage, cell type and cellular milieu, e.g., presence or absence of growth factors (Donehower and Bradley, Biochim Biophys Acta., 1993, 1155(2):181-205; Haffner and Oren, Curr. Opin. Genet. Dev., 1995, 5(1):84-90; Gottlieb and Oren, Biochim. Biophys. Acta., 1996, 1287(2-3):77-102; Ko and Prives, Genes Dev., 1996, 10(9):1054-72; Hansen and Oren, Curr. Opin. Genet. Dev., 1997, 7(1):46-51; Levine, Cell, 1997, 88(3):323-31); Giaccia and Kastan, Genes & Development 1998; 12:2973-2983.

Cancer cells show decreased fidelity in replicating their DNA, often resulting in DNA damage, and tumor masses have inadequate neovascularization leading to ribonucleoside triphosphate or oxygen deprivation, all upstream signals that activate p53. In view of p53's capability to induce cell cycle arrest or apoptosis under these conditions it is not surprising that absent or significantly reduced activity of the tumor suppressor protein p53 is a characteristic of more than half of all human cancers (Harris and Hollstein, N. Engl J. Med., 1993, 329(18):1318-27; Greenblatt et al., Cancer Res., 1994, 54(18):4855-78). In the majority of cancers, p53 inactivation is caused by missense mutations in one p53 allele, often with concomitant loss-of-heterozygosity (Michalovitz et al., J. Cell. Biochem., 1991, 45(1):22-9; Vogelstein and Kinzler, Cell, 1992, 70(4):523-6; Donehower and Bradley, Biochim. Biophys. Acta., 1993, 1155(2):181-205; Levine, Cell, 1997, 88(3):323-31). These mutations affect almost exclusively the core DNA-binding domain of p53 that is responsible for making contacts with p53 DNA-binding sites, while mutations in the N-terminal transactivation domain or the C-terminal tetramerization domain are extremely rare (Beroud and Soussi, Nucleic Acids Res., 1998, 26(1):200-4; Cariello et al., Nucleic Acids Res., 1998, 26(1):198-9; Hainaut et al., P., Nucleic Acids Res. 1998; 26:205-213).

Contrary to wild-type p53, p53 cancer mutants have a long half-life and accumulate to high levels in cancer cells (Donehower and Bradley, Biochim Biophys Acta., 1993, 1155(2):

181-205; Lowe, Curr. Opin. Oncol., 1995, 7(6):547-53). This may be explained by their inability to activate the mdm-2 gene (Lane and Hall, Trends Biochem. Sci., 1997, 22(10): 372-4), since mdm-2 induces degradation of p53 via the ubiquitin pathway as part of a negative feedback loop (Haupt et al., Nature 1997; 387:296-299; Kubbutat et al., Nature 1997; 387:299-303). The unusually high frequency of p53 missense mutations in human cancers (as opposed to mutations resulting in truncated proteins) is explained by their dominant-negative effect that depends on the intact C-terminal tetramerization domain. The C-terminus allows p53 cancer mutants to form hetero-tetramers with wild-type p53 (Milner and Medcalf, Cell, 1991, 65(5):765-74), thus reducing, or even abrogating, the activity of wild-type p53 protein (Michalovitz et al., J. Cell. Biochem., 1991, 45(1):22-9; Vogelstein and Kinzler, Cell, 1992, 70(4):523-6; Ko and Prives, Genes Dev., 1996, 10(9):1054-72). In addition, there is evidence that at least some of the same missense mutations may confer a gain-of-function (Gottlieb and Oren, Biochim. Biophys. Acta., 1996, 1287(2-3):77-102; Ko and Prives, Genes Dev., 1996, 10(9):1054-72; Levine, Cell, 1997, 88(3):323-31).

p53 imparts sensitivity to normal tissues subjected to genotoxic stress. For example, p53-mediated apoptosis causes side effects of radiation therapy and chemotherapy such as severe damage to the lymphoid and hematopoietic system and intestinal epithelia, which limit the effectiveness of these therapies. [Gudkov and Komarova, Nat. Rev. Cancer, 2003, 3:117-129; Westphal et al., Cancer Research, 1998]. Other side effects, like hair loss, also are p53 mediated and further detract from cancer therapies (Botchkarev et al., Cancer Res., 2000, 60:5002-5006).

In summary, p53 has a dual role in cancer therapy. On one hand, p53 acts as a tumor suppressor by mediating apoptosis and growth arrest in response to a variety of stresses and controlling cellular senescence. On the other hand, p53 is responsible for severe damage to normal tissues during cancer therapies.

The damage caused by p53 to normal tissues makes p53 a potential target for therapeutic suppression. Since more than 50% of human tumors lack functional p53, suppression of p53 would not affect the efficacy of a treatment for such tumors, and would protect normal p53-containing tissues (Komarova et al., Seminars in Cancer Biology 1998; 8(5): 389-400). It has been also recognized that therapeutic p53 inhibition should be reversible as long-term p53 inactivation can significantly increase the risk of cancer. Komarov et al. (Science, 1999; 285:1733-1737) developed a cell-based screen aimed at identifying compounds capable of inhibiting p53-mediated apoptosis from a library of 10 000 synthetic chemicals. In this screen, they have identified a stable water-soluble p53-inhibitor pifithrin-α (PFT-α), which suppressed p53-dependent apoptosis and protected mice from the lethal genotoxic stress associated with cancer treatment without promoting the formation of tumors. See also, e.g., U.S. Pat. Nos. 7,012,087; 6,593,353 and 6,420,136. PFT-α does not block p53 induction and the mechanism by which it functions downstream of p53 has not been elucidated yet. Further, it has been recently shown that PFT-α protects cells from DNA damage-induced apoptosis also by a p53-independent mechanism (Sohn et al., Cell Death and Differentiation (2009), 1-10). Such complexity of the mechanism of action makes PFT-α less attractive as a p53 inhibitory therapeutic, since all possible side effects cannot be easily assessed. Thus, novel compounds are needed which would selectively and reversibly inhibit p53 activity in normal tissues during treatment of p53-deficient tumors, and thereby protect normal tissues.

The adverse effects of p53 activity on an organism are not limited to cancer or cancer therapies. p53 is activated as a consequence of a variety of stresses associated with injuries (e.g., burns), naturally occurring diseases (e.g., fever, and conditions of local hypoxia associated with a blocked blood supply, stroke, and ischemia) and cell aging (e.g., senescence of fibroblasts). p53 inhibition, therefore, also can be therapeutically effective, for example, in reducing or eliminating p53-dependent neuronal death in the central nervous system (e.g., after brain and spinal cord injury), reducing or eliminating neuronal damage during seizures, suppressing tissue aging, or preservation of tissues and organs prior to transplantation.

p53 regulation has also been shown to affect the pathogenesis of neurodegenerative diseases. For example, as shown by Bae et al. (Neuron 2005; 47:29-41), (i) p53 levels are increased in the brains of mutant huntingtin protein (mHtt) transgenic mice (mHtt-Tg) and Huntington's Disease (HD) patients and (ii) upregulation of p53 transcriptional activity and nuclear p53 levels by mHtt leads to mitochondrial depolarization and cytotoxicity in neuronal cell cultures, revealing a role for p53 regulation in the development of HD. Reduction or elimination of p53 suppresses this neurodegenerative effect. Thus, p53 regulation can be beneficial for amelioration of HD and other neurodegenerative diseases.

p53 has a short half-life, and, accordingly, is continuously synthesized and degraded in the cell. However, when a cell is subjected to stress (e.g., (a) DNA damage, such as damage caused by ionizing irradiation (IR) or UV (ultraviolet) radiation, cell mutations, chemotherapy, and radiation therapy; (b) hyperthermia; and (c) deregulation of microtubules caused by some chemotherapeutic drugs, e.g., treatment using taxol or Vinca alkaloids), the intracellular levels of functional p53 protein increase (Canman et al., Oncogene 1998; 16:957-966; Canman et al., Genes & Dev. 1995; 9:600-611; Kuerbitz et al., Proc Natl Acad Sci 1992; 89:7491-7495). The increases in p53 protein levels are dependent on the ATM protein kinase after ionizing irradiation (IR) (Kastan et al., Cell 1992; 71:587-597) and on the ATR protein kinase after UV irradiation and many other types of cellular stress (Tibbetts et al., Genes & Development 1999; 13:152-157; Hammond et al., Mol Cell Biol. 2002; 22:1834-1843; Wright et al., Pro Natl Acad Sci U.S.A. 1998; 95:7445-7450).

There is a measurable increase in the half-life of p53 protein after DNA damage (Maltzman et al., Molec and Cell Biol 1984; 4(9):1689-1694; Price et al., Oncogene 1993; 8:3055-3062; Maki et al., Mol. Cell Biol. 1997; 17:355-363) and the increases in cellular p53 protein levels have largely been attributed to this change in half-life. p53 protein is normally a very short-lived cellular protein with rapid proteosomal degradation in unperturbed cells. The HDM2 protein (MDM2 in mice) directly binds to p53 protein (Momand et al., Cell 1992; 69:1237-1245; Oliner et al., Nature 1993; 362:857-860) and functions as an E3 ubiquitin ligase to facilitate the degradation of p53 (Fang et al., S., J Biol Chem 2000; 275:8945-8951; Honda et al., FEBS Letters 1997; 420:25-27; Haupt et al., Nature 1997; 387:296-299; Kubbutat et al., Nature 1997; 387:299-303). Post-translational modifications of HDM2 and p53 after DNA damage appear to inhibit the ability of HDM2 to bind to p53 (Mayo et al., Cancer Research 1997; 57:5013-5016; Khosravi et al., PNAS 1999; 96:14973-14977; Maya et al., Genes & Development 2001; 15:1067-1077; Shieh et al., Cell 1997; 91:325-334; Ashcroft et al., Molecular & Cellular Biology 1999; 19:1751-1758), thus decreasing the proteosomal degradation of p53 protein and increasing cellular levels of the protein. Similarly, induction of the ARF tumor suppressor by oncogenes and other cellular signals leads to increases in p53 protein levels by ARF protein binding to HDM2 and inhibiting HDM2-mediated degradation of p53 (Palmero et al., Nature 1999; 395:127; Kamijo et al., Proc. Natl. Acad. Sci. U.S.A 1998; 95:8292-8297; Sherr et al., Curr. Opin. Genet. Dev. 2000; 10:94-99; Pomerantz et al., Cell 1998; 92:713-723; Stott et al., EMBO J. 1998; 17:5001-5014). Thus, cells with overexpressed HDM2 or inactive ARF are similar to cells containing mutated p53 genes in that normal p53 regulation is lacking.

It has been recently established that translational regulation also contributes to p53 induction after DNA damage (Takagi et al., Cell, 2005, 123(1): 49-63). In the initial reports of p53 induction after ionizing irradiation, the protein synthesis inhibitor cycloheximide was shown to block p53 induction and marked increases in labeling of p53 protein with [$^{35}$S]-methionine were noted early after treatment (Kastan et al., Cancer Res 1991; 51:6304-6311; Kastan et al., Cell 1992; 71:587-597). Subsequently, a translation suppressor element was reported in the 3'-UTR of the p53 mRNA (Fu et al., EMBO J. 1997; 16:4117-4125; Fu et al., Oncogene 1999; 18:6419-6424; Fu et al., EMBO J. 1996; 15:4392-4401) and a stem loop structure was predicted in the 5'-UTR of the murine p53 gene (Mosner et al., EMBO J. 1995; 14:4442-4449). Interestingly, p53 was suggested to negatively regulate its own translation by direct binding of p53 protein to this 5'-UTR stem loop structure (Mosner et al., EMBO J. 1995; 14:4442-4449). Two other proteins have also been reported to modulate p53 translation: thymidylate synthase suppresses p53 translation by binding to the coding sequence of p53 mRNA (Chu et al., Mol. Cell Biol. 1999; 19:1582-1594; Ju et al., Proc. Natl. Acad. Sci. U.S.A 1999; 96:3769-3774) and HuR (Hu antigen R) enhances the translation efficiency of p53 after ultraviolet irradiation by binding to an AU-rich sequence at the 3'-UTR of p53 mRNA (Mazan-Mamczarz et al., Proc. Natl. Acad. Sci. U.S.A 2003; 100:8354-8359).

Screens for proteins that specifically bind to a 5'-UTR of p53 mRNA conducted by the present inventors have identified three proteins, Ribosomal Protein L26 (RPL26) (e.g., human RPL26 protein having GenBank Accession No. NP_000978) (SEQ ID NO: 49), nucleolin ("NCL") (e.g., human nucleolin protein having GenBank Accession No. NP_005372) (SEQ ID NO: 51), and p53 protein itself (e.g., human p53 protein having GenBank Accession No. NP_000537) (SEQ ID NO: 54), that bind to the 5'UTR of p53 both in vitro and in cells (see PCT Publication No. WO 2007/041213 and Takagi et al., Cell, 2005, 123(1): 49-63). Manipulations of RPL26 and nucleolin demonstrated that they modulate p53 protein levels and affect p53 induction after DNA damage. Increased levels of RPL26 enhance both basal and DNA damage-induced translation of p53 mRNA in vitro and in cells and enhance cellular functions dependent on p53, such as cell cycle arrest and apoptosis. The effects of RPL26 on p53 translation require the presence of the 5'-UTR. Reduction of RPL26 levels by siRNA inhibit these p53-dependent responses, thus demonstrating a role for endogenous RPL26 in DNA damage responses. Nucleolin has the opposite effects on p53, with overexpression reducing basal and DNA damage-induced translation and inhibition of nucleolin enhancing translation. Taken together, RPL26 and nucleolin appear to compete with each other to regulate p53 synthesis through binding to a 5'-UTR of p53 mRNA.

It has been recently reported (Ofir-Rosenfeld et al., Mol. Cell., 2008, 32: 180-189) that translational regulation of p53 also involves protein Mdm2 As noted above, Mdm2 regulates p53 protein by promoting its proteasome-mediated degradation, and Mdm2 and p53 engage in an autoregulatory feedback loop that maintains low p53 activity in nonstressed cells. As shown by Ofir-Rosenfeld et al., Mdm2 also regulates p53 levels by targeting RPL26. Mdm2 binds RPL26 and drives its polyubiquitylation and proteasomal degradation. In addition, the binding of Mdm2 to RPL26 attenuates the association of RPL26 with p53 mRNA and represses RPL26-mediated augmentation of p53 protein synthesis. It is hypothesized that under nonstressed conditions, both mechanisms help maintain low cellular p53 levels by constitutively tuning down p53 translation, while, in response to genotoxic stress, the inhibitory effect of Mdm2 on RPL26 is attenuated, enabling a rapid increase in p53 synthesis.

Currently, there are two recognized forms of eukaryotic translation, cap-dependent translation and cap-independent translation (Hellen and Sarnow, 2001, Genes Dev. 15: 1593-1612). The recognition of the 7-methylguanosine cap located at the 5'-end of eukaryotic mRNAs by the eukaryotic initiation factor eIF4E, which is part of a greater initiation complex eIF4F, is a crucial step of cap-dependent protein translation (Gingras et al., 1999, Annu. Rev. Biochem. Allied Res. 68: 913-963). During cellular stress, such as heat shock (Vries et al., 1997, J. Biol. Chem. 272: 32779-32784) or hypoxia (Tinton and Buc-Calderon, 1999, FEBS Lett. 446: 55-59), 4E-BP1 is dephosphorylated and cap-dependent protein translation is impaired. In these instances, cap-independent protein translation initiation, which does not require the presence of the 7-methylguanosine cap or its binding factor, eIF4E, is used to synthesize the needed proteins (Vagner et al., 2001, EMBO J., 2: 893-898). Cap-independent translation is usually mediated by a complex structural element at the 5'-UTR of the mRNA called an internal ribosome entry site (IRES). With the help of eIF4G and other translation initiation factors, IRESs are capable of recruiting the 40S ribosomal subunit and initiating translation without the need for the initiation factor eIF4E. Recent findings show that p53 can be translated in a cap-independent manner, e.g., in response to treatment with the DNA-damaging agent etoposide (Yang et al., 2006, Oncogene 25: 4613-4619; Ray et al., 2006, EMBO Rep. 7: 404-410). Deletion analysis demonstrated that most of the p53 IRES activity is contained within the first 70 nucleotides of the p53 5'-UTR (Yang et al., 2006, Oncogene 25: 4613-4619).

Taken together, both the 5'- and 3'-untranslated regions (UTR) of the p53 mRNA appear to be sites of p53 translational regulation in response to stress through various trans-acting factors.

SUMMARY OF THE INVENTION

As specified in the Background Section, above, there is a great need in the art to develop new agents capable of affecting the function of p53 protein. The present invention addresses this and other needs by providing novel oligonucleotides which are specific inhibitors of p53 induction.

The present invention is based on an unexpected discovery that short oligonucleotides which comprise p53 5'-untranslated region (5' UTR) sequence TCCCTGG (SEQ ID NO: 1) or the complementary p53 3'-UTR sequence CCAGGGA (SEQ ID NO: 2) are able to specifically decrease the level of p53 protein or inhibit p53 protein induction in response to various cellular stresses.

Thus, in one aspect, the present invention provides an isolated oligonucleotide which ranges from about 7 to about 50 nucleotides in length and comprises the sequence TCCCTGG (SEQ ID NO: 1) or the sequence CCAGGGA (SEQ ID NO: 2). In another aspect, the present invention provides an isolated oligonucleotide which ranges from about 7 to about 30 nucleotides in length and comprises the sequence TCCCTGG (SEQ ID NO: 1) or the sequence CCAGGGA (SEQ ID NO: 2). In yet another aspect, the present invention provides an isolated oligonucleotide which ranges from about 7 to about 21 nucleotides in length and comprises the sequence TCCCTGG (SEQ ID NO: 1) or the sequence CCAGGGA (SEQ ID NO: 2).

In a more general aspect, the invention provides an isolated oligonucleotide, wherein said oligonucleotide is capable of disrupting the interaction between the 5' untranslated region (UTR) and the 3' UTR of p53 mRNA.

In one embodiment, an oligonucleotide of the invention decreases the level or induction of p53 protein in response to a cellular stress. In another embodiment, the cellular stress is selected from the group consisting of ionizing radiation (IR), presence of a DNA damaging agent, hypoxia, hyperthermia, oxidation damage, chemotherapeutic agents, and UV light.

In one embodiment, an oligonucleotide of the invention consists essentially of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGG-GAAG (SEQ ID NO: 6), ACGCTTCCCTGG (SEQ ID NO: 7), CCAGGGAAGCGT (SEQ ID NO: 8), GACACGCTTC-CCTGG (SEQ ID NO: 9), CCAGGGAAGCGTGTC (SEQ ID NO: 10), GGTGACACGCTTCCCTGG (SEQ ID NO: 11), CCAGGGAAGCGTGTCACC (SEQ ID NO: 12), GACGGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACA-CAACCAACTGG (SEQ ID NO: 16). In a preferred embodiment, an oligonucleotide of the invention consists of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTC-CCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGA-CACGCTTCCCTGG (SEQ ID NO: 11), CCAGG-GAAGCGTGTCACC (SEQ ID NO: 12), GACGGTGA-CACGCTTCCCTGG (SEQ ID NO: 13), CCAGGGAAGCGTGTCACCGTC (SEQ ID NO: 14), TTTACGCTTCCCTGG (SEQ ID NO: 15), and GACA-CAACCAACTGG (SEQ ID NO: 16). The invention further encompasses derivatives of the above oligonucleotides, which derivatives are also capable of decreasing the level or induction of p53 protein. Preferably, such derivatives comprise TGG (or complementary CCA) as part of their sequence.

In a specific embodiment, an oligonucleotide of the invention is linked to a heterologous moiety. Non-limiting examples of useful heterologous moieties include, among others, a lipophilic moiety, a heterologous oligonucleotide sequence, a label, an intercalator, a chelator, an alkylator, and a cell penetrating peptide (CPP).

Further provided herein are pharmaceutical compositions comprising an oligonucleotide of the invention and a pharmaceutically acceptable carrier or excipient.

In conjunction with the oligonucleotide molecules of the present invention, the invention also provides a method for decreasing the level or induction of the p53 protein in a cell, which method comprises administering an oligonucleotide of the invention or a composition comprising such oligonucleotide. In a specific embodiment, the cell to which the oligonucleotide or composition is administered has been subjected to a stress. Non-limiting examples of such cellular stress include, among others, ionizing radiation (IR), presence of a DNA damaging agent, hypoxia, hyperthermia, oxidation damage, chemotherapeutic agents, and UV light. In one embodiment, the method for decreasing the level or induction of the p53 protein in a cell is used for achieving a medical effect selected from the group consisting of protection from toxicities of chemotherapy, protection from toxicities of radiation therapy, protection from toxicities of radiation exposure, reducing tissue/cell damage in hypoxia-reperfusion injury, reducing tissue/cell damage as a result of oxidative stress, reducing tissue/cell damage as a result of stresses associated with injuries, reducing tissue/cell damage in naturally occurring diseases, reducing tissue/cell damage in hyperthermia, inhibiting or decreasing tissue/cell aging, reducing or eliminating p53-dependent neuronal death or damage, preservation of tissues and organs prior to transplanting, and protection of cells of the central nervous system from cytotoxicity associated with neurodegenerative disorders.

The present invention further provides a method for preventing negative effects of a cellular stress in a subject, which method comprises administering to the subject in need thereof a therapeutically effective amount of an oligonucleotide of the invention or a composition comprising such oligonucleotide. In a preferred embodiment, the subject is human. In a specific embodiment, the cellular stress is selected from the group consisting of ionizing radiation, presence of a DNA damaging agent, hypoxia, hyperthermia, oxidation damage, chemotherapeutic agents, and UV light. In one embodiment, the method for preventing negative effects of a cellular stress is used for achieving a medical effect selected from the group consisting of protection from toxicities of chemotherapy, protection from toxicities of radiation therapy, protection from toxicities of radiation exposure, reducing tissue/cell damage in hypoxia-reperfusion injury, reducing tissue/cell damage as a result of oxidative stress, reducing tissue/cell damage as a result of stresses associated with injuries, reducing tissue/cell damage in naturally occurring diseases, reducing tissue/cell damage in hyperthermia, inhibiting or decreasing tissue/cell aging, reducing or eliminating p53-dependent neuronal death or damage, and preservation of tissues and organs prior to transplanting.

DETAILED DESCRIPTION OF THE INVENTION

As demonstrated previously by the present inventors and co-workers, the 5'-untranslated region (5'-UTR) of p53 mRNA and Ribosomal Protein L26 (RPL26) play an important role in regulating translation of p53 both in vitro and in vivo (see PCT Publication No. WO 2007/041213 and Takagi et al., Cell, 2005, 123(1): 49-63).

Figure 1A:
FIG. 1 demonstrate that a double-strand RNA region involving base pairing of 5'- and 3'-UTR sequences exists in human p53 mRNA. A. Minimum free energy computational modeling predicts a double-strand RNA region containing complementary sequences of the 5'-UTR and 3'-UTR of human p53 mRNA. A p53 mRNA sequence including a 75 base 5'-UTR, coding sequence, and the first 355 bases of the 3'-UTR, was input into an RNAfold program (Gruber et al., 2008; Hofacker, 2004; available from Vienna RNA Packages http://www.tbi.univie.ac.at/RNA/). A minimum free energy structure analysis predicted a double-strand RNA region containing 5'-UTR (positions −54 to −34) and 3'-UTR (positions +335 to +352) sequences. The schematic diagram shows the sequence and position of these bases in full-length human p53 mRNA (from GenBank Accession No. NM_000546.4) (SEQ ID NO: 35), with start and stop codons underlined and the mutations made in the various constructs used in these studies shown. B. Minimum free energy computational modeling of the 5'-UTR and 3'-UTR of human p53 mRNA as described above using sequences from human (NM_000987.3; SEQ ID NO:37), chimp (DQ048083.1; SEQ ID NO:38), Rhesus monkey (NM_001193566; SEQ ID NO:39), cow (NM_001015512.2; SEQ ID NO:40), rat (NM_001105788.1; SEQ ID NO:41), *Xenopus* (NM_001005104.1; SEQ ID NO:42), and zebrafish (NM_213113; SEQ ID NO:43).
Figure 1B:
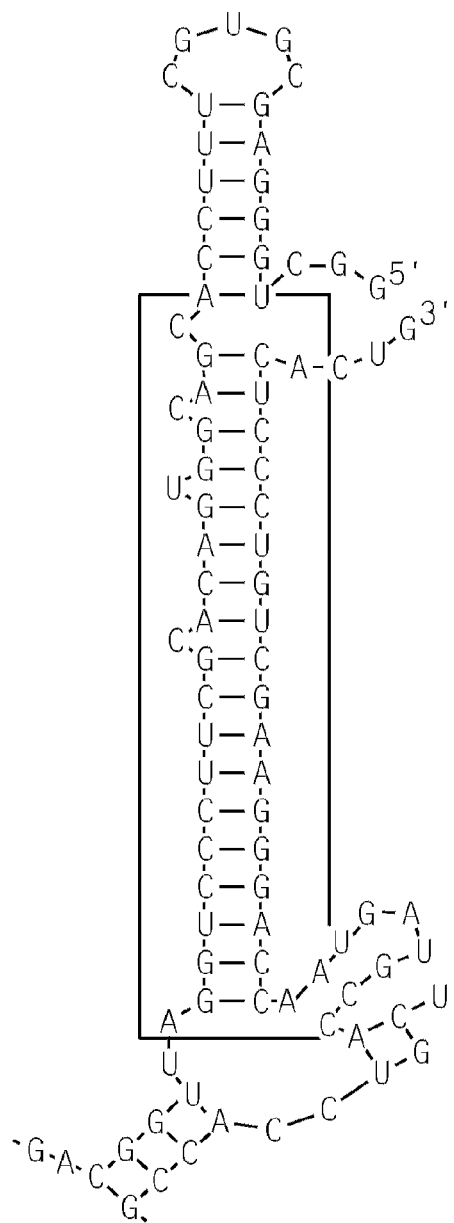
Figure 1B:
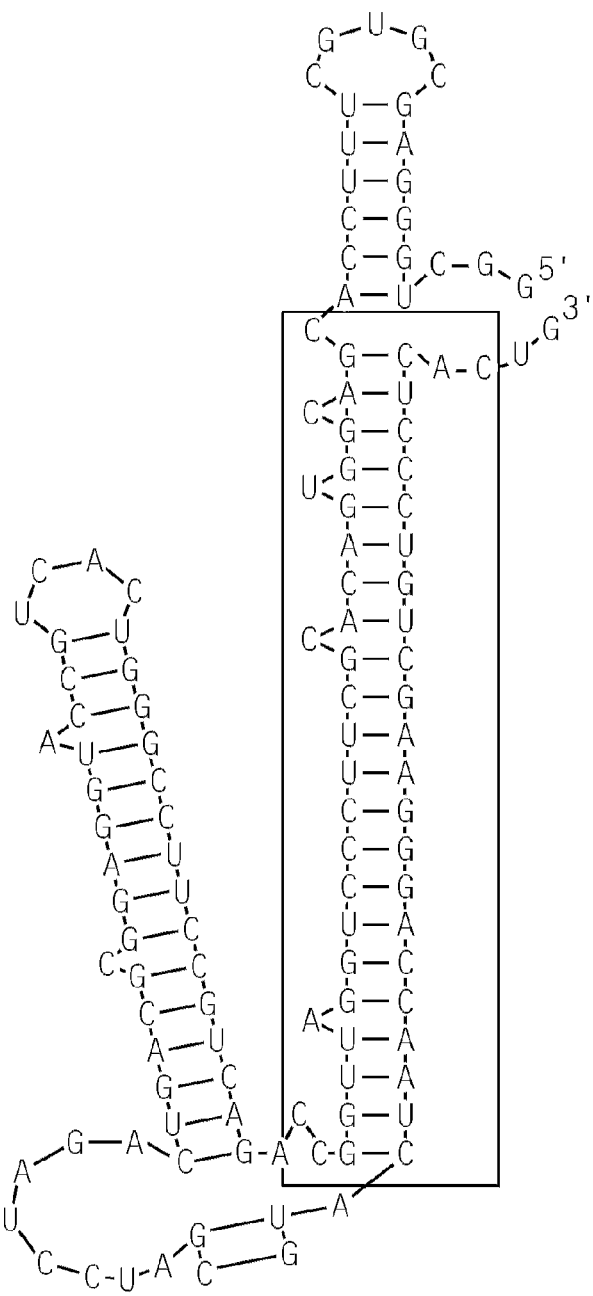
Figure 1B:
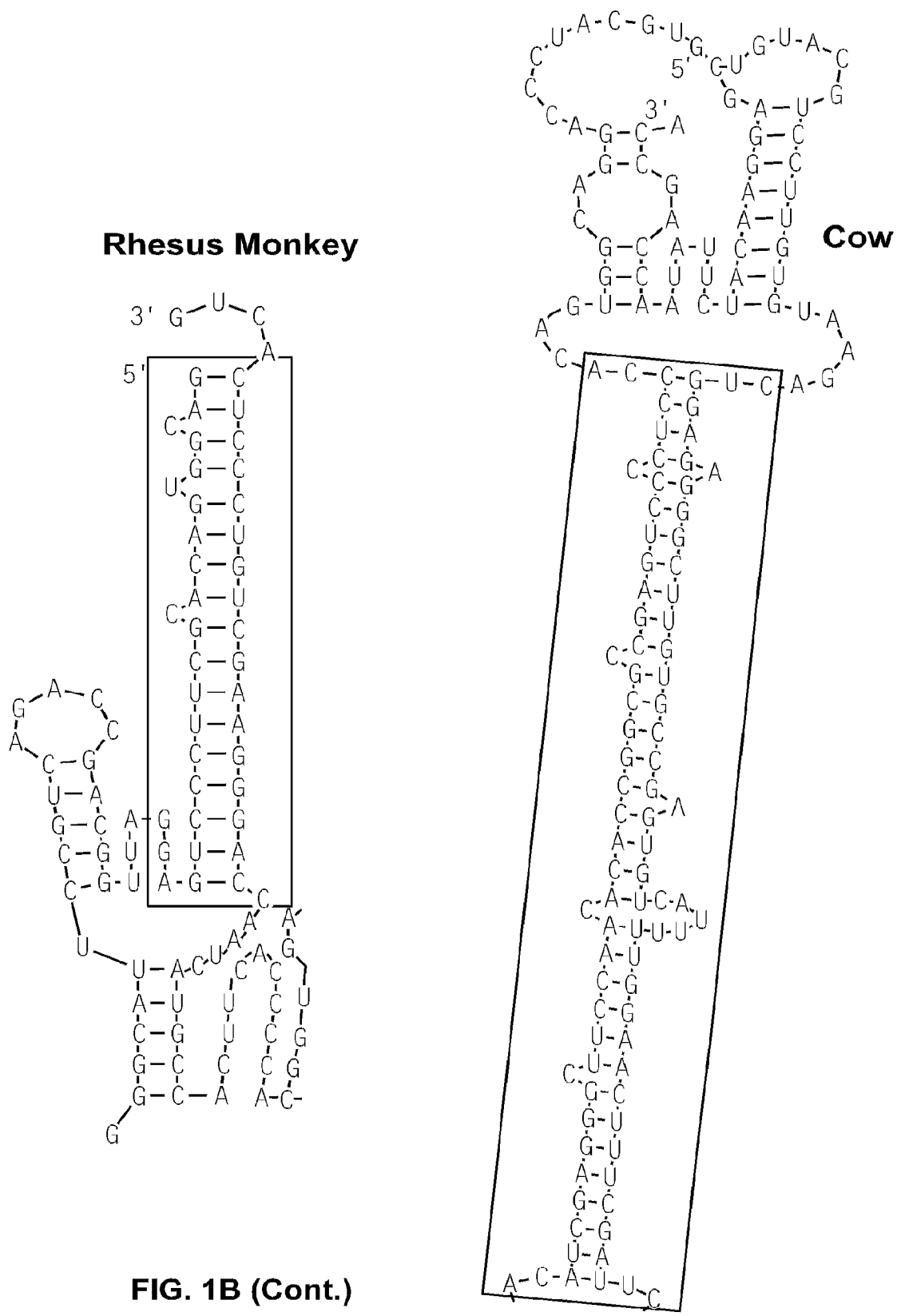
Figure 1B:
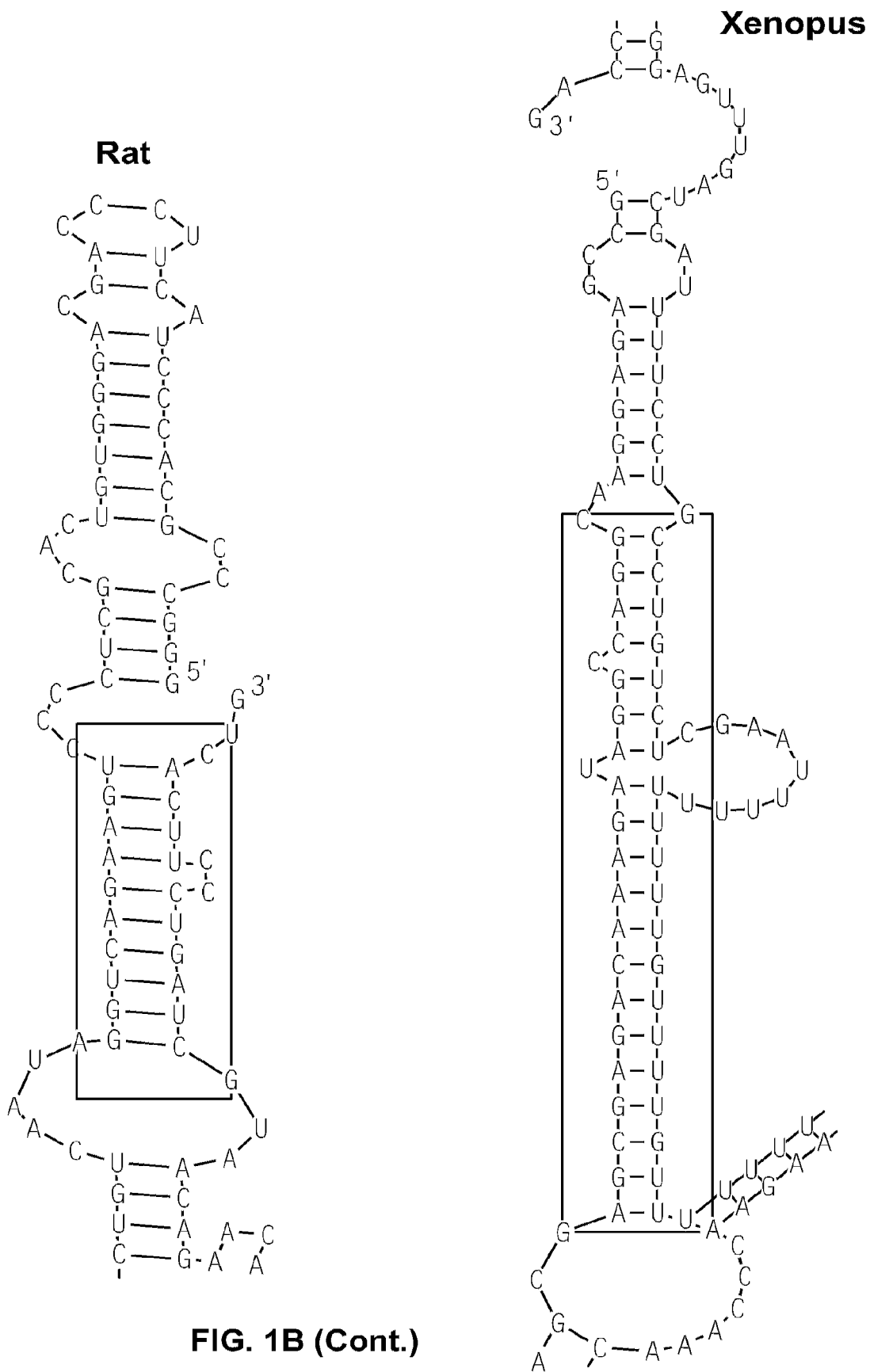
Figure 1B:
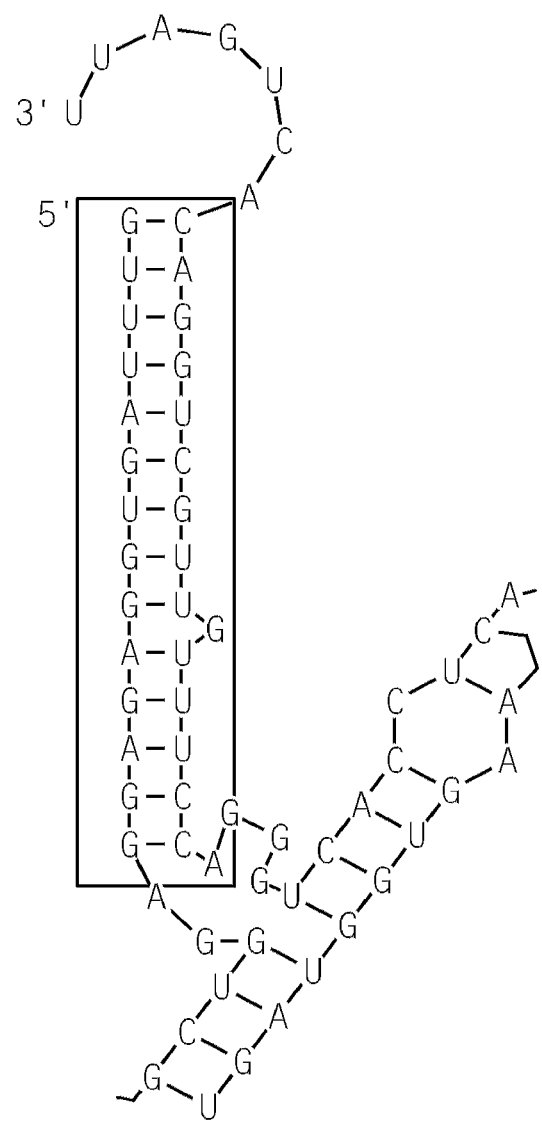

The present invention is based on the identification of a double-strand RNA region involving base pairing of 5'- and 3'-UTR in human p53 mRNA ("5'-3'-UTR interacting region of p53 mRNA"), which region is involved in RPL26-mediated p53 translational regulation after DNA damage. Specifically, it is presently discovered that RPL26 binds to both the 5'-UTR and the 3'-UTR of human p53 mRNA and that there is a 21 nucleotide sequence within the 5'-UTR of human p53 mRNA (positions −54 to −34, numbering from the start codon) that is largely complementary to a region within the 3'-UTR of human p53 mRNA (positions +335 to +352, numbering from the stop codon) (FIG. 1A; FIG. 1B shows the predicted complementary sequences in a number of different non-human species). As demonstrated in the Examples section, below, a 21 nucleotide-long DNA oligonucleotide having the sequence GACGGTGACACGCTTCCCTGG (5' oligo; SEQ ID NO: 13), or the complementary sequence CCAGGGAAGCGTGTCACCGTC (5'AS; SEQ ID NO: 14) derived from this 5'-UTR sequence, when transfected into cells, blocks p53 induction after exposing cells to ionizing irradiation (IR). As further provided herein, the 18 nucleotide-long fragment GGTGACACGCTTCCCTGG (L18; SEQ ID NO: 11), the 15 nucleotide-long fragment GACACGCTTCCCTGG (L15; SEQ ID NO: 9), the 12 nucleotide-long fragment ACGCTTCCCTGG (L12; SEQ ID NO: 7), the 9 nucleotide-long fragment CTTCCCTGG (L9; SEQ ID NO: 5), the 8 nucleotide-long fragment TTCCCTGG (L8; SEQ ID NO: 3), and the 7 nucleotide-long fragment TCCCTGG (L7; SEQ ID NO: 1) of the above 21-mer contain all of its inhibitory activity. In fact, as demonstrated in Example 3, below, using oligonucleotide mutants, only the last three bases (TGG) are absolutely critical for the p53 inhibitory effect of these oligonucleotides.

Thus, the present invention provides novel compounds which are specific inhibitors of p53 induction. Generally, a compound of the invention can be any oligonucleotide which affects the structure and/or protein interactions of the above-described 5'-3'-UTR interacting region of p53 mRNA. In a more specific aspect, such oligonucleotide is capable of interfering with RPL26 interaction with said p53 5'-3'-UTR interacting region or with the double-stranded structure of such region. In one aspect, the present invention provides an isolated oligonucleotide which comprises the sequence TCCCTGG (SEQ ID NO: 1) or the sequence CCAGGGA (SEQ ID NO: 2) and ranges from about 7 to about 50 nucleotides in length, preferably from about 7 to about 30 nucleotides in length, and most preferably from about 7 to about 21 nucleotides in length.

In certain embodiments, the oligonucleotides of the invention decrease the level or induction of p53 protein in response to a cellular stress such as, e.g., ionizing radiation (IR)), presence of a DNA damaging agent, hypoxia, hyperthermia, oxidation damage, chemotherapeutic agents, UV light, etc.

In a preferred embodiment, an oligonucleotide of the present invention consists of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGACACGCTTCCTGG (SEQ ID NO: 11), CCAGGGAAGCGTGTCACC (SEQ ID NO: 12), GACGGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACACAACCAACTGG (SEQ ID NO: 16). The invention further encompasses derivatives of the above oligonucleotides, which derivatives are also capable of inhibiting p53 induction. Preferably, such derivatives comprise TGG (or complementary CCA) as part of their sequence.

In a specific embodiment, an oligonucleotide of the invention is linked to a heterologous moiety. Non-limiting examples of useful heterologous moieties include, among others, a lipophilic moiety, a heterologous oligonucleotide sequence, a label, an intercalator, a chelator, an alkylator, and a cell penetrating peptide (CPP).

The effects of the oligonucleotides of the invention encompass many types of DNA damage and other stresses which induce p53 protein. Indeed, as disclosed in Example 4, below, the 15-mer GACACGCTTCCCTGG (SEQ ID NO: 9) and/or 8-mer TTCCCTGG (SEQ ID NO: 3) reduce p53 induction after treatment with UV, alkylating agents (MMS), anti-metabolites (5-FU), etoposide (ETO), or a hypoxia-mimic desferoxamine (DFO).

Since induction of p53 protein can lead to cell cycle arrest and cell death, the ability of the oligonucleotides of the invention to block stress-mediated induction of p53 makes them promising therapeutics for protection of normal tissues from the toxicities of chemical or radiation exposure; reducing tissue damage in hypoxia-reperfusion injury, neurodegenerative disorders, oxidative stress, injuries, hyperthermia; preventing aging; preservation of tissues and organs prior to transplanting, etc. The oligonucleotides of the invention which are 15 or less nucleotides long constitute particularly therapeutically promising compounds since they are small enough to enter cells without transfection. Indeed, as demonstrated in Example 3, below, simple incubation of the 15-mer oligonucleotide GACACGCTTCCCTGG (SEQ ID NO: 9) with human MCF-7 cells is sufficient to block p53 induction after ionizing radiation (IR). Furthermore, as demonstrated herein (see Example 4), incubation of HCT116 cells containing wild-type p53 with this 15-mer attenuates both p53 induction and cell death induced by treatment with 5-fluorouracil (5-FU). This oligonucleotide-mediated protection of cells from cell death is p53-dependent, since the same 15-mer had no measurable effect in p53-null HCT116 cells.

Due to their transient and reversible inhibitory activity on p53 induction, the administration of the oligonucleotides of the present invention is highly unlikely to cause any secondary tumorigenesis associated with p53 inhibition. This makes the oligonucleotides of the invention particularly attractive as therapeutics for reducing toxicity to normal tissues associated with anti-cancer treatments such as chemotherapy or radiation therapy, in particular, when treating tumors containing mutant p53 (about 50% of all human tumors). The p53-sequence-specificity is another important therapeutically relevant advantage of the oligonucleotides of the invention. Pifithrin-α, the only small molecule which has been previously reported to block p53-dependent transcriptional activation and apoptosis (Komarov et al., 1999), has unknown mechanisms of action and has now been shown to have p53-independent effects (Sohn et al., 2009), making its therapeutic usefulness questionable due to likely side-effects.

The oligonucleotides of the invention also constitute a useful research tool as they permit growth of cells in cultured systems that are difficult to grow because of "culture shock".

Definitions

The following definitions are provided for clarity and illustrative purposes only, and are not intended to limit the scope of the invention.

As used herein, the term "oligonucleotide" refers to a nucleic acid consisting of from 2 to 200 nucleotides, which may be DNA, RNA, a DNA-RNA chimera, or a derivative thereof (see the Oligonucleotide Modifications section, below).

As used herein, the term "complementary sequence," refers to a nucleic acid base sequence that can form a double-stranded structure with another DNA/RNA fragment to which it is complementary, by following base-pairing rules (e.g., A pairs with T/U, and C with G). Herein, all sequences are given in the 5' to 3' direction; thus, for example, the complementary sequence to GACACGCTTCCCTGG (SEQ ID NO: 9) is CCAGGGAAGCGTGTC (SEQ ID NO: 10).

As used herein, the term "heterologous moiety" can refer to any of the conjugates or fusion molecules of an oligonucleotide of the invention with a second molecule, wherein such second molecule is not a nucleic acid sequence that is identical to a fragment of p53 mRNA immediately adjacent to the oligonucleotide of the invention. Non-limiting examples of a heterologous moiety contemplated by the present invention include cell penetrating peptides such as TAT peptides, penetratin, an Antennepedia domain, transportan, poly-arginine, and MPG; lipid or lipophilic moieties, labels, such as radioisotopes or fluorescent molecules; and heterologous oligonucleotide sequences. Such heterologous moieties can be linked to an oligonucleotide of the invention by any suitable means known in the art, such as, but not limited to covalent attachment or chemical attachment.

Within the meaning of the present invention, the term "a function of a p53 5'-UTR" encompasses all possible structural and functional interactions of a p53 5'-UTR, including changes in its secondary and/or tertiary structure as well as interactions with various molecules (e.g., proteins, nucleic acids, ions, etc.).

Within the meaning of the present invention, the term "p53 induction" means increases in levels of p53 protein in a cell following a stress exposure. The term "p53 level" means level of p53 protein. The terms "inhibit p53 induction", "block p53 induction", "blunt p53 induction", "reduce p53 induction", "decrease p53 induction", "attenuate p53 induction" are used interchangeably to mean that stress-induced increases in levels of p53 protein are reduced.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject. Within the meaning of the present invention, disease conditions include without limitation various negative effects associated with cellular stress such as, e.g., (1) toxicities of chemotherapy, radiation therapy, unplanned radiation exposure (e.g., terrorist act), (2) tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., fever) or in hyperthermia, (3) tissue/cell aging, (4) p53-dependent neuronal death or damage (e.g., after brain or spinal cord injury or seizure), (5) damage of tissues and organs prior to transplanting, (6) cytotoxicity associated with neurodegenerative disorders (e.g., Huntington's Disease, Parkinson's Disease, ataxia-telangiectasia, amyotrophic lateral sclerosis (ALS) and the like), (7) tissue injury when the body is cooled down (e.g., near drowning), etc.

As used herein the term "therapeutically effective" applied to dose or amount refers to that quantity of a compound (e.g., oligonucleotide) or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a disease specified above. Note that when a combination of active ingredients is administered, the effective amount of the combination may or may not include amounts of each ingredient that would have been effective if administered individually. Therapeutically effective dosages according to the present invention can be determined stepwise by combinations of approaches such as, e.g., (i) characterization of effective doses of the compound in in vitro assays using p53 protein amount as a readout followed by (ii) characterization in cell cultures using p53 levels and/or p53-mediated apoptosis as a readout followed by (iii) characterization in animal studies using protection of tissues as a readout, followed by (iv) characterization in human trials using tissue protection as a readout.

The phrase "pharmaceutically acceptable", as used in connection with the compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The terms "administering" or "administration" as used herein are intended to encompass all means for directly and indirectly delivering a compound to its intended site of action. The compounds of the present invention can be administered locally to the affected site (e.g., by direct injection into the affected tissue or topically) or systemically. The term "systemic" as used herein includes, for example, parenteral, oral, transdermal, transmucosal, intranasal, and buccal administration. Parenteral administration includes subcutaneous, intravenous, intramuscular, intra-articular, intra-synovial, intra-arteriole, intradermal, intraperitoneal, intraventricular, intrasternal, intrathecal, intrahepatic, intralesional, and intracranial administration. A preferred route of administration according to the present invention will depend primarily on the indication being treated and includes, among others, topical, oral, subcutaneous, intravenous, and intranasal administration.

As used herein, the term "isolated" means that the material being referred to has been removed from the environment in which it is naturally found, and is characterized to a sufficient degree to establish that it is present in a particular sample. Such characterization can be achieved by any standard technique, such as, e.g., sequencing, hybridization, immunoassay, functional assay, expression, size determination, or the like. Thus, a biological material can be "isolated" if it is free of cellular components, i.e., components of the cells in which the material is found or produced in nature. For nucleic acid molecules, an isolated nucleic acid molecule includes, among others, synthetic oligonucleotides, PCR products, mRNA transcripts, cDNA molecules, restriction fragments, nucleic acid molecules excised from the chromosome, and nucleic acid molecules that have been spliced into vectors such as plasmids, cosmids, artificial chromosomes, phages and the like. Isolated nucleic acid molecules may contain regulatory and/or non-coding regions, and/or other regions located upstream or downstream of the corresponding gene when found in the chromosome. Isolated nucleic acid molecules of the present invention do not encompass uncharacterized clones in man-made genomic or cDNA libraries.

A protein that is associated with other proteins and/or nucleic acids with which it is associated in an intact cell, or with cellular membranes if it is a membrane-associated protein, is considered isolated if it has otherwise been removed from the environment in which it is naturally found and is characterized to a sufficient degree to establish that it is present in a particular sample. A protein expressed from a recombinant vector in a host cell, particularly in a cell in which the protein is not naturally expressed, is also regarded as isolated.

An isolated organelle, cell, or tissue is one that has been removed from the anatomical site (cell, tissue or organism) in which it is found in the source organism.

An isolated material may or may not be "purified". The term "purified" as used herein refers to a material (e.g., a nucleic acid molecule or a protein) that has been isolated under conditions that detectably reduce or eliminate the presence of other contaminating materials. Contaminants may or may not include native materials from which the purified material has been obtained. A purified material preferably contains less than about 90%, less than about 75%, less than about 50%, less than about 25%, less than about 10%, less than about 5%, or less than about 2% by weight of other components with which it was originally associated.

Methods for purification are well-known in the art. For example, nucleic acid molecules can be purified by precipitation, chromatography (including preparative solid phase chromatography, oligonucleotide hybridization, and triple helix chromatography), ultracentrifugation, and other means. Polypeptides can be purified by various methods including, without limitation, preparative disc-gel electrophoresis, isoelectric focusing, HPLC, reverse-phase HPLC, gel filtration, affinity chromatography, ion exchange and partition chromatography, precipitation and salting-out chromatography, extraction, and counter-current distribution. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. The term "substantially pure" indicates the highest degree of purity that can be achieved using conventional purification techniques currently known in the art. In the context of analytical testing of the material, "substantially free" means that contaminants, if present, are below the limits of detection using current techniques, or are detected at levels that are low enough to be acceptable for use in the relevant art, for example, no more than about 2-5% (w/w). Accordingly, with respect to the purified material, the term "substantially pure" or "substantially free" means that the purified material being referred to is present in a composition where it represents 95% (w/w) or more of the weight of that composition. Purity can be evaluated by chromatography, gel electrophoresis, immunoassay, composition analysis, biological assay, or any other appropriate method known in the art.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "subject" means any animal, including mammals and, in particular, humans.

As used in this specification and the appended claims, the singular forms "a," "an," and "the" include plural references unless the context clearly dictates otherwise.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Oligonucleotides of the Invention

The present invention provides an isolated oligonucleotide comprising the sequence TCCCTGG (SEQ ID NO: 1) or the sequence CCAGGGA (SEQ ID NO: 2) which oligonucleotide ranges from about 7 to about 50 nucleotides in length, preferably from about 7 to about 30 nucleotides in length, and most preferably from about 7 to about 21 nucleotides in length.

In one embodiment, an oligonucleotide of the invention consists essentially of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGACACGCTTCCCTGG (SEQ ID NO: 11), CCAGGGAAGCGTGTCACC (SEQ ID NO: 12), GACGGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACACAACCAACTGG (SEQ ID NO: 16).

In a preferred embodiment, the oligonucleotide of the present invention consists of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGACACGCTTCCCTGG (SEQ ID NO: 11), CCAGGGAAGCGTGTCACC (SEQ ID NO: 12), GACGGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACACAACCAACTGG (SEQ ID NO: 16).

Oligonucleotide Modifications

The oligonucleotides of the present invention include various oligonucleotide analogs and derivatives, which analogs and derivatives are also capable of decreasing the level or induction of p53 protein. Preferably, such analogs and derivatives comprise TGG (or complementary CCA) as part of their sequence. Such analogs and derivatives may have increased in vivo stability, particularly nuclease resistance, and/or reduced non-specific binding, and/or increased bioavailability as compared to unmodified oligonucleotides. The oligonucleotides may be modified at the backbone, the sugar moiety, or the bases themselves.

Examples of oligonucleotide backbone modifications include, without limitation, oligonucleotides that contain phosphorus group in the backbone, phosphorothioates, chiral phosphorothioates, phosphorodithioates, phosphotriesters, aminoalkylphosphotriesters, methyl and other alkyl phosphonates comprising 3' alkylene phosphonates and chiral phosphonates as well as short chain alkyl, or cycloalkyl intersugar linkages or short chain heteroatomic or heterocyclic intersugar linkages, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Specific examples include, among others, oligonucleotides with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$).

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. U.S. Pat. No. 5,034,506 describes oligonucleotides having morpholino backbone structures. U.S. Pat. No. 5,677,437 describes heteroaromatic oligonucleoside linkages. U.S. Pat. Nos. 5,792,844 and 5,783,682 describe nitrogen linkers or groups containing nitrogen. U.S. Pat. No. 5,637,684 describes phosphoramidate and phosphorothioamidate oligomeric compounds. Further examples include oligonucleotides with phosphorothioate backbones and oligonucleosides with heteroatom backbones, and in particular-$CH_2$—NH—O—$CH_2$—, —$CH_2$—N($CH_3$)—O—$CH_2$-known as a methylene (methylimino) or MMI backbone, —$CH_2$—O—N($CH_3$)—$CH_2$—, —$CH_2$N($CH_3$)—N($CH_3$) $CH_2$— and —O—N($CH_3$)—$CH_2$—$CH_2$— wherein the native phosphodiester backbone is represented as —O—P—O—$CH_2$—. See, e.g., U.S. Pat. Nos. 5,489,677 and 5,602,240.

In other oligonucleotide modifications encompassed by the present invention, both the sugar and the internucleoside linkage, i.e., the backbone, of the nucleotide units are replaced with novel groups. Example of such modification is a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. See, e.g., Nielsen et al., Science 1991; 254:1497.

Modified oligonucleotides encompassed by the present invention may also contain one or more substituted sugar moieties. Examples include oligonucleotides containing substituted sugar moieties comprising one of the following at the 2' position: OH, SH, $SCH_3$, F, OCN, $O(CH_2)_nO_mCH_3$, $O(CH_2)_nOCH_3$, $O(CH_2)_nNH_2$, $O(CH_2)_nCH_3$, $O(CH_2)_nONH_2$, and $O(CH_{2n}ON(CH_2)_nCH_3)_2$ where n and m can be from 1 to about 10; $C_1$ to $C_{10}$ lower alkyl, substituted lower alkyl, alkaryl or aralkyl; O-alkaryl or O-aralkyl; Cl; Br; CN; $CF_3$; $OCF_3$; O-; S-, or N-alkyl; O-, S-, or N-alkenyl; O, S- or N-alkynyl; or O alkyl-O-alkyl, wherein the alkyl, alkenyl and alkynyl may be substituted or unsubstituted C to $C_0$ alkyl or $C_2$ to $C_0$ alkenyl and alkynyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. See, e.g., Martin et al., Helv. Chim. Acta, 1995, 78, 486-504 which describes a modification comprising 2'-methoxyethoxy (2'-O—$CH_2CH_2OCH_3$, also known as 2'-O-(2-methoxyethyl) or 2'-MOE), i.e., an alkoxyalkoxy group. Another specific modification comprises 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2)_2$. Other preferred modifications comprise 2'-methoxy (2'-$OCH_3$), 2'-aminopropoxy (2'-O $CH_2CH_2CH_2NH_2$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls or other carbocyclics in place of the pentofuranosyl group.

Oligonucleotides of the invention may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases other synthetic and natural nucleobases such as xanthine, hypoxanthine, 6-methyl and other alkyl derivatives of adenine and guanine, 2-propyl and other alkyl derivatives of adenine and guanine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 2-thiocytosine, 5-halouracil and cytosine (e.g., 5-bromouracil), 5-hydroxymethyluracil, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine, $N_6$ (6-aminohexyl) adenine and 2,6-diaminopurine. A "universal" base known in the art, e.g., inosine, may be also included. See, e.g., Kornberg, A., DNA Replication, W. H. Freeman & Co., San Francisco, 1980, pp 75-77; Gebeyehu, G., et al. Nucl. Acids Res. 1987, 15:4513). Further modified nucleobases comprise those disclosed in U.S. Pat. No. 3,687,808, those disclosed in "The Concise Encyclopaedia of Polymer Science And Engineering", pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Crooke, S. T. and Lebleu, B., eds, 'Antisense Research and Applications', CRC Press, Boca Raton, 1993, pp. 276-302 and Crooke, S. T. and Lebleu, B. ea., CRC Press, 1993.

A further class of oligonucleotide modifications used in the present invention is referred to as cyclohexenyl nucleic acids (CeNA). The furanose ring normally present in a DNA or RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) in which the 2'-hydroxyl group of the ribosyl sugar ring is linked to the 4' carbon atom of the sugar ring thereby forming a 2'-O,4'-C-oxymethylene linkage to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr. Opinion Mol. Ther.,* 2001, 3, 239-243; see also U.S. Pat. Nos. 6,268,490 and 6,670,461). This bridge restricts the flexibility of the ribofuranose ring and locks the structure into a rigid C3-endo conformation, conferring enhanced hybridization performance and exceptional biostability (see, e.g., Uhlman, Current Opinions in Drug Discovery & Development 2000, Vol. 3 No. 2; Frieden et al., Nucleic Acids Research, 2003, 21, 6365-6372; Wahlestedt et al., Proc. Natl. Acad. Sci. U.S.A., 2000, 97, 5633-5638). The linkage can be a methylene ($-CH_2-$) group bridging the 2' oxygen atom and the 4' carbon atom, for which the term LNA is used for the bicyclic moiety; in the case of an ethylene group in this position, the term ENA is used (Singh et al., Chem. Commun., 1998, 4, 455-456; ENA™: Morita et al., Bioorganic Medicinal Chemistry, 2003, 11, 2211-2226). Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060). LNA and other bicyclic sugar analogs display very high duplex thermal stabilities with complementary DNA and RNA (Tm=+3 to +10° C.), stability towards 3'-exonucleolytic degradation and good solubility properties. LNAs are commercially available from, e.g., Pro-Ligo (Paris, France and Boulder, Colo., USA).

Another oligonucleotide modification encompassed by the present invention is threose nucleic acid (TNA) which contains threose nucleosides instead of ribose nucleosides. See, e.g., Chaput et al., J. Am. Chem. Soc., 2003, 125, 856-857; Wu et al., Organic Letters, 2002, 4(8), 1279-1282.

Further oligonucleotide mimetics have been prepared to include bicyclic and tricyclic nucleoside analogs (see Steffens et al., *Helv. Chim. Acta,* 1997, 80, 2426-2439; Steffens et al., *J. Am. Chem. Soc.,* 1999, 121, 3249-3255; Renneberg et al., *J. Am. Chem. Soc.,* 2002, 124, 5993-6002; and Renneberg et al., *Nucleic Acids Res.,* 2002, 30, 2751-2757). These modified nucleoside analogs have been oligomerized using the phosphoramidite approach and the resulting oligomeric compounds containing tricyclic nucleoside analogs have shown increased thermal stabilities (Tms) when hybridized to DNA, RNA and itself.

Another modification of the oligonucleotides of the invention involves chemically linking to the oligonucleotide one or more heterologous moieties which enhance the activity or cellular uptake of the oligonucleotide. Such heterologous moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-5-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. Tetrahedron Lett. 1995, 36, 3651; Shea et al. Nucl. Acids Res. 1990, 18, 3777), a polyamine or a polyethylene glycol chain (Manoharan et al. Nucleosides & Nucleotides 1995, 14, 969), or adamantane acetic acid (Manoharan et al. Tetrahedron Lett. 1995, 36, 3651), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). Oligonucleotides comprising lipophilic moieties, and methods for preparing such oligonucleotides are known in the art, for example, from U.S. Pat. Nos. 5,138,045, 5,218, 105 and 5,459,255. Other covalently linked moieties may include, for example, proteins, intercalators, chelators, or alkylators. The oligonucleotides herein may also be modified with a label capable of providing a detectable signal, either directly or indirectly. Exemplary labels include radioisotopes, fluorescent molecules, biotin, and the like.

It is not necessary for all positions in a given oligonucleotide to be uniformly modified. More than one of the aforementioned modifications may be incorporated in a single oligonucleotide or even within a single nucleoside within an oligonucleotide. The present invention also includes "chimeric" oligonucleotides, which contain two or more chemically distinct regions, each made up of at least one nucleotide. These chimeric oligonucleotides typically contain at least one region wherein the oligonucleotide is modified so as to confer increased resistance to nuclease degradation, increased cellular uptake, and/or increased binding affinity for the target nucleic acid or protein. An additional region of the oligonucleotide may serve as a substrate for enzymes or as a means for oligonucleotide detection.

Oligonucleotide Preparation

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlledpore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides. Preparation of LNA and derivatives has been described, for example, in PCT Publications Nos. WO 98/39352 and WO 99/14226; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039. Representative patents that teach the preparation of the phosphorus-containing linkages comprise, but are not limited to, U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Representative patents that teach the preparation of the oligonucleotides having backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. Representative patents that teach the preparation of PNA compounds comprise, but are not limited to, U.S. Pat. Nos. 5,539,082; 5,714,331; and 5,719, 262. See also Nielsen et al., Science, 1991, 254, 1497-1500. Representative patents that teach the preparation of modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646, 265; 5,658,873; 5,670,633; and 5,700,920. Representative patents that teach the preparation of the modified nucleobases comprise, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941. Representative patents that teach the preparation of oligonucleotide conjugates comprise, but are not limited to, U.S. Pat. Nos. 4,828,979; 4,948, 882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941. Representative patents that teach the preparation of chimeric oligonucleotides comprise, but are not limited to, U.S. Pat. Nos. 5,013,830; 5,149,797; 5,220, 007; 5,256,775; 5,366,878; 5,403,711; 5,491,133; 5,565,350; 5,623,065; 5,652,355; 5,652,356; and 5,700,922.

Pharmaceutical Compositions of the Invention

For administration to human and animal patients, the oligonucleotides of the present invention can be formulated in pharmaceutical compositions in combination with one or more pharmaceutically acceptable carriers and/or excipients such as, e.g., lubricants, diluents, flavorants, colorants, buffers, and disintegrants. Suitable pharmaceutically acceptable carriers include any and all conventional solvents (such as, e.g., water, physiological solution, dextrose, glycerol, ethanol, and the like, as well as combinations thereof), wetting agents, emulgators, buffers, conservants, dispersion media, fillers, solid carriers, aqueous solutions, coatings, antibacterial and antifungal agents, isotonic and absorption delaying agents, as well as other well-known agents which enhance the shelf life or effectiveness of one or more of the active components of the composition. Examples of such useful substances can be found in "Remington's Pharmaceutical Sciences" by E. W. Martin. Except insofar as any conventional media or agent is incompatible with the active ingredient, use thereof in compositions of the present invention is contemplated. The term "pharmaceutically acceptable" refers to a carrier or excipient that does not cause an allergic reaction or other untoward effect in patients to whom it is administered.

The pharmaceutical compositions of the invention can be produced in useful dosage units for administration by various routes including, among others, topical, oral, subcutaneous, intravenous, and intranasal administration.

The pharmaceutical compositions of the invention can also include other biologically active substances in combination with the oligonucleotides of the invention. Such additional biologically active substances can be also formulated as separate compositions and can be administered simultaneously or sequentially with the oligonucleotides of the invention. Non-limiting examples of useful biologically active substances include taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; radioisotopes, and various agents such as procarbazine, mitoxantrone, and biological response modifiers or growth factor inhibitors such as interferons or interleukins.

For treatment of diseases and conditions resulting from cellular stresses, the pharmaceutical compositions comprising the oligonucleotides of the invention can be also combined with other biologically active substances (in the same or separate compositions administered simultaneously or sequentially) or treatment regimes. Non-limiting examples of anti-stress treatments include changes in diet, for example, increased intake of fruit and vegetables, and supplementation of the diet with phyotochemicals or antioxidants, such as vitamin B12. For example, for the treatment of stroke useful additional agents include antiplatelet agents (e.g., aspirin, clopidogrel, dipyridamole, ticlopidine), anticoagulant agents (e.g., heparin, warfarin), and thrombolytic agents (e.g., tissue plasminogen activator). Secondary anti-stress therapy measures may also include administration of drugs with antioxidant activity such as methylprednisolone, 21-aminosteroids, 2-methylaminochromans, pyrrolopyrimidines, and thiazolidinones.

Oligonucleotide Administration

With the aid of present disclosure, those of skill in the art should be able to derive suitable dosages and schedules of administration for any of a number of suitable compositions that contain the oligonucleotides of the invention. Thus, pharmaceutical compositions within the scope of the present invention include compositions where the active ingredient is contained in an effective amount to reduce stress-related induction of p53.

The formulation and dose for therapeutic administration of the oligonucleotides of the invention will depend on the severity of the disease condition being treated, whether other drugs are being administered, whether other actions are taken, the weight, age, and sex of the subject, and other criteria. The skilled medical practitioner will be able to select the appropriate formulation and dose in view of these criteria and based on the results of published clinical trials. The dosage and administration regimen can be further adjusted for an individual patient by monitoring the level of cell death in a target tissue (e.g., using imaging based on electromagnetic radiation, x-rays, magnetic resonance, or annexin V and/or propidium iodide (PI) staining followed by flow cytometry analysis, etc.; immunohistochemistry; Hematoxylin and Eosin (H&E) staining; TUNEL assay; electron microscopy, fluorescent microscopy, etc.)

The optimal therapeutically effective amount of an oligonucleotide or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

As disclosed herein, the concentrations of the oligonucleotides administered in the present invention are both therapeutically effective and pharmaceutically acceptable. The oligonucleotides of the present invention are preferably used to treat or prevent tissue damage in vivo at 0.1-5 mg/kg of body weight, most preferably at 0.5-2 mg/kg.

The efficacy of the oligonucleotides and compositions of this invention can be determined using the in vitro and in vivo assays such as assays monitoring the level of cell death in a target tissue (e.g., using imaging based on electromagnetic radiation, x-rays, magnetic resonance, etc.; immunohistochemistry; Hematoxylin and Eosin (H&E) staining; TUNEL assay; electron microscopy, fluorescent microscopy, annexin V and/or propidium iodide (PI) staining followed by flow cytometry analysis, etc.

Following methodologies which are well-established in the art, effective doses and toxicity of the oligonucleotides and compositions of the present invention, which performed well in in vitro tests, can be determined in studies using small animal models (e.g., mice, rats or dogs) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the oligonucleotide in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

The oligonucleotides of the invention can be formulated for parenteral, oral, topical, transdermal, transmucosal, intranasal, buccal administration, or by any other standard route of administration. Parenteral administration includes, among others, intravenous (i.v.), subcutaneous (s.c.), intraperitoneal (i.p.), intramuscular (i.m.), subdermal (s.d.), intradermal (i.d.), intra-articular, intra-synovial, intra-arteriole, intraventricular, intrathecal, intrasternal, intrahepatic, intralesional, or intracranial administration, by direct injection, via, for example, bolus injection, continuous infusion, or gene gun. A preferred route of administration according to the present invention will depend primarily on the indication being treated and includes, among others, topical, oral, subcutaneous, intravenous, and intranasal administration.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use. Suitable formulations for parenteral administration may contain substances which increase viscosity, for example, sodium carboxymethyl cellulose, sorbitol, and/or dextran. Optionally, the formulation may also contain stabilizers. Additionally, the oligonucleotides of the present invention may also be administered encapsulated in liposomes. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Oligonucleotide Delivery

To produce a specific effect on the cells under stress or neurodegenerated tissues, compositions of the present invention can be delivered systemically or locally. If targeted delivery to a particular cell or tissue is desirable, oligonucleotide conjugates or oligonucleotide delivery vectors containing antibodies to cell- or tissue-specific antigens can be used. Alternately, compositions of the present invention can be injected directly into tissues. In case of cells of the central nervous system, compositions of the invention can be also delivered directly to the area through injections or into the cerebrospinal fluid.

As specified above, some of the oligonucleotides of the present invention (e.g., 15-mers and smaller) are small enough to enter cells without transfection or other methods of facilitating cell entry. Other oligonucleotides can be chemically modified (e.g., by chemically linking them to a lipophilic moiety or other heterologous moiety) to enhance their cellular uptake. However, even these oligonucleotides may require specific delivery methods and delivery systems to ensure their efficient and targeted delivery to the tissue to be treated. Oligonucleotide delivery methods of the present invention include both local and systemic administration of stabilized nucleic acids, oligonucleotides incorporated into delivery vectors, and/or oligonucleotides conjugated to peptides or small molecules that are subsequently transported into cells. Mechanical and electrical strategies for targeted oligonucleotide delivery include microinjection, particle bombardment, the use of pressure, and electroporation.

Vector-assisted oligonucleotide delivery systems include biological viral delivery systems and chemical non-viral delivery systems. Viral delivery systems include without limitation retroviruses, parvoviruses, adenoviruses, lentiviruses, adeno-associated viruses, herpes simplex virus, pseudovirions, etc. Non-viral delivery systems (which are clinically preferable due to lack of immune response and ease of formulation and assembly) include (i) polymeric delivery systems (oligonucleotide-polymer complexes) and (ii) liposomal delivery systems (oligonucleotides entrapped in and/or complexed to liposomes). Commonly used polymers in polymeric delivery systems include, for example, polyethylenimine (PEI), poly(L-lysine) (PLL), chitosans, and polyamidoamine (PANAM) dendrimers (e.g., commercially available Superfect and Polyfect [Qiagen, Valencia, Calif.]). Agents such as folates, transferrin, antibodies, or sugars such as galactose and mannose can be also incorporated for tissue targeting.

Liposomal delivery systems include systems that deliver oligonucleotides either by entrapping them inside an aqueous core or complexing them to the phospholipid lamellae. Similarly to viral vectors, liposomes offer substantial protection to the oligonucleotide therapeutics from nucleases and improve their biological stability. Liposomes may also offer significant advantages over viral delivery options for the delivery of oligonucleotide therapeutics due to much lower immunogenicity (because they lack proteinaceous components) and their versatility. Since the phospholipid composition in the liposome bilayers can be varied, liposomal delivery systems can be easily engineered to yield a desired size, surface charge, composition, and morphology. Liposomes for oligonucleotide delivery according to the present invention can include a variety of cationic, anionic, synthetically modified lipids, and combinations thereof.

Examples of cationic lipids include without limitation 3β[N—(N',N'-dimethylaminoethane)-carbamoyl]cholesterol (DC-chol)/DOPE, 1,2-dioleoyl-3-trimethylammonium propane (DOTAP), N-[1-(2,3-dioleyloxy)propyl]-N,N,N-trimethylammonium chloride (DOTMA), 2,3-dioleoyloxy-N-[2-(sperminecarboxamido)ethyl]-N,N-dimethyl-1-propanaminium (DOSPA), dioctadecyl amido glycil spermine (DOGS), 3,[N—(N1,N-dimethylethylenediamine)-carbamoyl]cholesterol (DC-chol), polyethyleneimine (PEI), polyamidoamine (PAMAM) dendrimers, and poly-L-lysine (PLL). Commonly used zwitterionic lipids, also known as helper lipids, are DOPE, 1,2-dipalmitoyl-sn-glycero-3-phosphocholine (DPPC), and cholesterol. The cationic lipids in the liposomal formulation serve as an oligonucleotide complexation and condensation agents during the formation of the lipoplex. The positive charge also helps in cellular association. The zwitterionic lipids help in membrane perturbation and fusion. Proprietary formulations of cationic lipids such as Lipofectamine (Invitrogen, Carlsbad, Calif.), Effectene (Qiagen, Valencia, Calif.), and Tranfectam (Promega, Madison, Wis.) are commercially available.

Examples of anionic lipids include without limitation DPPC and 1,2-dimyristoyl-sn-glycero-3-[phospho-rac-(1-glycerol)] (DMPG). LPDII vectors can be also used for delivery of the oligonucleotides of the present invention. These are non-viral delivery vehicles that consist of a complex between anionic pH-sensitive liposomes and polycation-condensed oligonucleotides (polyplexes). Another useful delivery vehicle can be composed of a mixture of anionic lipid 1,2-dioleoyl-sn-glycero-3-[phospho-rac-(1-glycerol)] (sodium salt) (DOPG) and zwitterionic lipid DOPE.

Other useful specialized liposomal delivery platforms include pH-sensitive liposomes, immunoliposomes, and stealth liposomes. pH-sensitive liposomes can be generated by the inclusion of DOPE or citraconyl-DOPE or phosphatidylcholine/glycyrrhizin combination into liposomes composed of acidic lipids such as cholesterylhemisuccinate or oleic acid. At the neutral cellular pH 7, these lipids have the typical bilayer structure; however, upon endosomal compartmentalization they undergo protonation and collapse into a non-bilayer structure, thereby leading to the disruption and destabilization of the endosomal bilayer, which in turn helps in the rapid release of the oligonucleotide into the cytoplasm. Immunoliposomes incorporate functionalized antibodies attached to lipid bilayers and thus target specific receptors and facilitate receptor-mediated endocytosis for the uptake of the lipoplex. Stealth liposomes are sterically stabilized liposomal formulations that include polyethylene glycol (PEG)-conjugated lipids. Pegylation prevents the opsonization and recognition of the liposomal vesicles by the reticuloendothelial system. Consequently, stealth liposomes have long circulating times in the systemic circulation.

Liposomes useful for oligonucleotide delivery according to the present invention can take a shape of multilamellar vesicles (MLV) formed by reconstituting thin lipid films in buffer. Small unilamellar vesicles (SUV) of specific size (100-500 nm) can be produced by extruding MLV through polycarbonate membranes. SUV (50-90 nm) can also be produced by sonication of MLV or larger SUV.

Transmembrane permeation of the oligonucleotides of the invention can be also enhanced by inclusion of cell penetrating peptides (CPPs; also termed "peptide transduction domain" (PTD)) in the delivery vehicles or covalent oligonucleotide conjugation to such peptides. Conjugated CPPs are also contemplated for use as a heterologous moiety of the present invention. CPPs/PTDs are a class of small cationic peptides of approximately 10-30 amino acids in length that have been shown to engage the anionic cell surface through electrostatic interactions and rapidly induce their own cellular internalization through various forms of endocytosis. Examples of useful CPPs/PTDs include TAT peptide, penetratin, an Antennepedia domain, transportan, poly-arginine, and MPG.

Other compounds useful in delivery of the oligonucleotides of the present invention include cyclodextrins (CyDs), porphyrin derivatives, branched chain dendrimers, polyethylenimine polymers, nanoparticles, microspheres, and polylysine conjugates with vector proteins such as asialofetuin or transferrin.

Preferred methods of oligonucleotide delivery according to the present invention include Lipofectamine 2000 or Lipofectamine RNAiMAX (Invitrogen) (used to transfect oligonucleotides into cells), antibodies, peptides, liposomes, and nanoparticles. Other methods include addition of naked oligonucleotides.

More information on useful delivery vehicles and methods can be obtained from recent reviews such as, e.g., Meade and Dowdy, Adv Drug Deliv Rev., 2008, 60(4-5): 530-6; Juliano et al., Nucleic Acids Res., 2008, 36(12): 4158-71; Lysik and Wu-Pong, J. Pharmaceutical Sciences, 2003, 92: 1559; Dass, J., Pharmacy Pharmacol., 2002, 54 (1): 3-27, and references cited therein. See also Lorenz et al., Bioorg Med Chem Lett., 2004, 14(19): 4975-7; Dalby et al., Methods, 2004 33(2): 95-103; Hassani et al., J. Gene Med., 2005, 7(2): 198-207; Pirollo et al., Hum Gene Ther., 2006, 17(1): 117-24; Jaaskelainen et al., Eur J Pharm Sci., 2000, 10(3): 187-93; Urban-Klein et al., Gene Ther., 2005, 12(5): 461-6; Zhou et al., Chem. Commun (Camb), 2006. 22: 2362-4; Leng et al., J. Gene Med., 2005, 7(7): 977-86.

In vivo nuclease degradation of oligonucleotides of the invention can be circumvented by chemical derivatization of the backbone and/or by the protection and stability offered by the above-described vector delivery systems. As discussed above, various chemical modifications to the backbone can be used to improve oligonucleotide stability. The most common modifications include the introduction of phosphorothioate and/or methyl phosphonate linkages in the backbone. Phosphorothioate analogs are chosen for their stability against nucleases and the methylphosphonate backbone for its relative hydrophobicity and ease of diffusion across membranes. Mixed-backbone oligonucleotides can also be used. To ensure protection of the oligonucleotides of the invention from the endosomal degradation upon intracellular delivery, viral delivery vectors or pH-sensitive and cationic liposome delivery systems (e.g., including fusogenic lipids such as 1,2-dioleoyl-sn-glycero-3-phosphoethanolamine (DOPE)). Lysosomatropic agents such as monensin and chloroquine, which raise the endosomal pH, block acidification, and thus inhibit lysozyme activity, can also be used to facilitate endosomal release of the oligonucleotides of the invention. In addition, endosomal degradation of oligonucleotides can be circumvented by the incorporation of viral peptides such as hemagglutinin HA2 and those derived from adenoviruses in their delivery systems or by using fusogenic peptides such as poly(L-lysine) (PLL) and cationic polymers such as polyethylenimine (PEI) and dendrimers. See the review by Patil et al., AAPS J., 2005, 7(1): E61-E77 and references cited therein.

Therapeutic Methods of the Invention

In conjunction with the novel oligonucleotides of the present invention, provided herein are methods of treatment using such oligonucleotides. Since the increase of p53 protein levels causes cells to either undergo a growth arrest or undergo programmed cell death, the decrease in p53 protein levels or inhibition of the p53 induction upon the administration of the oligonucleotides of the present invention can be useful for protecting tissues from cell death which results from cellular stresses such as ionizing radiation, presence of a DNA damaging agent, hypoxia, hyperthermia, oxidation damage, chemotherapeutic agents, UV light, etc. Accordingly, the oligonucleotides of the present invention can be useful in the following therapeutic applications: (1) protection of normal tissues (e.g., bone marrow and/or gastrointestinal mucosa) from the toxicities of chemotherapy or radiation therapy when treating cancers (in particular, in the treatment of tumors containing mutant p53 [about 50% of all human tumors], where the decreasing/blocking p53 translation could protect the normal tissue but not affect the response of the tumor); (2) protection of normal tissues from inadvertent exposure to dangerous chemicals or radiation (e.g., during a "dirty" nuclear explosion); (3) reducing tissue/cell damage in hypoxia-reperfusion injury (e.g., during blocked blood supply, stroke or ischemia), or as a result of oxidative stress (e.g., in certain neurodegenerative disorders), or as a result of stresses associated with injuries (e.g., burns), or in naturally occurring diseases (e.g., fever) or in hyperthermia; (4) inhibiting/decreasing tissue/cell aging; (5) reducing or eliminating p53-dependent neuronal death or damage (e.g., after brain or spinal cord injury or seizure), (6) preservation of tissues and organs prior to transplanting, (7) protecting cells of the central nervous system from cytotoxicity associated with neurodegenerative disorders (e.g., Huntington's Disease, Parkinson's Disease, ataxia-telangiectasia, amyotrophic lateral sclerosis (ALS) and the like), and (8) growing stem cells in culture.

The present invention therefore provides a method for decreasing the level or induction of the p53 tumor suppressor protein in a cell, which method comprises administering the oligonucleotide(s) of the invention. The present invention further provides a method for preventing negative effects of a cellular stress in a subject, which method comprises administering to the subject in need thereof a therapeutically effective amount of the oligonucleotide(s) of the present invention. In a preferred embodiment, the subject is human.

In a specific embodiment, the method comprises administering the oligonucleotide(s) of the invention before subjecting the subject to a treatment selected from the group consisting of radiation therapy, chemotherapy, thermotherapy, and any combination thereof. Administration of the oligonucleotides of the invention after or during the above treatments is also contemplated.

EXAMPLES

The present invention is further described by way of the following particular examples. However, the use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

Experimental Procedures

Cell Culture, Transfection and Cell Death Assays.

Human breast cancer cell line MCF-7 (wild-type p53; ATCC Accession No. HTB-22, ATCC, Manassas, Va.) and human lung carcinoma cell line H1299 (p53-null; ATCC Accession No. CRL-5803, ATCC, Manassas, Va.) were maintained in Dulbecco's modified Eagle medium (DMEM; Gibco Invitrogen, Carlsbad, Calif.) containing 10% fetal calf serum (FCS; Gibco Invitrogen). Human colorectal carcinoma cell line HCT116 (ATCC Accession No. CCL-247; ATCC, Manassas, Va.) and p53−/− HCT116 cells (obtained from Dr. Bert Vogelstein, The Sidney Kimmel Comprehensive Cancer Center at the Johns Hopkins University Medical Institute, Baltimore, Md.; Bunz, et al., Science 1998; 282:1497-1501) were maintained in Dulbecco's modified Eagle medium (DMEM; Gibco Invitrogen, Carlsbad, Calif.) containing 10% fetal calf serum (FCS; Gibco Invitrogen). Plasmids and oligonucleotides were transfected into cells using Lipofectamine 2000 (Invitrogen) and LipofectamineRNAiMAX (Invitrogen). Cell death was assessed by a Propidium Iodide (PI) staining assay adapted from Yu and Little (Yu and Little, 1998). Briefly, 4 hours post incubation with oligonucleotides, HCT116 WT or HCT116 p53−/− cells were exposed to 100 µM 5-fluorouracil (5-FU) for 20 hours. Cells were harvested, fixed with 100% cold methanol and incubated with 10 µg/ml PI plus 250 µg/ml RNaseA solution at room temperature for 30 minutes before FACS analysis. In cell protection assays, 4 hours post transfection with the indicated fluorescein (FAM)-conjugated oligonucleotides, HCT116 WT or HCT116 p53−/− cells were exposed to 170 µM etoposide (Bedford Lab) for the indicated periods of time. Cells were then harvested, washed once with PBS, and resuspended in 10 µg/ml PI/PBS solution before FACS analysis.

Plasmids, Oligonucleotides and Proteins.

p53 and its mutants were constructed in a pLPCX vector (Takagi et al., 2005). GFP-RPL26 and Flag-RPL26 were constructed in pEGFP-C3 and pCMV-FLAG vectors, respectively (Clontech; BD Biosciences, Franklin Lakes, N.J.). Luciferase reporter constructs were based on a pGL3ctrl vector (Promega, Madison, Wis.). Oligonucleotides used in this study were synthesized at the Hartwell Center of the St. Jude Children's Research Hospital. Recombinant RPL26 (aa 45-145) protein was purchased from Abnova (Walnut, Calif.).

Oligonucleotides were synthesized at the Hartwell Center of St Jude Children's Research Hospital. The sequences of the oligonucleotides used were as follows:

| NAME | SEQUENCE | SEQ ID NO |
|---|---|---|
| L7 | TCCCTGG | 1 |
| L8 | TTCCCTGG | 3 |
| F9 | GGTGACACG | 31 |
| L9 | CTTCCCTGG | 5 |
| F12 | GGTGACACGCTT | 32 |
| L12 | ACGCTTCCCTGG | 7 |
| F15 | GGTGACACGCTTCCC | 18 |
| L15 | GACACGCTTCCCTGG | 9 |
| luc15 | AGGGCGTATCTCTTC | 19 |
| L15AS | CCAGGGAAGCGTGTC | 10 |
| L15m1 | TTTACGCTTCCCTGG | 15 |
| L15m2 | GACACAACCAACTGG | 16 |
| L15m3 | GACACGCTTCCCAAA | 17 |
| F18 | GACGGTGACACGCTTCCC | 20 |
| L18 | GGTGACACGCTTCCCTGG | 11 |
| luc18 | AGGGCGTATCTCTTCATA | 21 |
| 5'oligo | GACGGTGACACGCTTCCCTGG | 13 |
| 5'AS | CCAGGGAAGCGTGTCACCGTC | 14 |
| luc21 | ACCAGGGCGTATCTCTTCATA | 22 |
| 5'ctrl1 | GCTGGGAGCGTGCTTTCCACGA | 23 |
| 5'ctrl2 | CTGCCTTCCGGGTCACTGCCA | 24 |
| 3'ctrl1 | TCGTGGAAAGCACGCTCCCAGC | 25 |
| 3'ctrl2 | TGGCAGTGACCCGGAAGGCAG | 26 |

RNA Synthesis and In Vitro Transcription/Translation.

Capped p53 mRNA was transcribed in vitro using the mMESSAGE mMACHINE kit (Ambion, Austin, Tex.) followed by a poly(A) tailing kit (Ambion) to add a poly(A) tail modification. The synthesized mRNA was further purified through MEGAClear column (Ambion) and quantified using Nanodrop (NanoDrop Technologies, Inc., Wilmington, Del.). RNA without modification was synthesized using MEGAscript High Yield Transcription kit (Ambion). All synthesized RNA was purified by MEGAclear Kit (Ambion) according to manufacturer's protocol.

Dual Luciferase Assay.

Luciferase assays were performed by using the Dual-Luciferase reporter assay system (Promega) according to the manual provided by the manufacture. Briefly, MCF-7 cells were cotransfected with 4 μg Flag-RPL26, 100 ng −145pG13ctrl+/−3'-UTR (wild type or mutated 145 base 5'-UTR, luciferase coding sequence, with or without 3'-UTR of human p53 mRNA (derived from GenBank Accession No. NM_000546.4 (SEQ ID NO: 35)) and 27 ng pRL-TK. 24 hours post-transfection, cell lysates were prepared and subjected to the reporter assay according to the manual instruction.

Immunoblot and IP-RT-PCR.

Cell lysates were prepared by a freeze/thaw followed by incubation in RIPA buffer (150 mM NaCl, 1.0% NP40, 0.1% sodium dodecyl sulfate [SDS], 0.1% sodium deoxycholate, 5 mM EDTA, 10 mM Tris-HCl, pH 7.4, containing protease inhibitors [complete mini cocktail; Roche Diagnostics, Indianapolis, Ind.] and 0.5 mM PMSF) for 30 minutes on ice and supernatants were analyzed by immunoblot analysis. 20 μg protein samples were denatured in an equal volume of SDS sample buffer, separated by 4-12% SDS-PAGE and transferred to nitrocellulose membrane. The blots were probed with primary antibody against p53 (DO-1; Santa Cruz Biotechnology, Santa Cruz, Calif.), GFP (FL; Santa Cruz Biotechnology, Santa Cruz, Calif.), RPL26 (Bethyl Laboratories, INC) or Actin (Sigma). Primary antibody binding was detected by incubating with horseradish peroxidase (HRP)-conjugated anti-rabbit, anti mouse secondary antibody and further enhanced chemiluminescent visualization (ECL) system (Amersham Biosciences, Buckinghamshire, UK).

IP-RT-PCR was performed as previously described in (Takagi et al., 2005). Briefly, cells were lysed in polysome lysis buffer (100 mM KCl, 5 mM $MgCl_2$, 10 mM HEPES, pH 7.0, 0.5% NP40, 1 mM DTT, 100 U/ml SUPERase●In, protease inhibitor cocktail, 0.5 mM PMSF). After preclearing lysates with mouse IgG (Sigma-Aldrich) and protein A/G-PLUS agarose, primary antibody and protein A/G PLUS agarose was incubated with 100 μl precleared cell lysate, 900 μl NT2 buffer (50 mM Tris-HCl, pH 7.4, 150 mM, NaCl, 1 mM MgCl2, 0.05% NP40), 100 Uml SUPERase●In, 1 mM DTT, and 15 mM EDTA for 1 h at 4° C. RNA was extracted using Trizol (Invitrogen) after extensive washing with NT2 buffer, reverse transcribed by using Superscript II (Invitrogen) with random primer and amplified by PCR. For IP-RT-PCR, immunoprecipitated protein complexes were split in half: one half was used for immunoblot analysis and the other half was used for RT-PCR.

Real-time RT-PCR was performed using 7900HT sequence detection system and TaqMan One-Step PCR MasterMix Reagents kit (ABI). The primer/TaqMan probe set for human p53 was: Hs00153340_m1 (20× mix) (Applied Biosystems Inc. (ABI), Foster City, Calif.) or Hs00153349_m1. Human 18S rRNA (20×) (ABI) was used as an internal control. Total RNA extracted from MCF-7 cells was used for a standard curve. The reaction was performed with 50 ng total RNA in triplicate reactions in a 30 μl volume containing 2× p53 primer/probe and 1×18S rRNA primer/probe. Cycling conditions were 25° C. 10', 48° C. 30', 95° C. 10' and 40 cycles of 95° C. 15", 60° C. 1' for amplification. The results were analyzed by using SDS 2.2 software (ABI). For comparing total human endogenous p53 mRNA levels in cells, the amount of p53 mRNA level was normalized to the internal 18S rRNA level. For IP-RT-PCR, the absolute amount of human p53 mRNA level was used for analysis. The primers used for human p53 mRNA detection were: forward primer ATG CGA ATT CCT TCT CAA AAG TCT AGA GCC AC (SEQ ID NO: 33); reverse primer GTG AGC ATG CAT GGC AGT GAC CCG GAA GGC AGT C (SEQ ID NO: 34); the primers for 18S rRNA are commercially available from ABI.

For immunoprecipitations, 1 mg whole cell extract in RIPA buffer was cleared by protein A/G-PLUS agarose (Santa Cruz Biotechnology) and rabbit/mouse IgG (Sigma-Aldrich). Precleared lysates were incubated with anti-GFP antibody (Abcam), anti-flag antibody (M2, Sigma), anti-p53 antibody (FL393, Santa Cruz Biotechnology), anti-RPL26 antibody (Bethyl Laboratories, INC) or anti-nucleolin antibody (H250, Santa Cruz Biotechnology) overnight. Immunoprecipitated proteins were then washed extensively with lysis buffer and subjected to Western blot analysis as described above. For co-immunoprecipitations, cells were lysed in TGN buffer (50 mM Tris pH 7.5, 150 mM NaCl, 1% Tween-20, 0.2% NP-40, 50 mM NaF, 1 mM PMSF, plus protease inhibitors [complete mini cocktail; Roche Diagnostics, Indianapolis, Ind.]) and the rest of the procedure followed the immunoprecipitation protocol.

RNAse Digestion Assay and RNA-EMSA.

In vitro transcribed RNA was 5' end labeled using the KinaseMax™ (Ambion) 5' endlabeling kit. 40-80 ng labeled RNA was incubated with indicated amounts of oligonucleotides at 30° C. for 30' in 1× digestion buffer. After these pretreatment(s), RNase A (0.1 μg/ml) or Rnase T1 (0.1 U/μl) (Ambion) was incubated with the reaction mixture at RT for 15'. After digestion, RNA was precipitated, resuspended, and separated in precast 15% UREA-TBE PAGE gel (Invitrogen), and the gel was dried at 60° C. for 2 hrs and then subjected to autoradiography. RNA-EMSA protocol was adopted from www.vaxron.com and the labeled RNA was incubated with indicated proteins or antibodies at ambient temperature for 15' and separated on 3.5% native PAGE gel and the gel was then dried at 80° C. for 2 hrs before autoradiography.

RNase VI Partial Digestion/Primer Extension Experiment.

Oligonucleotide primer for primer extension and sequencing reaction was 5' end-labeled using the KinaseMax (Ambion) 5' end-labeling kit and purified through MEGAClear column (Ambion). One microgram of in vitro synthesized RNA was digested by 10× or 14× dilution of stock RNase VI (0.1 U/μl) for 15 min at room temperature based on the manufacturer's instructions (Ambion). The reaction was stopped by phenol/chloroform extraction followed by ethanol precipitation. The pellet of cleaved RNA was dissolved in 10 μl of DEPC-treated water for primer extension using SuperScript III first strand cDNA synthesis kit (Invitrogen). The primer extension products were concentrated by ethanol precipitation. For orientation of the cleavage products to the sequence, sequencing reactions were performed with the USB Sequenase version 2.0 DNA sequencing kit (Amersham). The template for sequencing was pLPCX plasmid with full-length human p53 cDNA. Both the sequencing products and reverse transcripts were separated in precast 15% UREA-TBE PAGE gel (Invitrogen) and then transferred to a nylon membrane before autoradiography.

Example 1 p53 mRNA Contains a Double-Strand RNA Structure with Base-Pairing Between the 5' and 3'-UTRs An RNAfold program (tbi.univie.ac.at/RNA/ on the World Wide Web) was used to predict the minimum-free-energy secondary structure of human p53 mRNA. The analysis predicted a structure containing a 21-18 (5'-3') base complementary region between the two UTRs. Specifically, the predicted double strand RNA structure (FIG. 1A; other species are shown in FIG. 1B) included 5'-UTR sequences −54 to −34 (numbering from the start codon) and 3'-UTR sequences +335 to +352 (numbering after the stop codon).

To determine if such a 5'-3' UTR double-strand RNA structure existed in p53 mRNA, human p53 mRNA was probed with single-strand-specific RNase enzymes. RNaseA specifically recognizes single-strand RNA (ssRNA) and cuts at the 3' side of C/U bases while RNAse T1 cuts at the 3' side of G bases in ssRNA. The vast majority of cellular p53 mRNA contains 5'-UTRs with 140-170 bases (Takagi et al., 2005), so a p53 mRNA containing 145 bases of the 5'-UTR and either containing or lacking a full length 3'-UTR was transcribed in vitro, end-labeled at the 5' end with 32P, and digested with RNaseA or RNAse T1. Wild type p53 or mutated p53 mRNA containing a 145 base 5'-UTR and coding sequence without (Δ3') or with a full-length 3'-UTR were in vitro transcribed, 5' end-labeled with $^{32}$P and subjected to RNase A digestion (0.1 μg/ml), and the digestion products were separated on a 15% Urea-TBE PAGE gel. The wild type sequence used had a wild type UTR (human p53 mRNA, SEQ ID NO: 35); the Δ3 sequence was a mutated p53 mRNA containing a wild type 145 base 5'-UTR and a coding sequence without a full-length 3'-UTR (SEQ ID NO: 50); another sequence, SEQ ID NO: 45, had a wild type 5'-UTR and 3'-UTR with mutation 1; and another sequence, SEQ ID NO: 46, had a 5'-UTR with mutation 1 and wild type 3'-UTR. Cutting was observed at the U(−36) position in the 5'-UTR; thus, the p53 3'-UTR sequence promoted a double-strand RNA structure in the p53 5'-UTR.

In addition, a 21-base oligonucleotide complementary to the 5'-UTR (5'-AS; SEQ ID NO: 14) was sufficient to restore the RNA double-strand structure at U(−36). p53 mRNA lacking the 3'-UTR ("Δ3'UTR") and containing a wild-type (SEQ ID NO: 52) or mutated (mutation 1) (SEQ ID NO: 53) 75 base 5'-UTR and a p53 coding sequence was in vitro transcribed, 5' end-labeled with $^{32}$P, and subjected to RNase A digestion (0.1 μg/ml). Cutting was observed at the U(−36) position in the 5'-UTR. A control oligonucleotide (SEQ ID NO: 25) complementary to a 5'-UTR sequence outside of the predicted interactive region (−74 to −53) also was used. The digestion products were separated on a 15% Urea-TBE PAGE gel.

RNaseA treatment of end-labeled human p53 mRNAs lacking a 3'-UTR resulted in a prominent band on a sequencing gel at a molecular weight consistent with cutting next to the uridine at position −36 in the 5'-UTR (U−36). In contrast, RNaseA failed to cut at the 5' UTR site if the RNA was mutated at U−36 (UGG to AAA, −36 to −34) (sequence identified as SEQ ID NO: 53), thus confirming the site of RNaseA cutting. Addition of a full-length 3'-UTR sequence to the p53 mRNA (SEQ ID NO: 36) blocked RNaseA cutting at U−36, consistent with the appearance of a double strand RNA structure at this 5'-UTR site when the 3'-UTR is included in the p53 mRNA. Mutating as few as three bases in the predicted interacting region of the 3'-UTR, which should disrupt the base pairing of the two UTRs at this site, was sufficient to partially restore RNaseA cutting at this 5'-UTR site, mutant W1 (SEQ ID NO: 45). RNaseA cutting at U−36 of a p53 mRNA lacking a 3'-UTR could even be abrogated by simple addition of an oligonucleotide complementary to the predicted 5'-UTR interacting region (5'-AS; SEQ ID NO: 14), as would be expected from the creation of a double strand RNA structure at this site. Importantly, addition of a control oligonucleotide (3' ctrl1: TCGTGGAAAGCACGCTC-CCAGC (SEQ ID NO: 25)), which would not pair with this 5'-UTR region failed to abrogate RNaseA cutting at this site in the p53 mRNA lacking the 3'-UTR (SEQ ID NO: 52).

Experiments were performed to demonstrate that the p53 3'-UTR sequence promotes a double-strand RNA structure in the p53. In these experiments, 5'-UTR wild type (WT) (SEQ ID NO: 35) or mutated p53 mRNA containing a 145 base 5'-UTR and coding sequence without (Δ3') (SEQ ID NO: 45) or with a full length 3'-UTR (SEQ ID NO: 46) were in vitro transcribed, 5' end-labeled with $^{32}$P and subjected to RNase T1 digestion (0.1 U/μl). The digestion products were then separated on a 15% Urea-TBE PAGE gel. The separation of digestion products indicated cutting at the G(−34/−35) position in a p53 mRNA lacking the 3'-UTR SEQ ID NO: 50) and a full-length p53 mRNA mutated at the 3'-UTR interacting site (W1 (SEQ ID NO: 45) AND 1W (SEQ ID NO: 46)), but failed to cut full-length, wild-type p53 mRNA (SEQ ID NO: 35). Thus, this data similarly supports the existence of a doublestrand RNA structure at this site.

The p53 5'-UTR sequence promotes a dsRNA structure in the p53 5'-UTR. Wild-type p53 mRNA containing a 145-base 5'-UTR and coding sequence without or with a full-length 3'-UTR were in vitro transcribed and subjected to RNase VI digestion (0.1 U/μl) followed by reverse transcription (primer extension). RNase VI was diluted 10-fold (0.01 U/μl) or 14-fold (0.007 U/μl). Sequencing and cleavage/primer extension reactions were performed with an oligonucleotide primer complementary to the p53 coding sequence close to the 3' end of the ATG start codon (+2 to +24). Sequencing reaction products and primer extension products were separated on a 15% Urea-TBE PAGE gel. A cleavage product of the expected size was produced due to cleavage within the predicted dsRNA region (seen only with partial cleavage), and a cleavage product also was produced by cutting out the entire predicted dsRNA structure, both seen only in the presence of the 3'-UTR.

Example 2

Figure 2A:
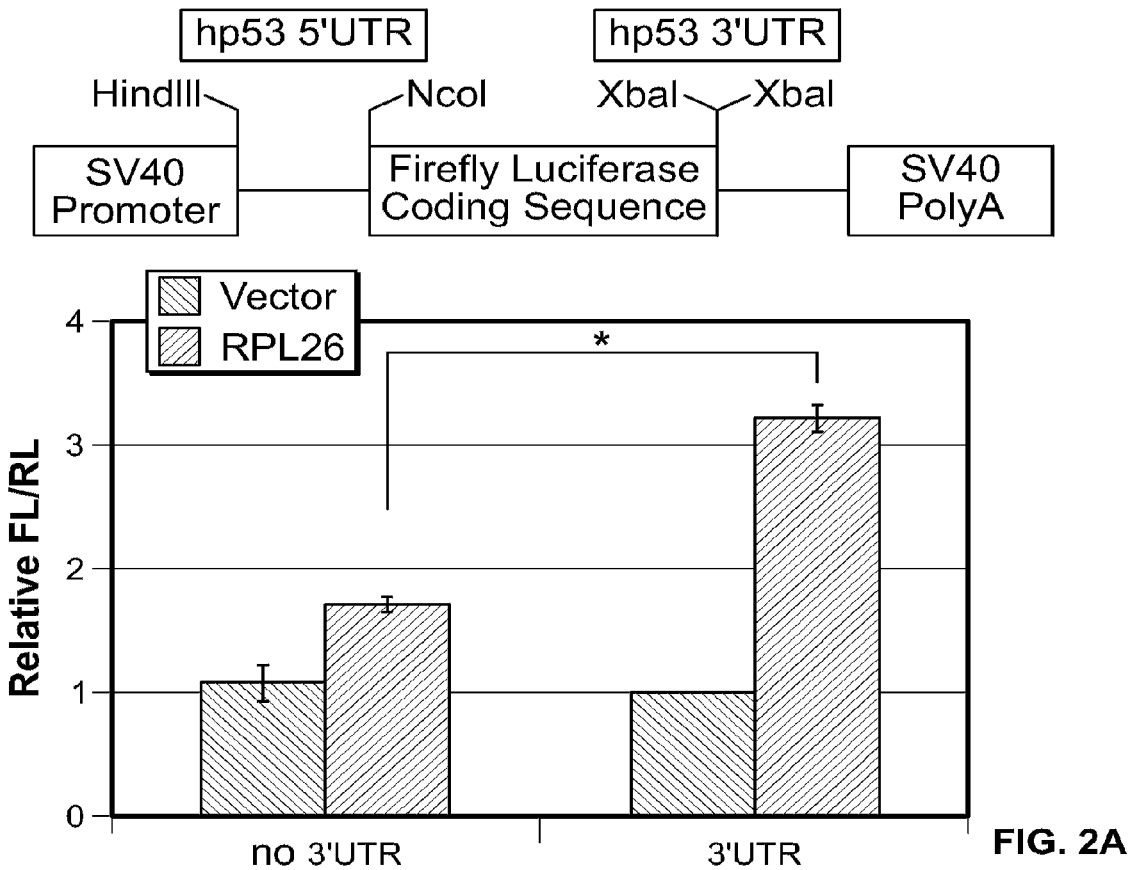
FIGS. 2A-2C demonstrate that the 5',3'-UTR double-strand RNA structure is required for optimal RPL26 stimulation of p53 translation. A. The 3'-UTR sequence is required for optimal RPL26 stimulation of a reporter gene containing the p53 UTRs. MCF-7 cells were transiently transfected with empty vector (vector) or Flag-RPL26 (RPL26) together with firefly luciferase constructs (FL) as illustrated in the schematic diagram, plus a control renilla luciferase expression construct (RL). The relative FL/RL ratio was calculated by normalizing the FL/RL ratio of each sample to the ratio in cells transfected with empty vector (instead of RPL26), renilla luciferase, and the firefly luciferase construct containing a 145 base 5'-UTR and full length 3'-UTR of human p53 (from SEQ ID NO: 35). Data shown are average±SD for three independent experiments. *p=0.004 (Student's T test). B. Mutations inside the UTR interacting region modulate p53 reporter gene induction by RPL26. Mutations were introduced into the 5'-UTR (1W) (SEQ ID NO: 46), 3'-UTR (W1) (SEQ ID NO: 45) or both (double mutant, DM) (SEQ ID NO: 47), including a compensatory mutation (1C) (SEQ ID NO: 44) that restores complementarity or an identical 5'-UTR control mutation (ctrl mut) upstream (−64 to −62) of the UTR interacting region (SEQ ID NO: 48). The dual luciferase reporter assay was performed as in FIG. 2A. Data shown are average±SD for three independent experiments. P values were calculated using Student's T test. C. Mutations inside the UTR interacting region affect binding of RPL26 protein to human p53 mRNA in cells. In vitro transcribed wild-type or mutated p53 mRNAs with 5' cap and 3' polyadenylation modifications were transfected into H1299 cells (WT (SEQ ID NO: 35), W1 (SEQ ID NO: 45), 1W (SEQ ID NO: 46), double mutant (DM) (SEQ ID NO: 47), 1C (SEQ ID NO: 44), "ctrl mut" (SEQ ID NO: 48)). 16 hrs post-transfection endogenous RPL26 was immunoprecipitated and the bound p53 mRNA was measured by real time RT-PCR. The bar graphs show the ratio of the bound p53 mRNA level compared to that seen in cells with wild type p53 mRNA. The error bars represent average±SD for three experiments. P values were calculated using Student's T test.
Figure 2B:
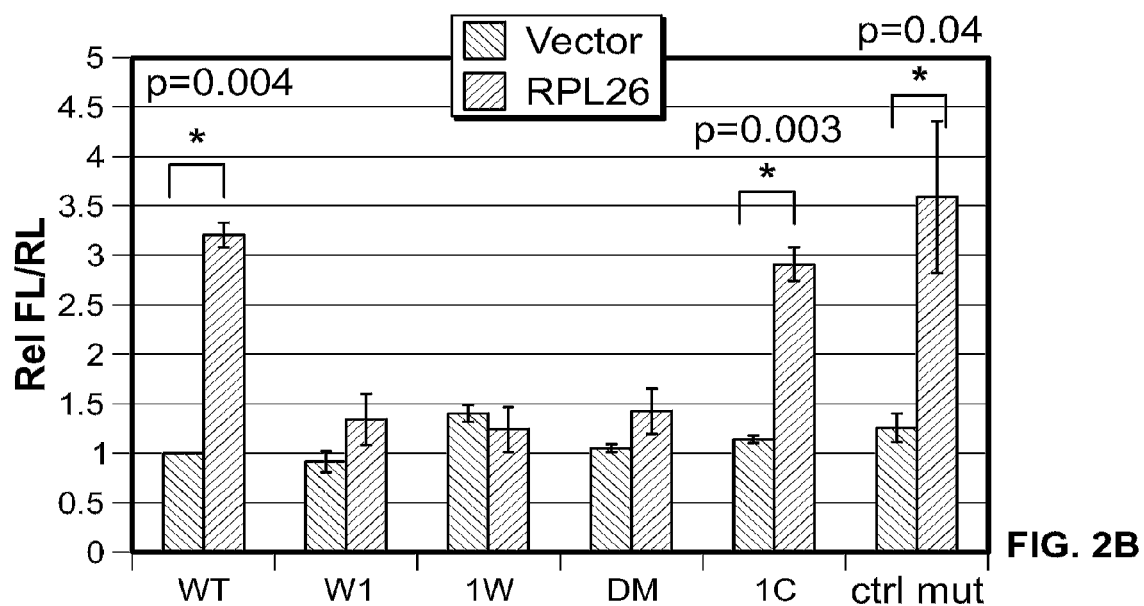

The 5'-UTR, 3'-UTR Base Pairing Region is Required for RPL26 Modulation of p53 Translation RPL26 stimulation of p53 translation requires the 5'-UTR, but not the coding sequence, of p53 mRNA (Takagi et al., 2005; Ofir-Rosenfeld et al., 2008). This 5'-UTR translational dependence was recapitulated by a cell-based, dual luciferase reporter assay, in which RPL26 selectively enhanced the expression of a chimera firefly luciferase reporter gene containing a 5' UTR sequence of human p53 mRNA relative to the expression of the internal control renilla luciferase gene (FIG. 2A). Unexpectedly, adding the 3'UTR sequence of human p53 mRNA further enhanced RPL26 stimulation of firefly luciferase expression (FIG. 2A). Since both UTRs seem to affect the translational regulation of p53 by RPL26 and since a region of base pairing between the UTRs had been identified, it was determined whether these UTR interactions affect RPL26-mediated regulation of p53 translation. Mutating the last three bases of the interacting region in either the 5' UTR (1W, UGG to AAA (SEQ ID NO: 46)), 3' UTR (W1, CCA to UUU (SEQ ID NO: 45)) or both (double mutant, DM, 5' UGG to AAA, 3' CCA to AAA (SEQ ID NO: 47)) abolished the stimulation of the reporter by RPL26 (FIG. 2B). The same mutations introduced into an upstream site in the 5'UTR outside of the interacting region (−64 to −62, 5' UGC to AAA) did not affect the ability of RPL26 to stimulate luciferase activity (FIG. 2B, ctrl mut). A compensatory double mutation that should restore the base pairing of the last three bases (1C, 5' UGG to AAA, 3' CCA to UUU) restored the ability of the reporter to respond to RPL26 regulation. None of the mutations affected basal reporter activity, thus none of the manipulations affected levels of reporter RNA in the assay. These results suggest that interaction of the last three base pairs of the UTR-interacting region are particularly important in regulating the translation of p53 mRNA by RPL26.

Figure 2C:
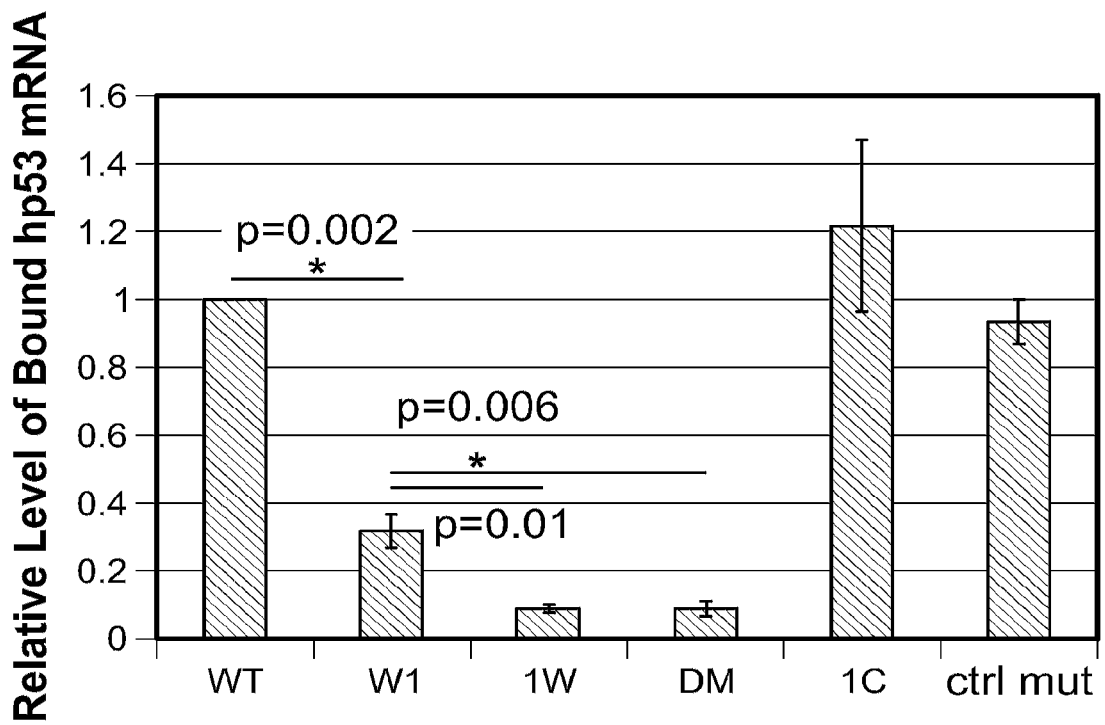

RPL26 binds to p53 mRNA in cells after DNA damage and stimulates its translation (Takagi et al., 2005; Ofir-Rosenfeld et al., 2008). It is notable that RPL26 binds to p53 mRNA in the nucleus after damage (FIG. 5), suggesting that these effects represent an extraribosomal function of RPL26. The role of this UTR interacting region in modulating the ability of RPL26 to bind to p53 mRNA was examined Wild-type or mutant p53 mRNAs were transcribed in vitro, transfected into p53-null H1299 cells, and the ability of endogenous RPL26 protein to bind to p53 mRNA was assessed. Though RPL26 bound to p53 mRNA with wild-type UTR sequences, it failed to bind p53 mRNA with mutations that disrupt the interactions of the last three base pairs (FIG. 2C), whether the mutations were in the 3'-UTR (W1) (3' UTR with mutation 1 (SEQ ID NO: 45), 5'-UTR (1W) (SEQ ID NO: 46), or both (DM) (SEQ ID NO: 47). Consistent with the reporter assay (FIG. 2B), compensatory mutations (1C) (SEQ ID NO: 44) rescued the binding of RPL26 to p53 mRNA, which confirms the dependence of RPL26 on the double strand structure at the position of these three base pairs for optimal binding to p53 mRNA. The slightly greater binding of RPL26 to the W1 mutant (3' mutation only) than to the 1W or DM mutants (FIG. 2C) is consistent with the low level stimulation of translation by RPL26 in an mRNA containing just the 5' UTR (FIG. 2A) and suggests a low level binding and stimulation associated with the 5' UTR sequence alone. These UTR mutations did not affect the levels of p53 mRNA in cells (FIG. 6), the basal p53 mRNA translation, or the level of RPL26 protein during the time frame of the study. Thus, the effects of RPL26 on reporter expression and p53 mRNA binding cannot be attributed to alterations in RNA transcription or stability.

Finally, mutations in the UTR interacting region affected the binding of RPL26 protein to human p53 mRNA in vitro. RNA-EMSA was performed to detect the binding of recombinant RPL26 protein (amino acids (aa) 45-145) to in vitro transcribed, 5'-end $^{32}$P labeled wild-type or mutated p53 mRNA with a 145 base 5'-UTR and full length 3'-UTR. In addition, antibody raised against the N terminus (N) or C terminus (C) of RPL26 protein was used for the supershift experiments. This data demonstrated that purified, recombinant RPL26 protein is able to directly bind to p53 mRNA in vitro, and that this binding is abrogated by mutating the 5'-3' UTR interacting region (DM) and is restored by compensatory mutations (1C) that restore complementarity of this region.

Example 3

Disruption of the UTR Interacting Region Affects Damage Induction of p53 in Cells In order to explore the role of the 5'- and 3'-UTR base-pairing sequences in regulating p53 translation and p53 induction after DNA damage in cells, an attempt was made to disrupt the 5'-3' UTR interaction by transfecting 21-base, single-strand oligonucleotides complementary to either the 5' or 3' UTR interacting sequences into MCF-7 cells and examining potential effects of these oligonucleotides on p53 induction after DNA damage. MCF-7 cells were transfected with 21-base oligonucleotides using LipofectamineRNAiMAX or Lipofectamine 2000 (Invitrogen). Oligonucleotides were complementary to the interacting sequences of the 3'-UTR (5' oligo; SEQ ID NO: 13), the 5'-UTR (5'-AS; SEQ ID NO: 14), or UTR sequences from nearby surrounding regions: 5' ctrl1 (SEQ ID NO: 23); 5' ctrl2 (SEQ ID NO: 24); 3' ctrl1 (SEQ ID NO: 25); and 3' ctrl2 (SEQ ID NO: 26). 24 hrs post-transfection, MCF-7 cells were irradiated (0 or 5Gy IR), harvested 30 minutes later, and immunoblotted for p53 and NCL proteins. Introduction of oligonucleotides complementary to either the 3'-UTR sequence, or 5'-UTR sequence, but not control oligonucleotides blocked induction of endogenous p53 following ionizing irradiation (IR). The inhibitory effects of complementary oligonucleotides which can bind either the 5' or 3' UTR sequences are consistent with a model in which this UTR interacting region is important for p53 regulation.

In order to determine the optimal or minimal oligonucleotide sequence length required for this inhibition, serial deletions were made by progressively shortening the interfering oligonucleotides by 3 bases on either end of the 5' oligonucleotide sequence (complementary to the 3' interactive sequence). p53 induction 30 minutes after 5Gy IR was assessed in MCF-7 cells transfected with various oligonucleotides. 5' oligo: (SEQ ID NO: 13): 21 nt 5'-UTR interacting sequence; F18: GAC GGT GAC ACG CTT CCC (SEQ ID NO: 20): the first 18 bases of 21 nt 5' oligo. L18: GGT GAC ACG CTT CCC TGG (SEQ ID NO: 11): the last 18 bases of 21 nt 5' oligo; F15: GGT GAC ACG CTT CCC (SEQ ID NO: 18): the first 15 bases of L18; L15: GAC ACG CTT CCC TGG (SEQ ID NO: 9): the last 15 bases of L18. Luc21: ACC AGG GCG TAT CTC TTC ATA (SEQ ID NO: 22), luc18: AGG GCG TAT CTC TTC ATA (SEQ ID NO: 21), and luc15: AGG GCG TAT CTC TTC (SEQ ID NO: 19) were oligonucleotides of luciferase coding sequence with indicated length. These results demonstrated that a 15 base region of 5'-UTR oligo (L15) is sufficient to block p53 induction by IR.

In addition, MCF-7 cells were transfected with shorter oligonucleotides generated by serial deletion of L15 from the 5' end (L12: ACG CTT CCC TGG (SEQ ID NO: 7), L9: CTT CCC TGG (SEQ ID NO: 5), L8: TTC CCT GG (SEQ ID NO: 3), L7: TCC CTG G (SEQ ID NO: 1) for 24 hours. p53 induction was assessed in transfected cells 30 minutes after 5 Gy IR. Oligonucleotides (F12: GGT GAC ACG CTT (SEQ ID NO: 32), F9: GGT GAC ACG (SEQ ID NO: 31)) generated by deletion from the 3' end of F15 were used as controls. These results indicated that small oligonucleotides can block IR induction of p53. Also, 40 µM oligonucleotides were incubated with MCF-7 cells for 24 hours prior to 0 or 5Gy IR and p53 induction was assessed after 30 minutes. This experiment demonstrated that L15 can enter cells and block p53 induction in the absence of transfection. Further, p53 induction was assessed 24 hours after addition of F15, L15, or mutated L15 ("L15 m") to MCF-7 cultures and 30 minutes after 0 or 5 Gy IR. The sequences of mutated L15 were as follows: L15 m1: TTT ACG CTT CCC TGG (SEQ ID NO: 15), L15 m2: GAC ACA ACC AAC TGG (SEQ ID NO: 16), L15m3: GAC ACG CTT CCC AAA (SEQ ID NO: 17). These experiments demonstrated that point mutations in L15 abolish its blocking effect on p53 induction. Lastly, GFP and GFP-RPL26 were transfected into MCF-7 cells and L15 was added to the medium 6 hours later. p53 levels were assessed 24 hrs post-transfection. These experiments demonstrated that L15 blocks RPL26 induction of p53. While oligonucleotides containing the last bases in the 5'-UTR interactive sequences (L18: GGT GAC ACG CTT CCC TGG (SEQ ID NO: 11), L15: GAC ACG CTT CCC TGG (SEQ ID NO: 9), L12: ACG CTT CCC TGG (SEQ ID NO: 7), L9: CTT CCC TGG (SEQ ID NO: 5)) retained full inhibitory activity, removal of the last 3 bases in each case (F18: GAC GGT GAC ACG CTT CCC (SEQ ID NO: 20), F15: GGT GAC ACG CTT CCC (SEQ ID NO: 18), F12: GGT GAC ACG CTT (SEQ ID NO: 32), F9:

GGT GAC ACG (SEQ ID NO: 31)) abrogated inhibitory activity. It is noted that F18 and L18, for example, have significant sequence overlap, sharing 15 out of 18 bases in common, but exhibit markedly different activities in these assays. As long as the final three bases in the sequence were preserved, oligonucleotides as short as 7-8 bases (L8: TTC CCT GG (SEQ ID NO: 3), L7: TCC CTG G (SEQ ID NO: 1)) could blunt p53 induction after IR.

Figure 7A:
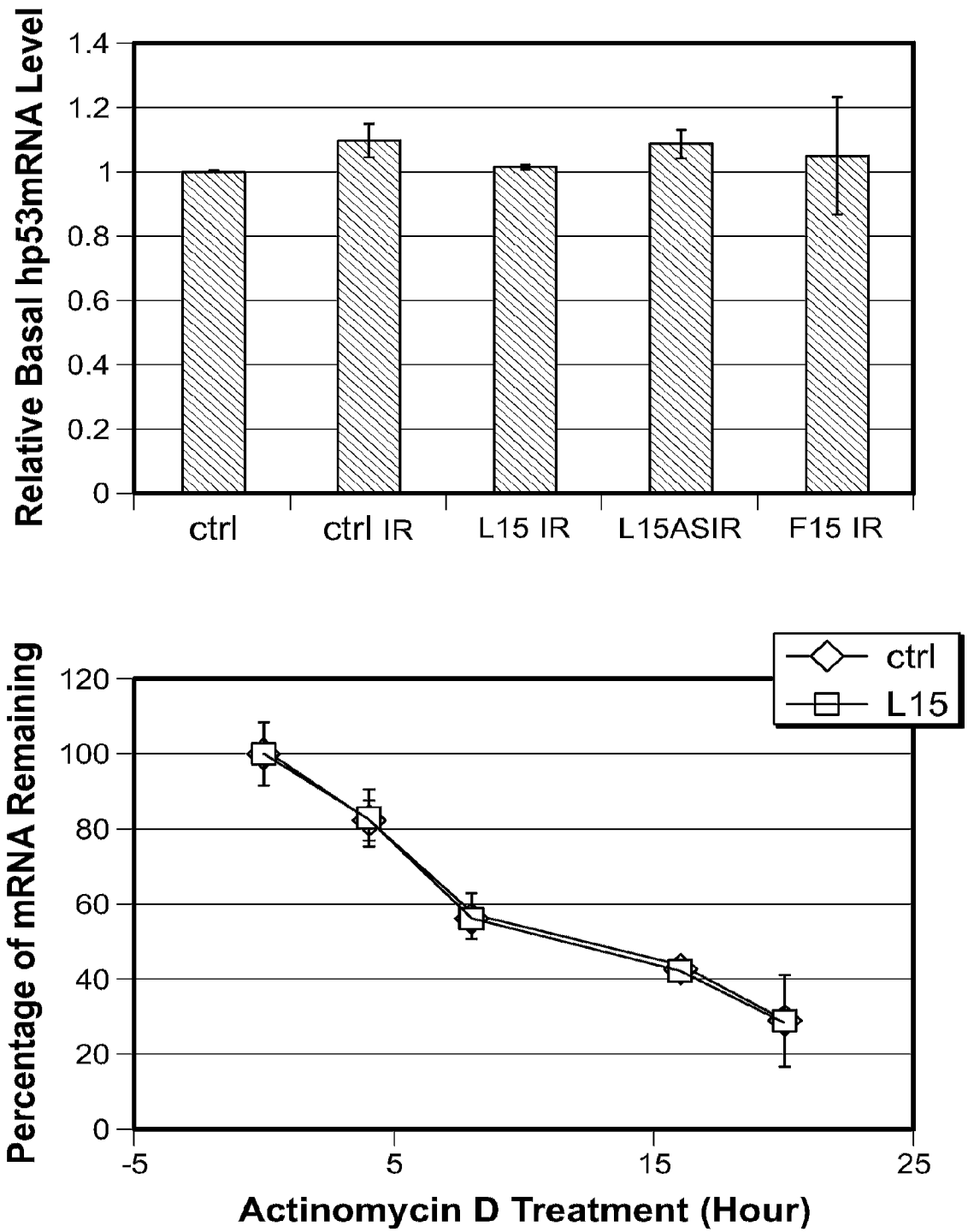
FIGS. 7A-7B demonstrate that UTR-targeted oligonucleotides have no effect on p53 mRNA level or half-life or p53 protein half-life. A. L15 has no effect on p53 mRNA level or half-life. In the left panel, real time RT-PCR was performed 30 minutes after 0 or 5 Gy IR to measure endogenous p53 mRNA level in MCF-7 cells that had been transfected with 40 µM of the indicated oligonucleotides 24 hrs earlier. In the right panel, MCF-7 cells were transfected with 40 µM L15: GACACGCTTCCCTGG (SEQ ID NO: 9) for 4 hrs before exposure to 5 µg/ml Actinomycin. p53 mRNA level was detected 4, 8, 16 and 20 hrs post treatment by real time RT-PCR. The error bars in both panels represent average±SD for three independent experiments. B. L15 has no effect on p53 mRNA level, but blocks enhanced RPL26 binding to p53 mRNA after IR. In the left panel, real time RT-PCR was performed 30 minutes after 0 or 10 Gy IR to measure endogenous p53 mRNA level in MCF-7 cells that had been transfected with 40 µM of the indicated oligonucleotides 24 hours earlier. Endogenous RPL26 was also immunoprecipitated from these cells and p53 mRNA bound to RPL26 was quantified by real-time RT-PCR (right panel). The bar graphs in both panels represent average±SD for three independent experiments.

Importantly, addition of the oligonucleotides caused no changes in the basal levels of p53 mRNA in cells, with or without IR, and no changes of the half life of p53 mRNA (FIG. 7A). Fifteen base oligonucleotides are short enough to have the potential to enter cells without transfection and simple incubation of the L15 oligonucleotide with cultured MCF-7 cells was able to reduce p53 induction after IR. Thus, L15 is therefore useful as an inhibitor of p53 induction.

The importance of the last three bases in these oligonucleotide sequences in blocking p53 induction in cells was reminiscent of the importance of these same three bases in translational regulation of p53 reporters carrying full length p53 UTRs in the dual luciferase reporter assay (FIG. 2B) and in determining the binding of RPL26 protein to p53 mRNA in cells (FIG. 2C) or in vitro. To further explore the importance of these last three bases in the interacting sequence, mutant oligonucleotides were generated and tested for their ability to blunt p53 induction after DNA damage in cells. While L15 (GAC ACG CTT CCC TGG (SEQ ID NO: 9)) oligonucleotides containing mutations of either the first three (m1) or middle six (m2) bases of the critical sequence partially lost inhibitory activity, mutation of the last three bases (m3) abrogated all inhibitory activity. The sequences of mutated L15 were as follows: L 15 m1: TTT ACG CTT CCC TGG (SEQ ID NO: 15), L15 m2: GAC ACA ACC AAC TGG (SEQ ID NO: 16), L15 m3: GAC ACG CTT CCC AAA (SEQ ID NO: 17).

Figure 5:
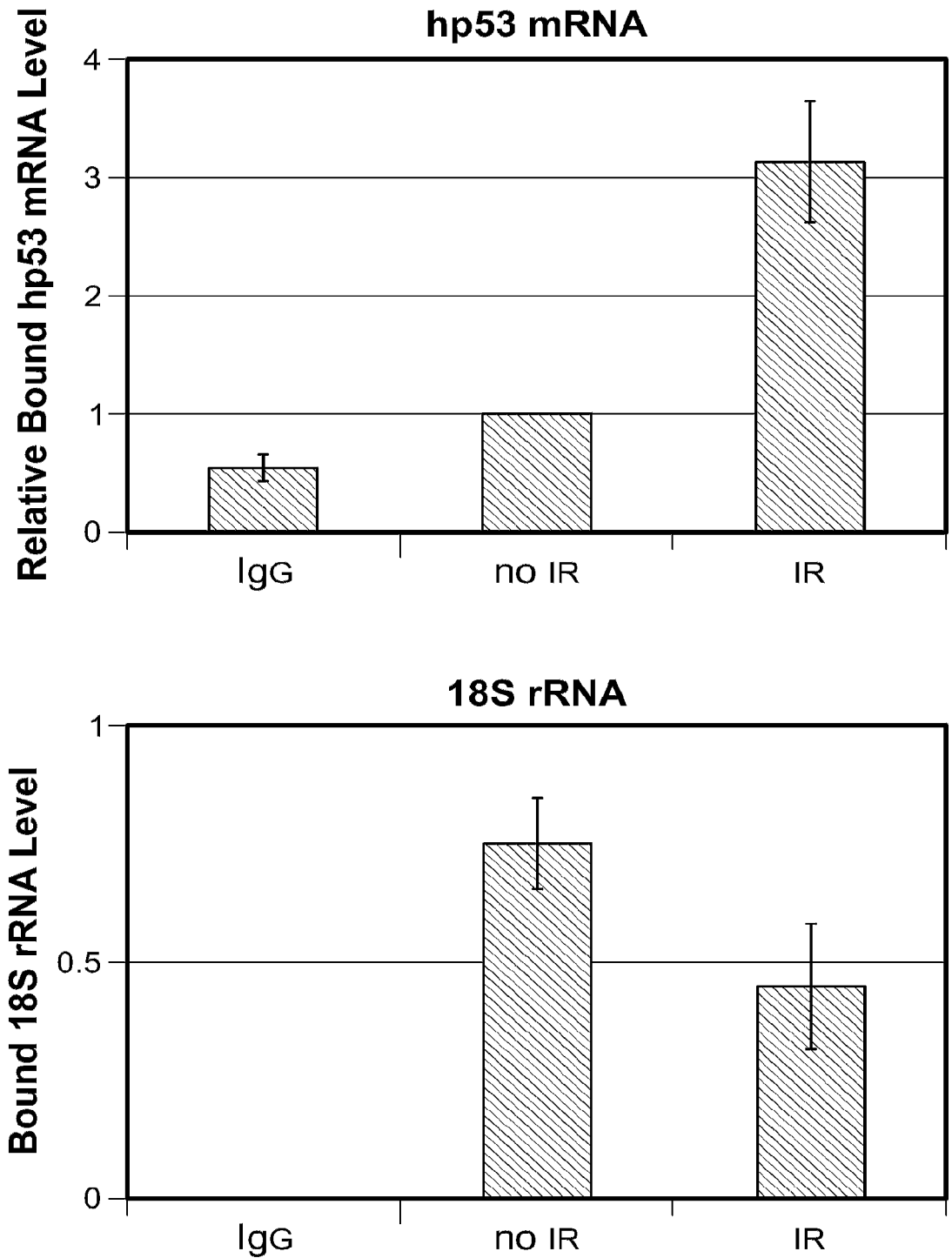
FIG. 5 demonstrates that RPL26 binds human p53 mRNA in the nucleus. Enhanced binding of RPL26 to p53 mRNA in the nucleus after IR. Nuclear fractions were prepared from control or irradiated (10 Gy, 30 min) MCF-7 cells. RPL26 protein was immunoprecipitated from the fraction and the bound human p53 mRNA (left panel) and 18S ribosomal RNA (right panel) were detected by real time RT-PCR.
Figure 6:
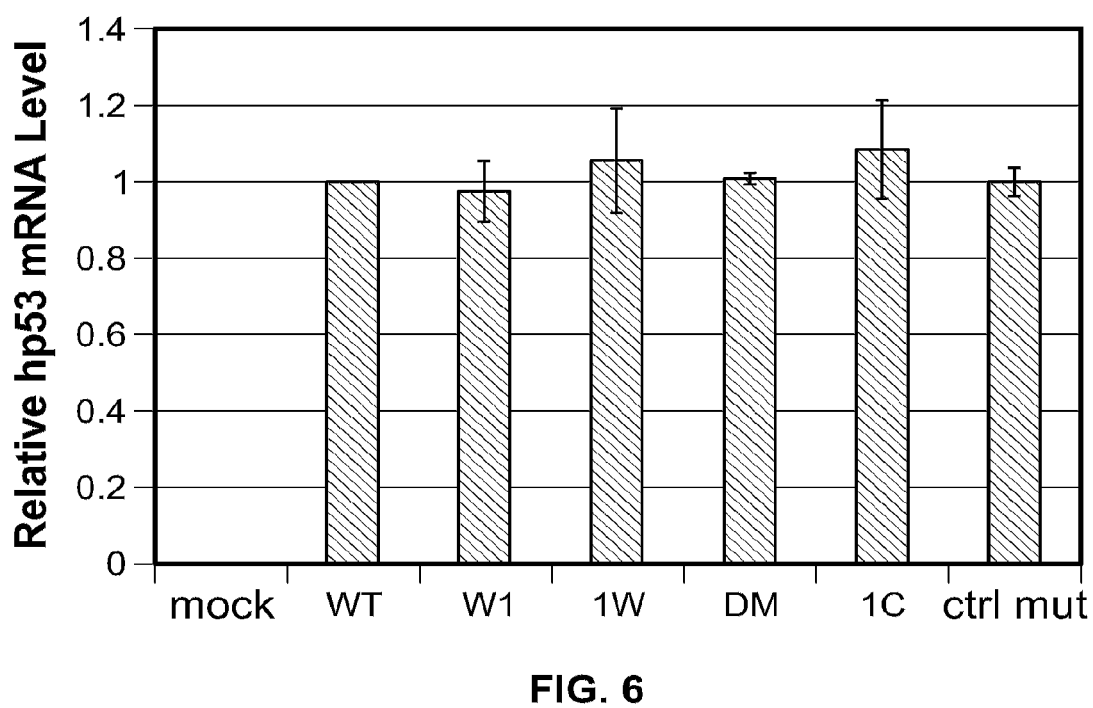
FIG. 6 demonstrates that mutations in the p53 UTR interacting regions have no effect on p53 mRNA or basal protein level. In vitro transcribed wild type or mutated p53 mRNAs with 5' cap and 3' polyadenylation modifications were transfected into H1299 cells. 16 hrs post-transfection endogenous p53 mRNA levels were assessed by real time RT-PCR.

Optimal IR-induced increases in p53 protein levels are dependent on increases in p53 protein translation and require the binding of RPL26 to the 5'-UTR of p53 mRNA (Takagi et al., 2005; Ofir-Rosenfeld et al., 2008). Similar to its blocking effects on p53 induction following IR, addition of L15 (GAC ACG CTT CCC TGG (SEQ ID NO: 9)) to cells blunted p53 induction directly induced by overexpression of RPL26. Along with the observation that disruption of the UTR interacting sequence by mutation could disrupt the binding of RPL26 to p53 mRNA (FIG. 2C), this observation suggested that the ability of the oligonucleotides to blunt p53 induction after IR could result from blockade of the binding of RPL26 to p53 mRNA. As previously noted (Takagi et al., 2005), RPL26 binding to endogenous p53 mRNA is detectable after IR by immunoprecipitation of RPL26 protein followed by real time RT-PCR to quantitate the amount of p53 mRNA bound to RPL26 (FIGS. 5 and 3).

Figure 3:
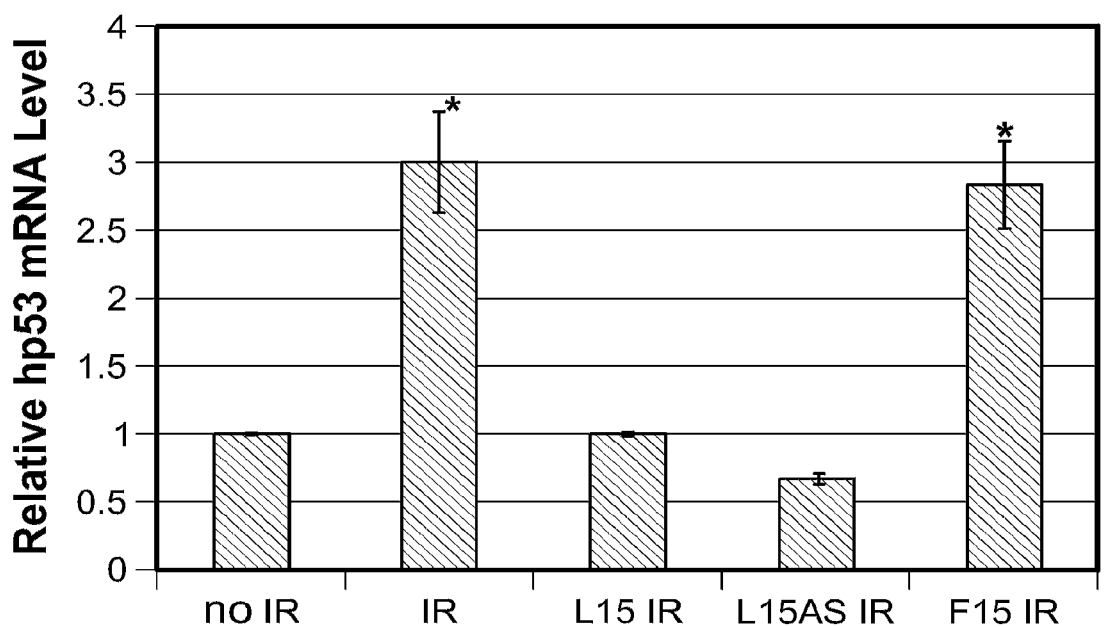
FIG. 3 demonstrates that oligonucleotides targeting the UTR interacting region inhibit p53 induction and RPL26 binding. L15 blocks the binding of RPL26 to p53 mRNA in irradiated cells. 30 minutes after 10 Gy IR, endogenous RPL26 was immunoprecipitated from MCF-7 cells that had been transfected with 40 µM of the indicated oligonucleotide 24 hrs earlier. p53 mRNA bound to RPL26 was quantified by real time RT-PCR. The bar graphs show the ratio of the p53 mRNA level to that in untreated cells. The error bars represent average±SD for three experiments. *p=0.01 (Student's T test).
Figure 7B:
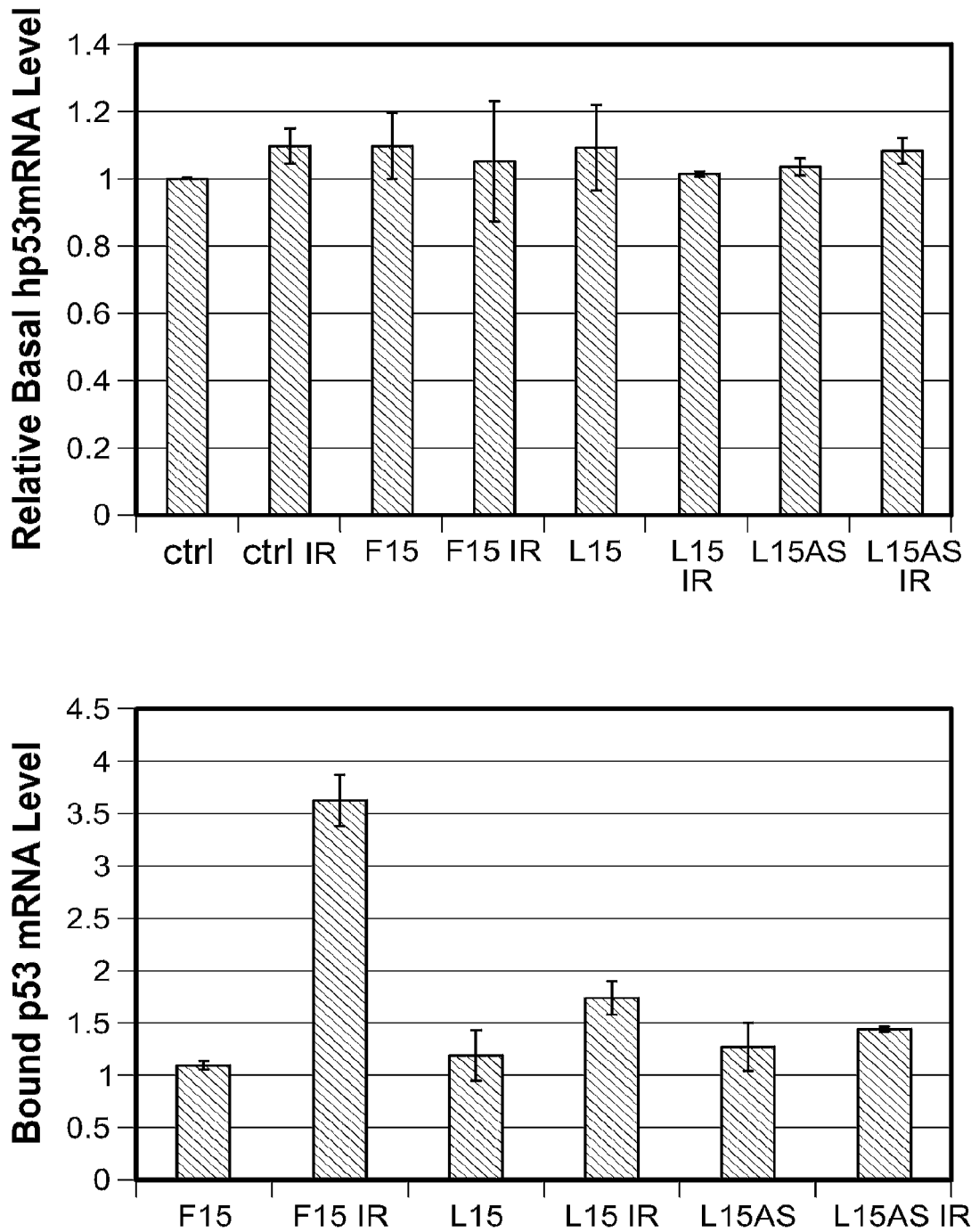
Figure 8:
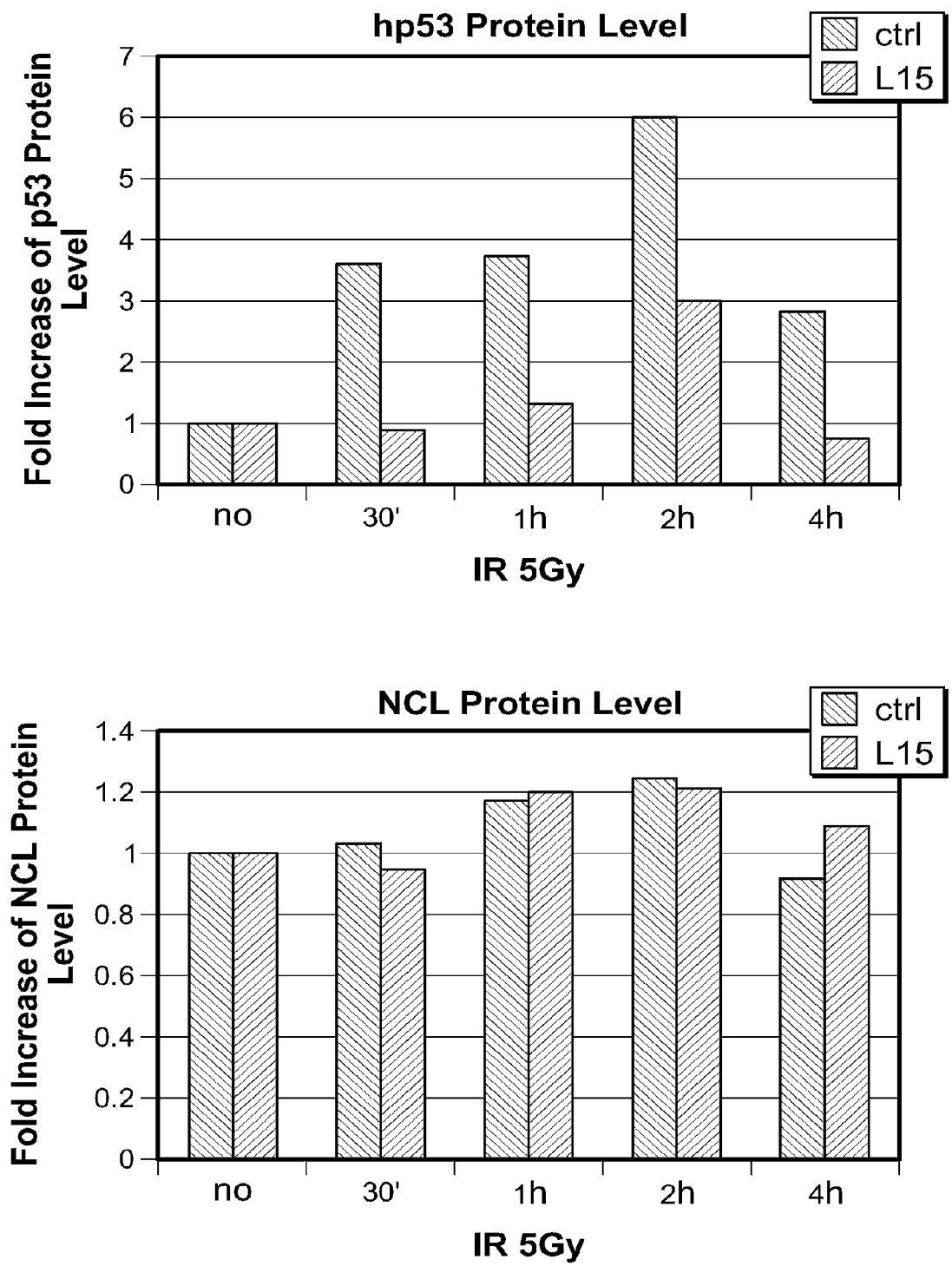
FIG. 8 demonstrates that oligonucleotides quantitatively reduce p53 induction by ionizing irradiation (IR). Quantification of p53 and nucleolin (NCL) protein levels based on blotting experiments. Band intensity was measured using NIH Image J program [http://rsbweb.nih.gov/ij/]. The graph shows the ratio of the band intensity of p53 (left panel) or NCL (right panel) in IR-treated samples at each time point compared to the untreated samples.

Identical to the results seen with p53 induction after IR, transfection of cells with L15 (GAC ACG CTT CCC TGG (SEQ ID NO: 9)), but not the control F15 (GGT GAC ACG CTT CCC (SEQ ID NO: 18)) oligonucleotide, blocked the enhanced binding of RPL26 to p53 mRNA in IR-treated cells (FIG. 3, FIG. 7B right panel). Addition of a 15-base oligonucleotide mimicking the 3'-UTR interacting sequence (L15-AS: CCA GGG AAG CGT GTC (SEQ ID NO: 10)) also blocked RPL26 binding to p53 mRNA. There were no differences in the input total p53 mRNA level in these experiments (FIG. 7B, left panel). These data, together with the studies described above, demonstrate that disruption of the interactions of the last three base pairs in the 5'-3' UTR interacting region, whether by introduction of mutations in the mRNA (FIG. 2C) or by introduction of interfering oligonucleotides (FIG. 3), abolishes the binding of RPL26 to p53 mRNA and blunts the translational induction of p53 by RPL26.

MCF-7 cells were transfected with L15 or control F15: GGT GAC ACG CTT CCC (SEQ ID NO: 18) oligonucleotide using Lipofectamine 2000 (Invitrogen) for 6 hours before administration of 10 μM Nutlin 3 (Cayman Chemical Co.). 24 hrs post transfection, cells were harvested and immunoblotted for p53 and RPL26 proteins. These experiments demonstrated that oligonucleotides have no effect on hdm2 modulation of p53 protein. Consistent with this model, it is important to note that L15 had no impact on p53 induction following Nutlin treatment, which induces p53 via increased p53 protein half-life by blocking Mdm2-mediated degradation of p53 protein.

The LNA-modified L15 (L15-LNA) DNA oligonucleotide inhibits p53 induction. p53 induction 30 min after 5 Gy IR was assessed in MCF-7 cells transfected with L15-LNA. LNA-modified F15 (F145-LNA) was used as a control. The band intensity of p53 in each lane was quantified and normalized to the band intensity of NCL and then compared with the F15-LNA transfected, no-IR-treated sample. In the presence of irradiation, the F15-LNA increased the p53 protein levels by 2.1-fold over the control, while the L15-LNA increased the p53 protein levels by 1.2-fold. In the absence of irradiation, the p53 protein levels were increased by 1 and 1.1-fold, respectively, for the L15-LNA and the F15-LNA.

Example 4

Reagents to Modulate Stress-Induction of p53 in Cells

MCF-7 cells were transfected with 40 μM L15 (GAC ACG CTT CCC TGG (SEQ ID NO: 9)) 20 hrs before exposure to 5 J/m2 UV and p53 induction was assessed 3 hours later. MCF-7 or HCT116 cells were transfected with L15 or L8: TTC CCT GG (SEQ ID NO: 3) for 4 hrs before administration of 100 μM fluorouracil (5-FU) (HCT116WT), 170 μM etoposide (ETO) (HCT116WT), 250 μM desferoxamine (DFO) (MCF-7), or 50 ng/ml methylmethanesulfonate (MMS) (MCF-7) for an additional 20 h, 48 h, 20 h, or 4 h incubation, respectively, and p53 induction was assessed by immunoblot. The control oligonucleotide used was F15. These experiments demonstrate that 5'-UTR oligonucleotides block p53 induction following many types of stress.

p53 protein is induced by many different types of DNA damage and other stresses (Giaccia and Kastan, 1998). Previously, it was demonstrated that down-regulation of RPL26 protein with an siRNA blocks p53 induction after either IR or UV irradiation (Takagi et al., 2005). Thus, it was determined whether these inhibitory oligonucleotides would block p53 induction following a variety of different stresses. Similar to their effects on IR-treated cells, oligonucleotides (L15 (SEQ ID NO: 8) and L8 (SEQ ID NO: 3)) reduced p53 induction after exposure to UV irradiation, alkylating agents (MMS), antimetabolites (5-FU), a topoisomerase II inhibitor (etoposide) (ETO), or a hypoxia-mimic (DFO). With all of the damaging agents, a quantitative reduction, rather than a complete inhibition, of p53 induction was seen with the oligonucleotide treatments. (FIG. 9).

Figure 4A:
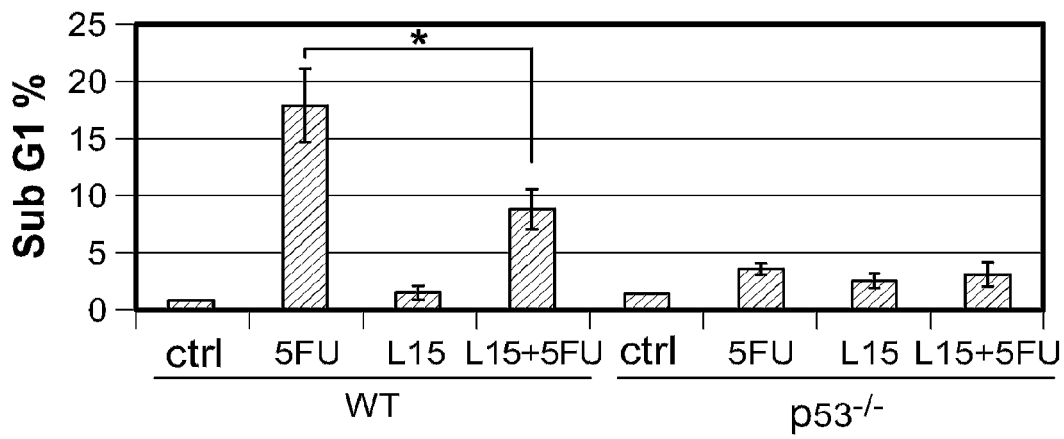
FIGS. 4A-4B demonstrate that oligonucleotides targeting the UTR interacting region can modulate stress induction of p53 and resultant cellular effects in cells. A. L15 attenuates p53-dependent cell death. p53 Wild type (WT) or p53 null (p53−/−) HCT116 cells were incubated with 40 µM L15 for 4 hrs before administration of 100 µM 5-FU for an additional 20 h incubation. Untreated (WT, p53−/−) and treated cells (WT+L15, p53−/−+L15) were subjected to PI staining. The subG1 cell population was counted and plotted. Data shown are average±SD for three independent experiments. *p=0.018 (WT vs WT+L15, Student's T test). B. L15 provides a p53-dependent selection advantage for cells following DNA damage. p53 Wild type (WT) or p53 null (p53−/−) HCT116 cells were transfected with 20 µM Fluorescein conjugated L15 or F15: GGTGACACGCTTCCC (SEQ ID NO: 18) (FAML15, FAM-F15) 4 hrs before administration of 170 µM Etoposide (ETO) and viable cells (PI negative) were assessed by FACS analysis one or two days later. The percentage of FAM+ viable cells was assessed at each time point and treatment condition and normalized to the percentage of FAM+ cells prior to ETO treatment. The right panel shows the fold increase of FAM+ viable cells in etoposide treated samples compared to untreated samples. Data shown are average±SD for three independent experiments.
Figure 4B:
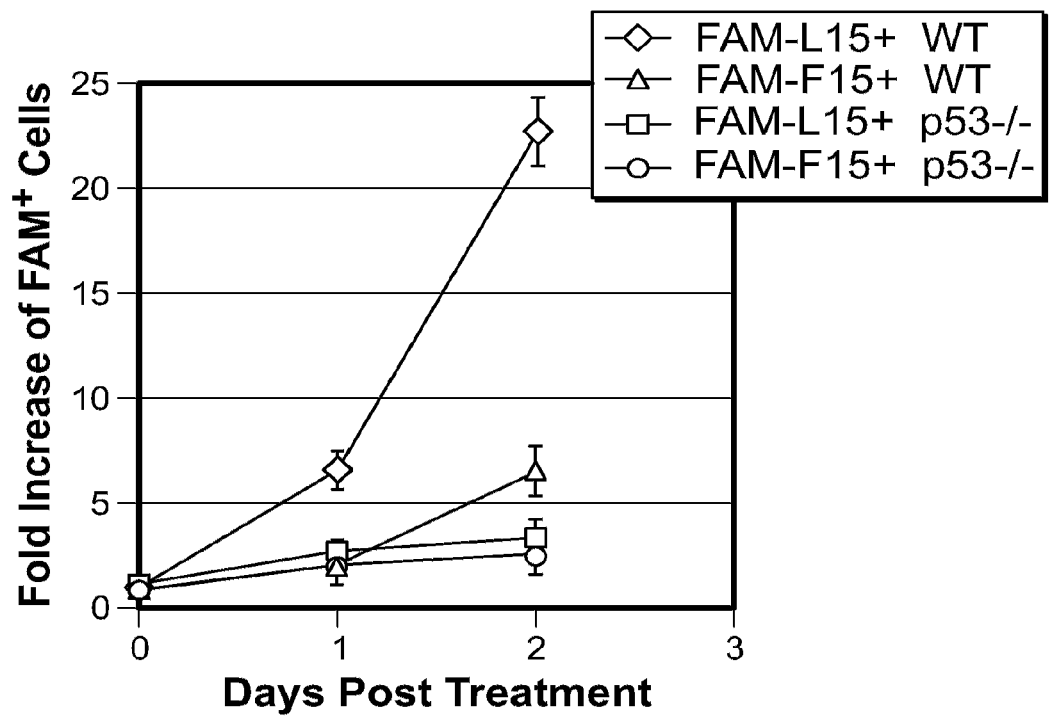

Since induction of p53 protein can lead to cell cycle arrest or cell death, the abilities of these oligonucleotides to block cell death following stress-induction of p53 was also examined. Treatment of p53-competent HCT116 cells with 5-fluorouracil (5-FU) induces a p53-dependent apoptotic cell death which can be blocked by down-regulation of RPL26 (Takagi et al., 2005). MCF-7 cells were transfected with 40 μM control oligo (F15: GGT GAC ACG CTT CCC (SEQ ID NO: 18)) or L15: GAC ACG CTT CCC TGG (SEQ ID NO: 9) 16 hrs before exposure to 5 Gy ionizing irradiation (IR) treatment. p53 induction was assessed at the indicated time points by immunoblot analysis. Simple incubation of parental HCT116 cells with the L15 (GAC ACG CTT CCC TGG (SEQ ID NO: 9)) oligonucleotide attenuated both p53 induction and cell death (FIG. 4A) induced by treatment with 5-FU. L15 had no measurable effect in p53-null (P53$^{-/-}$) HCT116 cells. Similarly, introduction of L15 into HCT116 cells led to a marked p53-dependent growth advantage in cells exposed to the DNA damaging agent etoposide.

Example 5

Discussion

It is well established that the binding of the E3-ubiquitin ligase, MDM2, to p53 protein regulates the half-life of p53 protein and is a major modulator of both basal and damage-induced p53 protein levels (Ashcroft and Vousden, 1999; Michael and Oren, 2003). It has also been reported that increases in p53 mRNA translation are a requisite component of optimal p53 induction following DNA damage and are dependent on the ability of RPL26 protein to bind to the 5'-UTR of p53 mRNA (Takagi et al., 2005; Ofir-Rosenfeld et al., 2008). While not wishing to be bound by any particular mechanism of action, the data presented here provide significant new mechanistic insights into how p53 translation and p53 induction are regulated by RPL26 and suggest a novel model of mammalian protein translational regulation.

Though independent binding of RPL26 protein to the 5'-UTR of p53 mRNA was previously reported (Takagi et al, 2005), here are provided data demonstrating that RPL26 binding and p53 translational stimulation are further enhanced by the additional presence of the 3'-UTR of p53 mRNA. A region of complementarity and interaction between the 5' and 3' UTRs of p53 mRNA has been presently identified, and it is presently discovered that the ability of RPL26 to bind to p53 mRNA and stimulate its translation are optimal in the presence of this 5'-3'UTR double-strand RNA structure.

Surprisingly, as shown in the present Examples, disruption of as few as three nucleotides in the double-strand RNA structure was sufficient to abrogate RPL26 binding and translational stimulation. Restoration of binding and translational stimulation by compensatory mutations that restore complementarity demonstrated that the RNA structure, rather than the primary RNA sequence, plays the dominant role in RPL26 regulation of p53 translation and induction.

After DNA damage, the increased translation of p53 mRNA is dependent on the binding of RPL26 to p53 mRNA and the subsequent enhanced association of p53 mRNA with heavy polysomes (Takagi et al., 2005). The mechanism by which RPL26 binding to p53 mRNA is stimulated by exposure of cells to DNA damage remains to be elucidated, but it could involve modulation of Mdm2 binding to RPL26 protein following DNA damage (Ofir-Rosenfeld et al., 2008). While not wishing to be bound by any particular theory, the increased binding of RPL26 to p53 mRNA after DNA damage is detectable in the nucleus, suggesting that this mechanism reflects a non-ribosomal function of RPL26 protein.

UTRs have been implicated in the regulation of protein translation through recruiting protein regulators (Standart and Jackson, 1994), small non-coding RNAs (Vasudevan et al., 2007; Grivna et al., 2006b; Grivna et al., 2006a), or by forming secondary structures that affect interactions with translational machinery (Sonenberg and Hinnebusch, 2009; Gray and Hentze, 1994). Both 5'- and 3'-UTR sequences have been demonstrated to have important roles in controlling translation of eukaryotic mRNAs (Pickering and Willis, 2005; Kuersten and Goodwin, 2003), including p53 (Schumacher et al., 2005; Mosner et al., 1995; Mazan-Mamczarz et al., 2003; Fu and Benchimol, 1997). Among the more typical scenarios would be control of translation mechanisms by 5'-UTR sequences and control of mRNA stability by 3'-UTR sequences (Melefors and Hentze, 1993; Sachs, 1993).

Interactions between 5' and 3' mRNA ends in translational control have also been described, including a recent report of two distinctive closed-loop mRNP structures stabilized by eIF4E, eIF4G and eIF3 initiation factors which circularize a capped mammalian mRNA by bridging the 5' CAP structure with proteins bound at the 3' poly(A) tail (Amrani et al., 2008; Sonenberg and Hinnebusch, 2007; Sonenberg and Hinnebusch, 2009). In this case, the circularization of the mRNA facilitates cap dependent translation. However, this 5'-3' interaction occurs between generic structures (5' CAP and 3' poly (A) tail) and is not an interaction between complementary sequences.

Gene specific translational control by interactions between 5' and 3' UTR sequences have been described in bacteria (Franch et al., 1997) and RNA viruses (Edgil and Harris, 2006), but rarely in eukaryotic RNAs. An unusual example is the Barley yellow dwarf luteovirus (BYDV) mRNA which forms a closed loop by direct interaction between 5'- and 3'-UTR sequences in the absence of protein factors as a mechanism of controlling efficiency of translation initiation (Guo et al., 2001).

The data herein provide an example of regulating mammalian protein translation by formation of a double-strand RNA structure involving base pairing between a 5'- and a 3'-UTR to regulate translation of a discrete mRNA. Mathematical modeling suggests that these interactions occur in p53 mRNA in a wide variety of species and are not limited to human p53.

In addition to the insights gained into novel mechanisms involved in the regulation of mammalian protein translation and to p53 induction after DNA damage, these results have identified a novel approach to regulating p53 protein levels in cells. Introduction of small oligonucleotides which disrupt this double-strand RNA structure into cells blocks the binding of RPL26 protein to p53 mRNA and reduces p53 induction following exposure to a variety of different DNA damaging agents. Blunting p53 induction with these oligonucleotides results in an increased cell survival following the toxic exposures. Oligonucleotides of sufficiently short length are presently discovered which are able to enter into cells without transfection and are able to blunt p53 induction simply by addition to cultured cells.

Though the induction of p53 protein after DNA damage and other stresses appears to be an important mechanism for limiting tumor development, there is a downside associated with p53 induction, namely associated tissue toxicity (Gudkov and Komarova, 2003). Toxicities such as bone marrow suppression and gastrointestinal injury seen with radiation therapy or chemotherapy for cancer or associated with accidental toxic exposures may be ameliorated by reducing p53 induction. For example, lethal total body irradiation fails to kill mice lacking p53 genes (Levine, 1997; Westphal et al., 1998). Thus, such inhibitors may be used to protect from tissue toxicity following accidental exposures to dangerous chemicals or radiation, but for use in cancer therapies one would likely only consider using p53 inhibitors to protect normal tissues during therapy for a p53-mutant tumor. Since a high percentage of human tumors contain mutant p53 (Levine, 1997), this could still have broad application.

A theoretical concern for blunting p53 induction in such settings might be the possibility of enhanced secondary tumors, but recent data suggest that restoration of p53 function to pre malignant or malignant cells is sufficient to provide anti-tumor effects (Ventura et al., 2007; Xue et al., 2007; Martins et al., 2006; Kastan, 2007). Since p53 function would only be transiently inhibited in this proposed setting, cancer promotion would be less of a concern. A small molecule, pifithrin, has previously been reported to block p53-dependent transcriptional activation and apoptosis (Komarov et al., 1999), but this agent does not block p53 induction, its molecular mechanism has not been elucidated, and it appears to have some off-target effects (Sohn et al., 2009).

Hypoxia and oxidative stress also induce p53 (Giaccia and Kastan, 1998) and blunting p53 induction can reduce tissue damage in settings of hypoxia-reperfusion injury, such as heart attack or stroke. Additional settings where transiently blunting p53 induction would be clinically useful are also contemplated by the present invention. It is also noted that blunting p53 induction in cultured cells is a useful tool in research settings as it can permit growth of cells in cultured systems that are typically difficult to grow because of "culture shock" (Sherr and DePinho, 2000). It is presently discovered, and demonstrated in the Examples that the short oligonucleotide, L15: GAC ACG CTT CCC TGG (SEQ ID NO: 9), can blunt p53 induction and enhance cell survival after chemotherapy exposure following simple addition to cultured cells.

The generation of improved oligonucleotides targeting the 5'-3' UTR interacting region in p53 mRNA that can block this specific process regulated by RPL26 and sequence-specific RNA interactions provides additional useful therapeutics and research tools.

Example 6

Literature Cited

Amrani, N., Ghosh, S., Mangus, D. A., and Jacobson, A. (2008). Translation factors promote the formation of two states of the closed-loop mRNP. Nature 453, 1276-1280.

Ashcroft, M. and Vousden, K. H. (1999). Regulation of p53 stability. Oncogene 18, 7637-7643.

Edgil, D. and Harris, E. (2006). End-to-end communication in the modulation of translation by mammalian RNA viruses. Virus Res. 119, 43-51.

Franch, T., Gultyaev, A. P., and Gerdes, K. (1997). Programmed cell death by hok/sok of plasmid R1: processing at the hok mRNA 3'-end triggers structural rearrangements that allow translation and antisense RNA binding. J. Mol. Biol. 273, 38-51.

Fu, L. and Benchimol, S. (1997). Participation of the human p53 3'UTR in translational repression and activation following y-irradiation. Embo J 16, 4117-4125.

Giaccia, A. J. and Kastan, M. B. (1998). The complexity of p53 modulation: emerging patterns from divergent signals. Genes & Development 12, 2973-2983.

Gray, N. K. and Hentze, M. W. (1994). Regulation of protein synthesis by mRNA structure. Mol. Biol. Rep. 19, 195-200.

Grivna, S. T., Beyret, E., Wang, Z., and Lin, H. (2006a). A novel class of small RNAs in mouse spermatogenic cells. Genes Dev. 20, 1709-1714.

Grivna, S. T., Pyhtila, B., and Lin, H. (2006b). MIWI associates with translational machinery and PIWI-interacting RNAs (piRNAs) in regulating spermatogenesis. Proc. Natl. Acad. Sci. U.S.A 103, 13415-13420.

Gruber, A. R., Lorenz, R., Bernhart, S. H., Neubock, R., and Hofacker, I. L. (2008). The Vienna RNA websuite. Nucleic Acids Res. 36, W70-W74.

Gudkov, A. V. and Komarova, E. A. (2003). The role of p53 in determining sensitivity to radiotherapy. Nat. Rev. Cancer 3, 117-129.

Guo, L., Allen, E. M., and Miller, W. A. (2001). Base-pairing between untranslated regions facilitates translation of uncapped, nonpolyadenylated viral RNA. Mol. Cell 7, 1103-1109.

Haupt, Y., Maya, R., Kazaz, A., and Oren, M. (1997). Mdm2 promotes the rapid degradation of p53. Nature 387, 296-299.

Hofacker, I. L. (2004). RNA secondary structure analysis using the Vienna RNA package. Curr. Protoc. Bioinformatics. *Chapter* 12, Unit.

Honda, R., Tanaka, H., and Yasuda, H. (1997). Oncoprotein MDM2 is a ubiquitin ligase E3 for tumor suppressor p53. FEBS Letters 420, 25-27.

Kastan, M. B. (2007). Wild-type p53: tumors can't stand it. Cell. 128, 837-840.

Kastan, M. B. and Bartek, J. (2004). Cell-cycle checkpoints and cancer. Nature 432, 316-323.

Komarov, P. G., Komarova, E. A., Kondratov, R. V., Christov-Tselkov, K., Coon, J. S., Chernov, M. V., and Gudkov, A. V. (1999). A chemical inhibitor of p53 that protects mice from the side effects of cancer therapy. Science 285, 1733-1737.

Kubbutat, M. H., Jones, S. N., and Vousden, K. H. (1997). Regulation of p53 stability by Mdm2. Nature 387, 299-303.

Kuersten, S, and Goodwin, E. B. (2003). The power of the 3' UTR: translational control and development. Nat. Rev. Genet. 4, 626-637.

Levine, A. J. (1997). p53, the Cellular Gatekeeper for Growth and Division. Cell 88, 323-331.

Malkin, D., Li, F. P., Strong, L. C., Fraumeni, J. F., Jr., Nelson, C. E., Kim, D. H., Kassel, J., Gryka, M. A., Bischoff, F. Z., Tainsky, M. A., and. (1990). Germ line p53 mutations in a familial syndrome of breast cancer, sarcomas, and other neoplasms. Science 250, 1233-1238.

Martins, C. P., Brown-Swigart, L., and Evan, G. I. (2006). Modeling the therapeutic efficacy of p53 restoration in tumors. Cell 127, 1323-1334.

Mazan-Mamczarz, K., Galban, S., Lopez, d. S., I, Martindale, J. L., Atasoy, U., Keene, J. D., and Gorospe, M. (2003). RNA-binding protein HuR enhances p53 translation in response to ultraviolet light irradiation. Proc. Natl. Acad. Sci. U.S.A 100, 8354-8359.

Melefors, O. and Hentze, M. W. (1993). Translational regulation by mRNA/protein interactions in eukaryotic cells: ferritin and beyond. BioEssays 15, 85-90.

Michael, D. and Oren, M. (2003). The p53-Mdm2 module and the ubiquitin system. Semin. Cancer Biol. 13, 49-58.

Mosner, J., Mummenbrauer, T., Bauer, C., Sczakiel, G., Grosse, F., and Deppert, W. (1995). Negative Feedback regulation of wild-type p53 biosynthesis. The EMBO Journal 14, 4442-4449.

Ofir-Rosenfeld, Y., Boggs, K., Michael, D., Kastan, M. B., and Oren, M. (2008). Mdm2 Regulates p53 mRNA Translation through Inhibitory Interactions with Ribosomal Protein L26. Molecular Cell 32, 180-189.

Pickering, B. M. and Willis, A. E. (2005). The implications of structured 5' untranslated regions on translation and disease. Semin. Cell Dev. Biol. 16, 39-47.

Prives, C. (1998). Signaling to p53: Breaking the MDM2-p53 circuit. Cell 95, 5-8.

Sachs, A. B. (1993). Messenger RNA degradation in eukaryotes. Cell 74, 413-421.

Schumacher, B., Hanazawa, M., L ee, M. H., Nayak, S., Volkmann, K., Hofmann, E. R., Hengartner, M., Schedl, T., and Gartner, A. (2005). Translational repression of C. elegans p53 by GLD-1 regulates DNA damage-induced apoptosis. Cell 120, 357-368.

Sherr, C. J. and DePinho, R. A. (2000). Cellular senescence: mitotic clock or culture shock. Cell 102, 407-410.

Sohn, D., Graupner, V., Neise, D., Essmann, F., Schulze-Osthoff, K., and Janicke, R. U. (2009). Pifithrin-alpha protects against DNA damage-induced apoptosis downstream of mitochondria independent of p53. Cell Death. Differ.

Sonenberg, N. and Hinnebusch, A. G. (2007). New modes of translational control in development, behavior, and disease. Mol. Cell 28, 721-729.

Sonenberg, N. and Hinnebusch, A. G. (2009). Regulation of translation initiation in eukaryotes: mechanisms and biological targets. Cell 136, 731-745.

Standart, N. and Jackson, R. J. (1994). Regulation of translation by specific protein/mRNA interactions. Biochimie 76, 867-879.

Takagi, M., Absalon, M. J., McLure, K. G., and Kastan, M. B. (2005). Regulation of p53 translation and induction after DNA damage by ribosomal protein L26 and nucleolin. Cell. 123, 49-63.

Vasudevan, S., Tong, Y., and Steitz, J. A. (2007). Switching from repression to activation:microRNAs can up-regulate translation. Science. 318, 1931-1934.

Ventura, A., Kirsch, D. G., McLaughlin, M. E., Tuveson, D. A., Grimm, J., Lintault, L., Newman, J., Reczek, E. E., Weissleder, R., and Jacks, T. (2007). Restoration of p53 function leads to tumour regression in vivo. Nature.

Westphal, C. H., Hoyes, K. P., Canman, C. E., Hua, X., Kastan, M. B., Hendry, J. H., and Leder, P. (1998). Loss of atm radiosensitizes multiple p53 null tissues. Cancer Res 58, 5637-5639.

Xue, W., Zender, L., Miething, C., Dickins, R. A., Hernando, E., Krizhanovsky, V., Cordon-Cardo, C., and Lowe, S. W. (2007). Senescence and tumour clearance is triggered by p53 restoration in murine liver carcinomas. Nature.

Yu, Y. and Little, J. B. (1998). p53 is involved in but not required for ionizing radiation-induced caspase-3 activation and apoptosis in human lymphoblast cell lines. Cancer Res. 58, 4277-4281.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed is:

1. A method for decreasing the level or induction of p53 protein in a cell, which method comprises administering to said cell an oligonucleotide which ranges from 7 to 50 nucleotides in length and comprises the sequence TCCCTGG (SEQ ID NO: 1) or the sequence CCAGGGA (SEQ ID NO: 2) in an amount effective for decreasing said level or induction of p53 protein.

2. The method of claim 1, wherein the cell has been subjected to a stress.

3. The method of claim 2, wherein the cellular stress is selected from the group consisting of ionizing radiation (IR), presence of a DNA damaging agent, hypoxia, hyperthermia, oxidation damage, chemotherapeutic agents, and ultraviolet (UV) light.

4. The method of claim 3, which method is used for achieving a medical effect selected from the group consisting of protection from toxicities of chemotherapy, protection from toxicities of radiation therapy, protection from toxicities of radiation exposure, reducing tissue/cell damage in hypoxia-reperfusion injury, reducing tissue/cell damage as a result of oxidative stress, reducing tissue/cell damage as a result of stresses associated with injuries, reducing tissue/cell damage in naturally occurring diseases, reducing tissue/cell damage in hyperthermia, inhibiting or decreasing tissue/cell aging, reducing or eliminating p53-dependent neuronal death or damage, preservation of tissues and organs prior to transplanting, and protection of cells of the central nervous system from cytotoxicity associated with neurodegenerative disorders.

5. A method for preventing negative effects of a cellular stress in a subject in need thereof, which method comprises administering to the subject a therapeutically effective amount of an oligonucleotide which ranges from 7 to 50 nucleotides in length and comprises the sequence TCCCTGG (SEQ ID NO: 1) or the sequence CCAGGGA (SEQ ID NO: 2).

6. The method of claim 5, wherein the cellular stress is selected from the group consisting of ionizing radiation, presence of a DNA damaging agent, hypoxia, hyperthermia, oxidation damage, chemotherapeutic agents, and ultraviolet (UV) light.

7. The method of claim 5, which method is used for achieving a medical effect selected from the group consisting of protection from toxicities of chemotherapy, protection from toxicities of radiation therapy, protection from toxicities of radiation exposure, reducing tissue/cell damage in hypoxia-reperfusion injury, reducing tissue/cell damage as a result of oxidative stress, reducing tissue/cell damage as a result of stresses associated with injuries, reducing tissue/cell damage in naturally occurring diseases, reducing tissue/cell damage in hyperthermia, inhibiting or decreasing tissue/cell aging, reducing or eliminating p53-dependent neuronal death or damage, and preservation of tissues and organs prior to transplanting.

8. The method of claim 5, wherein the subject is human.

9. The method of claim 1, wherein said oligonucleotide ranges from 7 to 21 nucleotides in length.

10. The method of claim 1, wherein said oligonucleotide contains a modification.

11. The method of claim 10, wherein said oligonucleotide is an LNA-modified oligonucleotide.

12. The method of claim 1, wherein said oligonucleotide is linked to a heterologous moiety.

13. A method for decreasing the level or induction of p53 protein in a cell, which method comprises administering to said cell an oligonucleotide in an amount effective for decreasing said level or induction of p53 protein, wherein said oligonucleotide consists of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGACACGCTTCCCTGG (SEQ ID NO: 11), CCAGGGAAGCGTGTCACC (SEQ ID NO: 12), GACGGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACACAACCAACTGG (SEQ ID NO: 16).

14. The method of claim 1, wherein said oligonucleotide is capable of disrupting the interaction between the 5' untranslated region (UTR) and the 3' UTR of p53 mRNA.

15. The method of claim 1, wherein the cell is a human cell.

16. The method of claim 5, wherein said oligonucleotide ranges from 7 to 21 nucleotides in length.

17. The method of claim 5, wherein said oligonucleotide contains a modification.

18. The method of claim 17, wherein said oligonucleotide is an LNA-modified oligonucleotide.

19. The method of claim 5, wherein said oligonucleotide is linked to a heterologous moiety.

20. A method for preventing negative effects of a cellular stress in a subject in need thereof, which method comprises administering to the subject a therapeutically effective amount of an oligonucleotide, wherein said oligonucleotide consists of the sequence selected from the group consisting of TCCCTGG (SEQ ID NO: 1), CCAGGGA (SEQ ID NO: 2), TTCCCTGG (SEQ ID NO: 3), CCAGGGAA (SEQ ID NO: 4), CTTCCCTGG (SEQ ID NO: 5), CCAGGGAAG (SEQ ID NO: 6), ACGCTTCCCTGG (SEQ ID NO: 7), CCAGGGAAGCGT (SEQ ID NO: 8), GACACGCTTCCCTGG (SEQ ID NO: 9), CCAGGGAAGCGTGTC (SEQ ID NO: 10), GGTGACACGCTTCCCTGG (SEQ ID NO: 11), CCAGGGAAGCGTGTCACC (SEQ ID NO: 12), GACGTGACACGCTTCCCTGG (SEQ ID NO: 13), CCAGGGAAGCGTGTCACCGTC (SEQ ID NO: 14), TTTACGCTTCCCTGG (SEQ ID NO: 15), and GACACAACCAACTGG (SEQ ID NO: 16).

21. The method of claim 5, wherein said oligonucleotide is capable of disrupting the interaction between the 5' untranslated region (UTR) and the 3' UTR of p53 mRNA.

* * * * *